United States Patent [19]

McGhee et al.

[11] Patent Number: 5,233,010
[45] Date of Patent: Aug. 3, 1993

[54] PROCESS FOR PREPARING ISOCYANATE AND CARBAMATE ESTER PRODUCTS

[75] Inventors: William D. McGhee, St. Louis; Michael K. Stern, University City; Thomas E. Waldman, Chesterfield, all of Mo.

[73] Assignee: Monsanto Company, St. Louis, Mo.

[21] Appl. No.: 961,594

[22] Filed: Oct. 15, 1992

[51] Int. Cl.$^5$ ............................................. C08G 18/72
[52] U.S. Cl. ........................................ 528/67; 528/84; 560/330; 560/334; 560/335; 560/336; 560/338; 560/343; 560/345
[58] Field of Search .................... 528/67, 84; 560/330, 560/334, 335, 336, 338, 343, 345

[56] References Cited

U.S. PATENT DOCUMENTS

| 2,822,395 | 2/1958 | Dent | 260/576 |
| 3,340,302 | 9/1967 | Young | 260/576 |
| 3,414,616 | 12/1968 | Summers et al. | 260/576 |
| 3,481,967 | 12/1969 | Ottmann et al. | 260/553 |
| 3,847,990 | 11/1974 | Blahak | 260/576 |
| 3,919,278 | 11/1975 | Rosenthal et al. | 260/453 |
| 3,919,279 | 11/1975 | Rosenthal et al. | 260/453 |
| 3,919,280 | 11/1975 | Rosenthal et al. | 260/453 |
| 3,962,302 | 6/1976 | Rosenthal et al. | 260/453 |
| 4,081,472 | 3/1978 | Tsumura et al. | 260/453 |
| 4,122,118 | 10/1978 | George et al. | 260/576 |

(List continued on next page.)

FOREIGN PATENT DOCUMENTS

| 293999 | 12/1988 | European Pat. Off. |
| 453885 | 10/1991 | European Pat. Off. |
| 60-231640 | 11/1985 | Japan |
| 1440767 | 6/1976 | United Kingdom |

OTHER PUBLICATIONS

Ayyangar, N. R. et al., "A Novel Reaction of Acetanilide with Nitrobenzene in DMSO-An Unusual Solvent Assisted Regioselective Aromatic Nucleophilic Substitution", *Tetrahedron Letters*, vol. 31, No. 22, pp. 3217-3120 (1990).

Wohl, A., "Toward the Knowledge of the Reaction Between Nitrobenzene and Aniline in the Presence of Alkali", *Chemische Berichte*, 36, pp. 4135-4138 (1903).

Wohl, A. and Aue, W., *Chemische Berichte*, 34, pp. 2442-2450 (1901).

Banerjee, A. A. and Mukesh, D., "Heterogeneous Catalytic Transfer Hydrogenation of 4-Nitrodiphenylamine to p-Phenylenediamines", *J. Chem. Soc., Chem. Comm.*, 18, 1275-76 (1988).

Rylander, W. P., "Catalytic Hydrogenation in Organic Synthesis", Academic Press, pp. 113-114 and 299 (1979).

Jencks, W. P., *J. Am. Chem. Soc.*, 92, 3201-3202 (1970).

Jeon, S. and Sawyer, D. T., "Hydroxide-Induced Synthesis of the Superoxide Ion from Dioxygen and Aniline, Hydroxlamine, or Hydrazine", *Inorg. Chem.*, 29, 4612-15 (1990).

Bentley, T. W., "Electrochemical Oxidative Substitution and Dimerization of 1-arylazo-2-naphthols, Leading to a New Synthesis of Some Unsymmetrical Diaryl-

*Primary Examiner*—Maurice J. Welsh
*Attorney, Agent, or Firm*—Kenneth D. Goetz; Paul L. Passley; James C. Bolding

[57] ABSTRACT

A process for preparing an isocyanate having at least two —N=C=O groups is provided which comprises preparing a substituted aromatic amine having at least two —NH$_2$ groups, recovering the substituted aromatic amine having at least two —NH$_2$ groups, and preparing an isocyanate from the substituted aromatic amine having at least two —NH$_2$ groups by (1) contacting the substituted aromatic amine with CO$_2$ under conditions sufficient to produce the corresponding ammonium carbamate salt, and reacting the ammonium carbamate salt with an electrophilic or oxophilic dehydrating agent under conditions sufficient to produce the corresponding isocyanate, or (2) contacting the substituted aromatic amine with CO$_2$ under conditions sufficient to produce the corresponding ammonium carbamate salt, reacting the ammonium carbamate salt with a primary or secondary hydrocarbyl halide in a polar aprotic solvent under conditions sufficient to produce the corresponding carbamate ester, and cracking the carbamate ester under conditions sufficient to produce the corresponding isocyanate.

97 Claims, No Drawings

U.S. PATENT DOCUMENTS

| | | | |
|---|---|---|---|
| 4,130,576 | 12/1978 | Hedaya et al. | 260/576 |
| 4,140,716 | 2/1979 | Maender et al. | 260/576 |
| 4,155,936 | 5/1979 | Sturm | 260/576 |
| 4,178,309 | 12/1979 | Luetzow et al. | 260/553 |
| 4,178,315 | 12/1979 | Zengel et al. | 260/576 |
| 4,187,248 | 2/1980 | Merten et al. | 260/576 |
| 4,187,249 | 2/1980 | Merten et al. | 260/571 |
| 4,192,815 | 3/1980 | Sheludyakov et al. | 260/576 |
| 4,196,146 | 4/1980 | Merten et al. | 260/571 |
| 4,209,463 | 6/1980 | Maender et al. | 260/571 |
| 4,297,501 | 10/1981 | Becker et al. | 560/24 |
| 4,330,479 | 5/1992 | Merger et al. | 260/453 |
| 4,341,898 | 7/1982 | Milligan et al. | 560/24 |
| 4,388,238 | 6/1983 | Heikämper et al. | 560/24 |
| 4,388,241 | 6/1983 | Sundermann et al. | 260/453 |
| 4,404,401 | 9/1983 | Zengel et al. | 564/410 |
| 4,463,191 | 7/1984 | Sidocky et al. | 564/410 |
| 4,467,089 | 8/1984 | Bechara | 260/453 |
| 4,479,008 | 10/1984 | Batorewicz et al. | 564/410 |
| 4,518,803 | 5/1985 | Batorewicz et al. | 564/410 |
| 4,567,294 | 1/1986 | Dressel et al. | 260/553 |
| 4,582,923 | 4/1986 | Stammann et al. | 560/24 |
| 4,614,817 | 9/1986 | Maender et al. | 564/415 |
| 4,670,595 | 6/1987 | Podder et al. | 564/415 |
| 4,683,332 | 7/1987 | Sturm | 564/415 |
| 4,760,186 | 7/1988 | Solodar | 564/415 |
| 4,795,795 | 1/1989 | Kouno et al. | 260/453 |
| 4,900,868 | 2/1990 | Merten et al. | 564/398 |
| 5,117,063 | 5/1992 | Stern et al. | 564/398 |

OTHER PUBLICATIONS amines", *Tetrahedron Letters*, vol. 27, No. 43, pp. 5261–5264 (1986).

Belforte, A. et al., "Incorporation and Deoxygenation of Carbon Dioxide: A Metal-Assisted Facile conversion of Carbon Dioxide and Primary Amines to Isocyanates", *Chem. Ber.*, 121, 1891–97 (1988).

Hori, Y., et al., New Organic Synthesis with DBU: Part 7. Synthesis of Carbonates and Carbamates with Carbon Dioxide Gas as the Starting Material:, *Chemistry Express*, vol. 1, No. 4, pp. 224–227 (1986).

Yoshida, Y. et al., "Novel Synthesis of Carbamate Ester from Carbon Dioxide, Amines, and Alkyl Halides", *Bull. Chem. Soc. Jpn.*, vol. 62, No. 5, pp. 1534–1538 (1989).

Aresta, M. and Quaranta, E., "Role of the Macrocyclic Polyether in the Synthesis of N-Alkylcarbamate Esters from Primary Amines, $CO_2$ and Alkyl Halides in the Presence of Crown-Ethers", *Tetrahedron*, vol. 48, No. 8, pp. 1515–1530 (1992).

PROCESS FOR PREPARING ISOCYANATE AND CARBAMATE ESTER PRODUCTS

BACKGROUND OF THE INVENTION

This invention relates to the production of isocyanates having at least two —N=C=O groups. In one aspect, this invention relates to the production of diisocyanates. This invention also relates to the production of carbamate esters having at least two

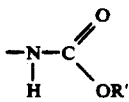

groups. In another aspect, this invention relates to the production of bis(carbamate esters). This inventions further relates to polyamides prepared from such isocyanates.

Commercially, the phosgenation of primary amines is by far the most widely used method for producing isocyanates. The use of phosgene, however, has several disadvantages. The phosgenation route is long, energy intensive and requires handling highly corrosive materials, e.g., hydrogen chloride, chlorine, sulfuric acid and nitric acid, and highly toxic reagents and intermediates, e.g., phosgene and chlorine. Furthermore, the phosgenation route requires use of process equipment which can withstand high temperatures and highly corrosive conditions resulting in increased capital costs. For example, p-phenylenediisocyanate is prepared via the phosgenation of p-phenylenediamine. This route produces 4 moles of hydrogen chloride per mole of diisocyanate and requires the handling of both gaseous phosgene and gaseous hydrogen chloride. In addition, the product is frequently contaminated with the intermediate carbamyl chloride or symmetric urea as a result of incomplete conversion of the diamine.

Carbamate esters are typically prepared by reaction of an isocyanate, prepared as above, with an alcohol. This process has the same disadvantages as discussed above for the production of isocyanates. Carbamate esters can also be prepared via reductive carbonylation of an amine utilizing high pressures of toxic carbon monoxide and high temperatures in the presence of an alcohol and a catalyst.

Substituted aromatic amines having at least two —NH$_2$ groups, e.g., p-phenylenediamine, are typically prepared via a halide route which is disadvantageous in that halide appears in the waste stream and must be disposed of at considerable expense. p-Phenylenediamine is currently produced via two different routes. The first route involves the use of p-nitrochlorobenzene. This route uses chlorine gas and generates chloride salts as a major waste product. The second route involves the nitrosation of aniline followed by thermal rearrangement. This route requires hydrogen chloride, produces a mixture of isomers, and produces nitrosoamines and benzidine as by-products.

A nonhalide route to substituted aromatic amines having at least two —NH$_2$ groups, which could be utilized in the preparation of the corresponding isocyanates or carbamate esters, would provide significant advantages over current commercial technology and result in a more efficient and economic commercial process.

A nonphosgene process for preparing the isocyanates or carbamate esters of the invention which is economical and commercially viable, and includes the preparation of substituted aromatic amines having at least two —NH$_2$ groups via a nonhalide route is highly desirable.

SUMMARY OF THE INVENTION

It is an object of the invention to provide an economic and efficient process for preparing isocyanates having at least two —N=C=O groups that is commercially viable. It is a further object of the invention to provide a process for preparing isocyanates having at least two —N=C=O groups which are not easily synthesized via phosgene routes. It is a still further object of the invention to provide an economic and efficient process for preparing carbamate esters having at least

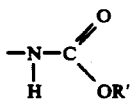

groups that is commercially viable. It is yet another object of the invention to provide an economic and efficient process for preparing polyamides from the isocyanates of the invention that is commercially viable.

According to the invention, a process for preparing an isocyanate having at least two —N=C=O groups is provided which comprises preparing a substituted aromatic amine having at least two —NH$_2$ groups, recovering the substituted aromatic amine having at least two —NH$_2$ groups, and preparing an isocyanate from the substituted aromatic amine having at least two —NH$_2$ groups by (1) contacting the substituted aromatic amine with CO$_2$ under conditions sufficient to produce the corresponding ammonium carbamate salt, and reacting the ammonium carbamate salt with an electrophilic or oxophilic dehydrating agent under conditions sufficient to produce the corresponding isocyanate, or (2) contacting the substituted aromatic amine with CO$_2$ under conditions sufficient to produce the corresponding ammonium carbamate salt, reacting the ammonium carbamate salt with a primary or secondary hydrocarbyl halide in a polar aprotic solvent under conditions sufficient to produce the corresponding carbamate ester, and cracking the carbamate ester under conditions sufficient to produce the corresponding isocyanate. In one embodiment, the isocyanate having at least two —N=C=O groups is recovered and contacted with a dicarboxylic acid or salt thereof under polymerization conditions sufficient to produce the corresponding polyamide.

Further according to the invention, a process for preparing a carbamate ester having at least two

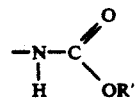

groups is provided which comprises preparing a substituted aromatic amine having at least two —NH$_2$ groups, recovering the substituted aromatic amine having at least two —NH$_2$ groups, and preparing a carbamate ester by contacting the substituted aromatic amine with CO$_2$ under conditions sufficient to produce the corresponding ammonium carbamate salt, and reacting the ammonium carbamate salt with a primary or secondary hydrocarbyl halide in a polar aprotic solvent under conditions sufficient to produce the corresponding carbamate ester.

DETAILED DESCRIPTION OF THE INVENTION

The isocyanates of the present invention, especially diisocyanates, are readily recoverable and useful in applications such as preparation of urethane foams, urethane elastomers, coatings, insecticides, herbicides, polyamides, and the like. The carbamate esters of the present invention are readily recoverable and useful in specialty chemical applications. The polyamides of the present invention are readily recoverable and useful in applications such as high performance fibers.

A first embodiment of the invention relates to a process for preparing an isocyanate having at least two —N=C=O groups comprising (a) preparing a substituted aromatic amine having at least two —$NH_2$ groups, (b) recovering the substituted aromatic amine having at least two —$NH_2$ groups, and (c) (i) contacting $CO_2$ and the substituted aromatic amine having at least two —$NH_2$ groups in the presence of an aprotic organic solvent and an organic, nitrogenous base under reaction conditions of time and temperature sufficient to produce the corresponding ammonium carbamate salt and (ii) reacting the ammonium carbamate salt with an electrophilic or oxophilic dehydrating agent under reaction conditions of time and temperature sufficient to produce the corresponding isocyanate having at least two —N=C=O groups, or ($c_1$)(i) contacting $CO_2$ and the substituted aromatic amine having at least two —$NH_2$ groups in the presence of an organic, nitrogenous base selected from the group consisting of guanidine compounds, amidine compounds, phosphazene compounds and mixtures thereof, under reaction conditions of time and temperature sufficient to produce the corresponding ammonium carbamate salt, (ii) reacting, in a polar aprotic solvent, the ammonium carbamate salt with a primary or secondary hydrocarbyl halide under reaction conditions sufficient to produce the corresponding carbamate ester, and (iii) cracking the carbamate ester under conditions sufficient to produce the corresponding isocyanate having at least two —N=C=O groups.

For producing polyamide, the process of the invention further comprises (d) recovering the isocyanate having at least two —N=C=O groups, and (e) contacting the isocyanate having at least two —N=C=O groups with a dicarboxylic acid in the presence of a suitable solvent system and a suitable base under polymerization conditions of time and temperature sufficient to produce the corresponding polyamide provided that the suitable base is optional when the suitable solvent functions as a suitable base, or ($e_1$) contacting the isocyanate having at least two —N=C=O groups with a salt of a dicarboxylic acid in the presence of a suitable solvent system under polymerization conditions of time and temperature sufficient to produce the corresponding polyamide.

A second embodiment of the invention relates to a process for preparing a carbamate ester having at least two

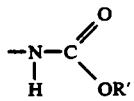

groups comprising (a) preparing a substituted aromatic amine having at least two —$NH_2$ groups, (b) recovering the substituted aromatic amine having at least two —$NH_2$ groups, and (c) (i) contacting $CO_2$ and the substituted aromatic amine having at least two —$NH_2$ groups in the presence of an organic, nitrogenous base selected from the group consisting of guanidine compounds, amidine compounds, phosphazene compounds and mixtures thereof, under reaction conditions of time and temperature sufficient to produce the corresponding ammonium carbamate salt, and (ii) reacting, in a polar aprotic solvent, the ammonium carbamate salt with a primary or secondary hydrocarbyl halide under reaction conditions sufficient to produce the corresponding carbamate ester.

The substituted aromatic amine having at least two —$NH_2$ groups prepared in Step (a) of both the process for preparing the isocyanate and the process for preparing the carbamate ester described above can be prepared by any of several processes including:

(a)

(i) contacting an amide selected from the group consisting of diamides, substituted aliphatic amides represented by the formula

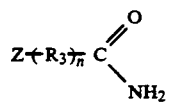

and substituted aromatic amides containing at least one substituent on the aromatic ring selected from the group consisting of —$NO_2$, —$NH_2$ and alkyl, aryl, aralkyl and alkaryl groups containing at least one —$NH_2$ group, and nitrobenzene in the presence of a suitable solvent system wherein n is 0 or 1, $R_3$ is selected from the group consisting of alkyl, aralkyl, alkenyl, aralkenyl, cycloalkyl and cycloalkenyl groups, and Z is selected from the group consisting of —$NO_2$, —$NH_2$ and alkyl, aryl, aralkyl and alkaryl groups containing at least one —$NH_2$ group, (ii) reacting said amide of (a)(i) and nitrobenzene in the presence of a suitable base and a controlled amount of protic material at a suitable temperature in a confined reaction zone, and (iii) reducing the reaction product of (a)(ii) under conditions which produce a substituted aromatic amine having at least two —$NH_2$ groups; or ($a_1$)

(i) contacting an amide and nitrobenzene in the presence of a suitable solvent system, (ii) reacting said amide of ($a_1$)(i) and nitrobenzene in the presence of a suitable base and a controlled amount of protic material at a suitable temperature in a confined reaction zone to produce a p-nitroaromatic amide, (iii) reducing said p-nitroaromatic amide of ($a_1$)(ii) under conditions which produce a p-aminoaromatic amide, and (iv) reacting said p-aminoaromatic amide with ammonia under conditions which produce the corresponding substituted aromatic amine having at least two —$NH_2$ groups and amide; or (a₂)
(i) contacting an amide and nitrobenzene in the presence of a suitable solvent system,
(ii) reacting said amide of (a₂)(i) and nitrobenzene in the presence of a suitable base and a controlled amount of protic material at a suitable temperature in a confined reaction zone to produce a p-nitroaromatic amide,
(iii) reacting said p-nitroaromatic amide of (a₂)(ii) with ammonia under conditions which produce the corresponding p-nitroaromatic amine and amide, and
(iv) reducing said p-nitroaromatic amine under conditions which produce the corresponding substituted aromatic amine having at least two —NH₂ groups; or
(a₃)
(i) contacting an amide or a substituted aromatic amine having at least two —NH₂ groups, wherein said amide is selected from the group consisting of diamides, substituted aliphatic amides represented by the formula

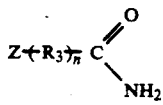

and substituted aromatic amides containing at least one substituent on the aromatic ring selected from the group consisting of —NH₂ and alkyl, aryl, aralkyl and alkaryl groups containing at least one —NH₂ group, and an azo containing compound represented by the formula X—R₁—N=N—R₂—Y or azoxy or hydrazo derivatives thereof in the presence of a suitable solvent system wherein n is 0 or 1, R₃ is selected from the group consisting of alkyl, aralkyl, alkenyl, aralkenyl, cycloalkyl and cycloalkenyl groups, Z is selected from the group consisting of —NH₂ and alkyl, aryl, aralkyl and alkaryl groups containing at least one —NH₂ group, R₁ is an aromatic group, R₂ is selected from the group consisting of aliphatic and aromatic groups, and X and Y are independently selected from the group consisting of hydrogen, halides, —NO₂, —NH₂, aryl groups, alkyl groups, alkoxy groups, —SO₃, —SO₃R₃₀, —OR₃₀, —COOR₃₀, and alkyl, aryl, aralkyl or alkaryl groups containing at least one —NH₂ group, wherein R₃₀ is selected from the group consisting of aliphatic and aromatic groups, if R₂ is aliphatic, X is in the meta or ortho position on R₁ and if R₂ is aromatic, at least one of X and Y is in the meta or ortho position on R₁ and R₂, respectively, and wherein halides are selected from the group consisting of chloride, bromide and fluoride,
(ii) reacting said amide or substituted aromatic amine having at least two —NH₂ groups of (a₃)(i) and said azo containing compound in the presence of a suitable base and a controlled amount of protic material at a reaction temperature of about 10° C. to about 150° C. in a confined reaction zone to produce a substituted aromatic azo compound, wherein the molar ratio of protic material to base is 0:1 to about 5:1, and
(iii) reacting said substituted aromatic azo compound of (a₃)(ii) with a nucleophilic compound selected from the group consisting of aniline, substituted aniline derivatives, aliphatic amines, substituted aliphatic amine derivatives, amides and substituted aromatic amines having at least two —NH₂ groups in the presence of a suitable solvent system, a suitable base and a controlled amount of protic material at a reaction temperature of about 70° C. to about 200° C. in a confined reaction zone to produce a substituted aromatic amine having at least two —NH₂ groups, wherein the molar ratio of protic material to base is 0:1 to about 5:1; or
(a₄)
(i) contacting an amide and an azo containing compound represented by the formula X—R₁—N=N—R₂—Y or azoxy or hydrazo derivatives thereof in the presence of a suitable solvent system, wherein R₁ is an aromatic group, R₂ is selected from the group consisting of aliphatic and aromatic groups, and X and Y are independently selected from the group consisting of hydrogen, halides, —NO₂, —NH₂, aryl groups, alkyl groups, alkoxy groups, —SO₃, —SO₃R₃₀, —OR₃₀, —COOR₃₀, and alkyl, aryl, aralkyl or alkaryl groups containing at least one —NH₂ group, wherein R₃₀ is selected from the group consisting of aliphatic and aromatic groups, if R₂ is aliphatic, X is in the meta or ortho position on R₁ and if R₂ is aromatic, at least one of X and Y is in the meta or ortho position on R₁ and R₂, respectively, and wherein halides are selected from the group consisting of chloride, bromide and fluoride,
(ii) reacting said amide of (a₄)(i) and said azo containing compound in the presence of a suitable base and a controlled amount of protic material at a reaction temperature of about 10° C. to about 150° C. in a confined reaction zone to produce a substituted aromatic azo compound, wherein the molar ratio of protic material to base is 0:1 to about 5:1;
(iii) reacting said substituted aromatic azo compound of (a₄)(ii) with a nucleophilic compound selected from the group consisting of aniline, substituted aniline derivatives, aliphatic amines, substituted aliphatic amine derivatives, amides and substituted aromatic amines having at least two —NH₂ groups in the presence of a suitable solvent system, a suitable base and a controlled amount of protic material at a reaction temperature of about 70° C. to about 200° C. in a confined reaction zone to produce a substituted aromatic amine containing an aromatic amide bond wherein the molar ratio of protic material to base is 0:1 to about 5:1, and
(iv) reacting said substituted aromatic amine of (a₄)(iii) with ammonia under conditions which produce the corresponding substituted aromatic amine having at least two —NH₂ groups and amide; or
(a₅)
(i) contacting a nucleophilic compound selected from the group consisting of aniline, substituted aniline derivatives, aliphatic amines, substituted aliphatic amine derivatives, amides and substituted aromatic amines having at least two —NH₂ groups with a substituted aromatic azo compound or azoxy or hydrazo derivatives thereof in the presence of a suitable solvent system, and (ii) reacting said nucleophilic compound and said substituted aromatic azo compound or azoxy or hydrazo derivatives thereof in the presence of a suitable base and a controlled amount of protic material at a reaction temperature of about 70° C. to about 200° C. to produce a substituted aromatic amine having at least two —NH₂ groups, wherein the molar ratio of protic material to base is 0:1 to about 5:1, wherein the substituted aromatic azo compound is selected from the group consisting of compounds represented by the formula:

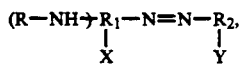 (I)

compounds represented by the formula:

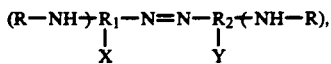 (II)

compounds represented by the formula:

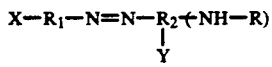 (III)

and mixtures thereof, wherein R—NH— represents a substituent derived from an amide or a substituted aromatic amine having at least two —NH$_2$ groups, wherein said amide is selected from the group consisting of diamides, substituted aliphatic amides represented by the formula

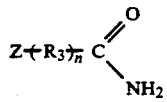

and substituted aromatic amides containing at least one substituent on the aromatic ring selected from the consisting of —NH$_2$ and alkyl, aryl, aralkyl and alkaryl groups containing at least one —NH$_2$ group, wherein n is 0 or 1, R$_3$ is selected from the group consisting of alkyl, aralkyl, alkenyl, aralkenyl, cycloalkyl and cycloalkenyl groups, Z is selected from the group consisting of —NH$_2$ and alkyl, aryl, aralkyl and alkaryl groups containing at least one —NH$_2$ group, R$_1$ is an aromatic group, R$_2$ is selected from the group consisting of aliphatic and aromatic groups, and X and Y are independently selected from the group consisting of hydrogen, halides, —NO$_2$, —NH$_2$, aryl groups, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected from the group consisting of aliphatic and aromatic groups, halides are selected from the group consisting of chlorine, bromine and fluorine and R$_2$ is an aromatic group in substituted aromatic azo compounds (II) and (III); or (a$_6$)

(i) contacting a nucleophilic compound selected from the group consisting of aniline, substituted aniline derivatives, aliphatic amines, substituted aliphatic amine derivatives, amides and substituted aromatic amines having at least two —NH$_2$ groups with a substituted aromatic azo compound or azoxy or hydrazo derivatives thereof in the presence of a suitable solvent system, (ii) reacting said nucleophilic compound and said substituted aromatic azo compound or azoxy or hydrazo derivatives thereof in the presence of a suitable base and a controlled amount of protic material at a reaction temperature of about 70° C. to about 200° C. to produce a substituted aromatic amine containing an aromatic amide bond, wherein the molar ratio of protic material to base is 0:1 to about 5:1, wherein the substituted aromatic azo compound is selected from the group consisting of compounds represented by the formula:

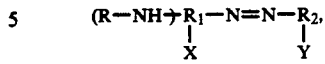 (I)

compounds represented by the formula:

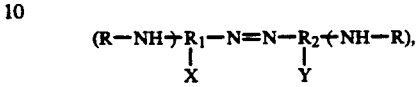 (II)

compounds represented by the formula:

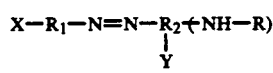 (III)

and mixtures thereof, wherein R—NH— represents a substituent derived from an amide, R$_1$ is an aromatic group, R$_2$ is selected from the group consisting of aliphatic and aromatic groups, and X and Y are independently selected from the group consisting of hydrogen, halides, —NO$_2$, —NH$_2$, aryl groups, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected from the group consisting of aliphatic and aromatic groups, halides are selected from the group consisting of chlorine, bromine and fluorine and R$_2$ is an aromatic group in substituted aromatic az compounds (II) and (III), and (iii) reacting said substituted aromatic amine of (a$_6$)(ii) with ammonia under conditions which produce the corresponding substituted aromatic amine having at least two —NH$_2$ groups and amide; or (a$_7$)

(i) contacting a substituted aniline derivative, wherein the substituents are selected from the group consisting of halide, —NO$_2$, —NH$_2$, alkyl groups, alkoxy groups, —SO$_3$, —COOR$_{30}$ and aryl, aralkyl or alkaryl groups containing at least one —NH$_2$ group provided said substituted aniline derivative contains at least one substituent selected from the group consisting of —NO$_2$, —NH$_2$ and aryl, aralkyl or alkaryl on groups containing at least one —NH$_2$ group, and nitrobenzene in a suitable solvent system, wherein R$_{30}$ is selected from the group consisting of aliphatic and aromatic groups, (ii) reacting said substituted aniline derivative and nitrobenzene in a confined reaction zone at a suitable temperature, and in the presence of a suitable base and a controlled amount of protic material, and (iii) reducing the reaction product of (a$_7$)(ii) under conditions to produce a substituted aromatic amine having at least two —NH$_2$ groups.

When the desired substituted aromatic amine having at least two —NH$_2$ groups is p-phenylenediamine, the p-phenylenediamine is produced by the process of Step (a$_1$), (a$_2$), (a$_4$) or (a$_6$). When p-phenylenediamine is used in the processes of the invention, the isocyanate produced is 1,4-phenylene diisocyanate and the carbamate ester produced is represented by the formula:

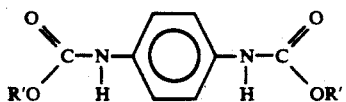

PREPARATION OF SUBSTITUTED AROMATIC AMINES

As used herein, the term "substituted aromatic amine having at least two —NH$_2$ groups" means an aromatic amine wherein the aromatic group is further substituted with at least one substituent containing an —NH$_2$ group or

group.

Examples of substituted aromatic amines containing at least two —NH$_2$ groups include, but are not limited to, p-phenylenediamine, 4,4'-diaminodiphenylamine, 4,4'-diaminobenzanilide, 4-amino-4'-(p-aminophenyl)-diphenylamine and mixtures thereof.

Embodiments a, a$_1$ and a$_2$

The p-nitroaromatic amide produced in the reaction of amide with nitrobenzene can be in the form of the neutral compound, i.e., not in the form of a salt, and/or in the form of the salt of such p-nitroaromatic amide. The salt is produced in the reaction mixture from reaction of the p-nitroaromatic amide with the base. Thus, the reaction mixture produced in the process of the invention can include the p-nitroaromatic amide compound, or salts or mixtures thereof depending on the specific reaction conditions selected.

The molar ratio of amide to nitrobenzene can vary from about 1:1 to a large excess of nitrobenzene. When nitrobenzene is used as the suitable solvent for the reaction, nitrobenzene is preferably present in a large excess relative to the amide. When nitrobenzene is not used as the solvent for the reaction, the molar ratio of amide to nitrobenzene can vary over a wide range, but is preferably about 1:1.

Amides that can be employed according to the invention include aromatic amides, aliphatic amides, substituted aromatic amide derivatives, substituted aliphatic amide derivatives and diamides having the formula:

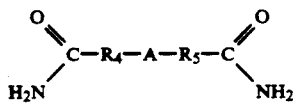

wherein R$_4$ and R$_5$ are independently selected from the group consisting of aromatic groups, aliphatic groups and a direct bond, and A is selected from the group consisting of

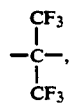

—SO$_2$—, —O—, —S— and a direct bond.

The aliphatic amides and substituted aliphatic amide derivatives that can be employed according to the invention are represented by the formula:

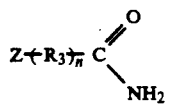

wherein n is 0 or 1, R$_3$ is selected from the group consisting of alkyl, aralkyl, alkenyl, aralkenyl, cycloalkyl and cycloalkenyl groups and Z is selected from the group consisting of hydrogen, —NO$_2$, —NH$_2$, aryl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group wherein R$_{30}$ is selected from the group consisting of aliphatic and aromatic groups. The preferred alkyl and alkoxy groups contain from 1 to about 6 carbon atoms. The preferred aryl, aralkyl and alkaryl groups contain from about 6 to about 18 carbon atoms.

Examples of aliphatic amides and substituted aliphatic amide derivatives include, but are not limited to, isobutyramide, urea, acetamide, propylamide and mixtures thereof.

As used herein, the term "substituted aromatic amide derivatives" means aromatic amides containing one or more electron withdrawing or electron releasing substituents on the aromatic ring. Applicable substituents include, but are not limited to, halides, —NO$_2$, —NH$_2$, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group wherein R$_{30}$ is as defined herein. Halides are selected from the group consisting of chloride, bromide and fluoride. The preferred alkyl and alkoxy groups contain from 1 to about 6 carbon atoms. The preferred aryl, aralkyl and alkaryl groups contain from about 6 to about 18 carbon atoms.

Examples of aromatic amides and substituted aromatic amide derivatives include, but are not limited to, benzamide, 4-methylbenzamide, 4-methoxybenzamide, 4-chlorobenzamide, 2-methylbenzamide, 4-nitrobenzamide, 4-aminobenzamide and mixtures thereof.

Diamides that can be employed according to the process of the invention include, but are not limited to, adipamide, oxalic amide, terephthalic diamide, 4,4'-biphenyldicarboxamide and mixtures thereof.

Suitable solvent systems include, but are not limited to, solvents such as, for example, nitrobenzene, dimethylsulfoxide, dimethylformamide, N-methyl-2-pyrrolidone, pyridine, N-methylaniline, chlorobenzene, tetraalkyl ammonium hydroxides or amides having a melting point below the reaction temperature, e.g., molten tetramethyl ammonium hydroxide and molten benzamide, and mixtures thereof. Preferably, nitrobenzene is used in excess in the reaction as stated above, and the nitrobenzene in excess of the molar amount of amide serves as the solvent. As described in more detail below, solvent mixtures can be utilized wherein one or more of the suitable solvents and another solvent, such as a controlled amount of a protic solvent, are combined. Examples of protic solvent include, but are not limited to, methanol, water and mixtures thereof.

Suitable bases include, but are not limited to, organic and inorganic bases such as alkali metals, such as sodium metal, alkali metal hydrides, hydroxides and alkoxides, such as sodium hydride, lithium hydroxide, sodium hydroxide, cesium hydroxide, potassium hydroxide, potassium t-butoxide, and the like, including mixtures thereof. Other acceptable base materials include, but are not limited to, phase transfer catalysts in conjunction with a suitable base source such as tetrasubstituted ammonium hydroxides or halides wherein each substituent is independently selected from alkyl, aryl or aralkyl groups wherein the alkyl, aryl and aralkyl groups preferably have 1 to about 18 carbon atoms, including tetraalkyl ammonium hydroxides, e.g., tetramethyl ammonium hydroxide, tetraalkyl ammonium halides, e.g., tetrabutyl ammonium chloride, aryl, trialkyl ammonium hydroxides, e.g., phenyltrimethylammonium hydroxide, aralkyl, trialkyl ammonium hydroxides, e.g., benzyltrimethyl ammonium hydroxide, alkyl substituted diammonium hydroxides, e.g., bis-dibutylethylhexamethylene diammonium hydroxide, and other combinations of phase transfer catalysts and suitable bases such as suitable bases in conjunction with aryl ammonium salts, crown ethers and the like, and amine bases such as lithium bis(trimethylsilyl) amide, and the like, and alkyl magnesium halides, including mixtures thereof. Preferred materials for use as bases are etraalkylammonium hydroxides such as tetramethylammonium hydroxide or tetrabutylammonium hydroxide.

Preferably, the base is added to the amide to produce a mixture which is then combined with the nitrobenzene. Alternatively, the base can be added after the amide and nitrobenzene have been combined. Addition of materials can be above or below surface addition.

The amount of base employed according to the invention can be conveniently expressed in terms of the ratio of equivalents of suitable base to equivalents of amide. Broadly, the ratio of equivalents of base to equivalents of amide will be about 1:1 to about 10:1, preferably about 1:1 to about 4:1, and most preferably about 1:1 to about 2:1.

The reaction is conducted at a suitable temperature which can vary over a wide range. For example, the temperature can fall within a range of from about 5° C. to about 150° C., such as from about 15° C. to about 100° C., preferably from about 25° C. to about 90° C. A most preferred temperature for conducting the reaction of the invention is from about 60° C. to about 80° C.

Control of the amount of protic material present in the reaction is important. The amount of protic material employed according to the invention can be conveniently expressed in terms of a molar ratio based on the amount of base present at the beginning of the reaction of amide and nitrobenzene. Broadly, the molar ratio of protic material to base will be less than about 5:1, preferably less than about 4:1, more preferably less than about 3:1, and most preferably less than about 1:1. Thus, the present reaction could be conducted under anhydrous conditions. As used herein for embodiments a, $a_1$ and $a_2$, the term "controlled amount" of protic material is an amount up to that which inhibits the reaction of amide with nitrobenzene. The upper limit for the amount of protic material present in the reaction varies with the solvent. In addition, the amount of protic material tolerated will vary with the type of base, amount of base, and base cation, used in the various solvent systems. However, it is within the skill of one in the art, utilizing the teachings of the present invention, to determine the specific upper limit of the amount of protic material for a specific solvent, type and amount of base, base cation and the like. The minimum amount of protic material necessary to maintain selectivity of the desired products will also depend upon the solvent, type and amount of base, base cation and the like, that is utilized and can also be determined by one skilled in the art.

Since the amount of protic material present in the reaction is important, it is possible to reduce the amount of protic material present as much as possible and then add back to the reaction the desired amount. Protic materials that can be utilized to add back to the reaction are known to those skilled in the art and include, but are not limited to, water, methanol and the like, and mixtures thereof. Methods for measuring the amount of protic material and for reducing the amount of protic material as much as possible are well known in the art. For example, the amount of water present in certain reagents can be determined by utilizing a Karl-Fischer apparatus, and the amount of water can be reduced through distillation and/or drying under reduced pressure, drying in the presence of $P_2O_5$ and other agents, azeotropic distillation utilizing, for example, xylene, and the like, including combinations thereof.

In one embodiment for controlling the amount of protic material during the reaction of amide and nitrobenzene, a desiccant is added so as to be present during the reaction of amide and nitrobenzene. For example, when the protic material is water, the desiccant removes water present during the reaction of amide and nitrobenzene and results in higher conversion of nitrobenzene and yields of p-nitroaromatic amide. As used herein, desiccant is a compound present during the reaction of amide and nitrobenzene in addition to the suitable base used. Examples of suitable desiccants include, but are not limited to, anhydrous sodium sulfate, molecular sieves, such as types 4A, 5A, and 13X available from the Union Carbide Corporation, calcium chloride, tetramethylammonium hydroxide dihydrate, anhydrous bases such as KOH and NaOH, and activated alumina.

In another embodiment for controlling the amount of protic material during the reaction of amide and nitrobenzene, protic material is continuously removed from the reaction mixture by distillation. If the protic material present forms an azeotrope with one of the compounds in the reaction mixture, the protic material can be removed by continuous azeotropic distillation of protic material utilizing the azeotrope. The continuous removal of protic material allows the use of lower amounts of base in the reaction of amide and nitrobenzene while achieving very high conversion of nitrobenzene and excellent yields of p-nitroaromatic amide.

The reaction can be conducted under aerobic or anaerobic conditions. Under aerobic conditions, the reaction is conducted essentially as described above in the reaction zone which is exposed to oxygen, usually by exposure to air. Under aerobic conditions, the pressure at which the reaction is conducted can vary and the optimal pressure, as well as the optimal combination of pressure and temperature, are easily determined by one skilled in the art. For example, the reaction can be conducted at room temperature and at a pressure ranging from about 10 psig to about 250 psig, such as from about 14 psig to about 150 psig. Under anaerobic conditions, the reaction can be conducted at atmospheric pressure or reduced or elevated pressures, in the presence of an inert gas such as, for example, nitrogen or argon. Optimal conditions for a particular set of reaction parameters, such as temperature, base, solvent and the like, are easily determined by one skilled in the art utilizing the teaching of the present invention.

The p-nitroaromatic amides and/or their salts can be reduced to p-aminoaromatic amides. The neutral compounds can be generated from the salts utilizing water and/or an acid. Alternatively, the salts can be reduced. In another embodiment of the invention, p-nitroaromatic amine can be reduced to p-aminoaromatic amine. These reductions can be carried out by any of many known reductive processes, such as using a hydride source, e.g., sodium borohydride in conjunction with palladium- or platinum-on-carbon catalysts. Preferably, this reduction is conducted by a catalytic reduction wherein hydrogenation is effected under hydrogen pressure in the presence of platinum- or palladium-on-carbon, nickel, and the like. This hydrogenation process is described in detail in "Catalytic Hydrogenation in Organic Synthesis", P. N. Rylander, Academic Press, N.Y., page 299 (1979), which is incorporated by reference herein. The hydrogenation can be conducted in a variety of solvents including, but not limited to, toluene, xylene, aniline, ethanol, dimethylsulfoxide, water and mixtures thereof. Preferably, the hydrogenation is conducted utilizing a platinum-on-carbon or palladium-on-carbon catalyst in a suitable solvent such as, for example, either ethanol, aniline, or dimethylsulfoxide, mixtures thereof, or mixtures which include water as the solvent and a hydrogen pressure of from 100 psig $H_2$ to about 340 psig $H_2$ at a temperature of about 80° C.

Aminolysis of p-nitroaromatic amide and p-aminoaromatic amide can be conducted by reacting p-nitroaromatic amide or p-aminoaromatic amide with ammonia to produce the corresponding p-nitroaromatic amine or p-aminoaromatic amine, respectively, and the amide starting material which can be recycled. See for example, Jencks, W. P., *J. Am. Chem. Soc.*, Vol. 92, pp. 3201–3202 (1970). Preferably, p-nitroaromatic amide or p-aminoaromatic amide is reacted with ammonia in the presence of a solvent, e.g., methanol.

Embodiments $a_3$, $a_4$, $a_5$ and $a_6$

As used herein, the term "substituted aromatic azo compound" means a compound selected from the group consisting of compounds represented by the formula:

compounds represented by the formula:

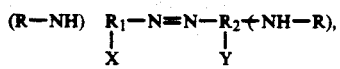

compounds represented by the formula:

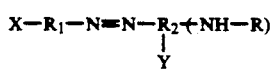

and mixtures thereof, wherein R—NH— represents a substituent derived from an amide or a substituted aromatic amine having at least two —$NH_2$ groups, $R_1$ is an aromatic group, $R_2$ is selected from the group consisting of aliphatic and aromatic groups, and X and Y are independently selected from the group consisting of hydrogen, halides, —$NO_2$, —$NH_2$, aryl groups, alkyl groups, alkoxy groups, —$SO_3$, —$SO_3R_{30}$, —$OR_{30}$, —$COOR_{30}$, and alkyl, aryl, aralkyl or alkaryl groups containing at least one —$NH_2$ group, wherein $R_{30}$ is as defined herein, halides are selected from the group consisting of chlorine, bromine and fluorine and $R_2$ is an aromatic group in substituted aromatic azo compounds (II) and (III). The substituted aromatic azo compounds of (I), (II) and (III) also includes azoxy or hydrazo derivatives thereof.

In the preparation of substituted aromatic azo compounds, the molar ratio of amide or substituted aromatic amine having at least two —$NH_2$ groups to X—$R_1$—N=N—$R_2$—Y or azoxy or hydrazo derivatives thereof can vary from a large excess of X—$R_1$—N=N—$R_2$—Y or azoxy or hydrazo derivatives thereof to a large excess of amide or substituted aromatic amine having at least two —$NH_2$ groups. Preferably, the reaction is conducted utilizing an excess of amide or substituted aromatic amine having at least two —$NH_2$ groups. More preferably, the molar ratio of amide or substituted aromatic amine having at least two —$NH_2$ groups to X—$R_1$—N=N—$R_2$—Y or azoxy or hydrazo derivatives thereof is at least about 1:1.

In the preparation of substituted aromatic amines by the reaction of a nucleophilic compound with a substituted aromatic azo compound, the molar ratio of a nucleophilic compound selected from the group consisting of aniline, substituted aniline derivatives, aliphatic amines, substituted aliphatic amine derivatives, amides and substituted aromatic amines having at least two —$NH_2$ groups to substituted aromatic azo compounds can vary from a large excess of substituted aromatic azo compound to a large excess of nucleophilic compound. Preferably, the reaction is conducted utilizing an excess of a nucleophilic compound as defined above. More preferably, the molar ratio of nucleophilic compound to substituted aromatic azo compound is at least about 1:1.

As used herein, the term "substituted aniline derivatives" means aniline containing one or more electron withdrawing or electron releasing substituents on the aromatic ring. Applicable substituents include, but are not limited to, halides, —$NO_2$, —$NH_2$, alkyl groups, alkoxy groups, —$SO_3$, —$SO_3R_{30}$, —$OR_{30}$, —$COOR_{30}$, and aryl, aralkyl or alkaryl groups containing at least 1 —$NH_2$ group wherein $R_{30}$ is as defined herein. Halides are selected from the group consisting of chloride, bromide or fluoride. The preferred alkyl and alkoxy groups contain from 1 to about 6 carbon atoms. The preferred aryl, aralkyl and alkaryl groups contain from about 6 to about 18 carbon atoms. Examples of substituted aniline derivatives include, but are not limited to, 2-methoxyaniline, 4-methoxyaniline, 4-chloroaniline, p-toluidine, 4-nitroaniline, 3-bromoaniline, 3-bromo-4-aminotoluene, p-aminobenzoic acid, 2,4-diaminotoluene, 2,5-dichloroaniline, 1,4-phenylenediamine, 4,4'-methylenedianiline, 1,3,5-triaminobenzene and mixtures thereof.

Aniline or substituted aniline derivatives can be added directly or can be formed in situ by addition of a compound that will form aniline or the corresponding aniline derivative under the conditions present in the reaction system.

Amides that can be employed according to the invention include aromatic amides, aliphatic amides, substituted aromatic amide derivatives, substituted aliphatic amide derivatives and diamides as defined herein.

Substituted aromatic amines having at least two —$NH_2$ groups that can be employed according to the invention are as defined herein.

Aliphatic amines and substituted aliphatic amines that can be employed according to the invention are compounds selected from the group consisting of compounds represented by the formula $Y'-R_{10}-NH-R_{11}-Y''$ and compounds represented by the formula:

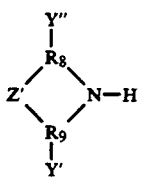

wherein $R_{10}$ is selected from the group consisting of alkyl, alkenyl, cycloalkyl and cycloalkenyl groups, $R_{11}$ is selected from the group consisting of a direct bond, alkyl, alkenyl, cycloalkyl and cycloalkenyl groups, $R_8$ and $R_9$ are independently selected from the group consisting of alkyl and alkenyl groups, $Z'$ is selected from the group consisting of a direct bond, $-NH-$, $-N-$, $-O-$ and $-S-$, and $Y'$ and $Y''$ are independently selected from the group consisting of hydrogen, halides, $-NO_2$, $-NH_2$, aryl groups, alkoxy groups, $-SO_2$, $-SO_3R_{30}$, $-OR_{30}$, $-COOR_{30}$, and alkyl, aryl, aralkyl or alkaryl groups containing at least one $-NH_2$ group wherein $R_{30}$ is as defined herein. Halides are selected from the group consisting of chloride, bromide and fluoride. The preferred aliphatic groups of $R_{10}$ and $R_{11}$ contain from 1 to about 12 carbon atoms. The preferred aryl, aralkyl and alkaryl groups contain from about 6 to about 18 carbon atoms. The preferred alkoxy groups contain from 1 to about 6 carbon atoms.

Examples of aliphatic amines and substituted aliphatic amine derivatives include, but are not limited to, cyclohexylamine, 2-butylamine, isopropylamine, 2-hexylamine, 2-heptylamine, 1,4-dimethylpentylamine, 1-methylheptylamine, 1-ethyl-3-methylpentylamine, 1,3-dimethylbutylamine, octylamine, piperidine, piperazine, hexamethylene diamine, methyl 6-aminohexanoate and mixtures thereof.

As used herein, the term "azo containing compounds" are compounds of the invention that are represented by the formula $X-R_1-N=N-R_2-Y$ or azoxy or hydrazo derivatives thereof wherein $R_1$ is an aromatic group, $R_2$ is selected from the group consisting of aliphatic and aromatic groups and X and Y are independently selected from the group consisting of hydrogen, halides, $-NO_2$, $-NH_2$, aryl groups, alkyl groups, alkoxy groups, $-SO_3$, $-SO_3R_{30}$, $-OR_{30}$, $-COOR_{30}$, and alkyl, aryl, aralkyl or alkaryl groups containing at least one $-NH_2$ group wherein $R_{30}$ is as defined herein. When $R_2$ is an aliphatic group, X is in the meta or ortho position on $R_1$. When $R_2$ is aromatic, at least one of X and Y is in the meta or ortho position on $R_1$ and $R_2$, respectively. Halides are selected from the group consisting of chloride, bromide and fluoride. The preferred aliphatic groups of $R_1$ and $R_2$ contain from 1 to about 12 carbon atoms and the preferred aromatic groups of $R_1$ and $R_2$ contain from about 6 to about 18 carbon atoms. The preferred alkyl and alkoxy groups contain from 1 to about 6 carbon atoms. The preferred aryl, aralkyl and alkaryl groups contain from about 6 to about 18 carbon atoms. Examples of azo containing compounds include, but are not limited to, azobenzene, substituted azobenzene derivative, azoxybenzene, 4-(phenylazo)diphenylamine, 1,2-diphenylhydrazine, and mixtures thereof.

As used herein, the term "substituted azobenzene derivatives" means azobenzene containing one or more electron withdrawing or electron releasing substituents on one or both of the aromatic rings. Applicable substituents include, but are not limited to, halides, $-NO_2$, $-NH_2$, alkyl groups, alkoxy groups, $-SO_3$, $-SO_3R_{30}$, $-OR_{30}$, $-COOR_{30}$, and aryl, aralkyl or alkaryl groups containing at least one $-NH_2$ group wherein $R_{30}$ is as defined herein. Halides are selected from the group consisting of chloride, bromide and fluoride. The preferred alkyl and alkoxy groups contain from 1 to about 6 carbon atoms. The preferred aryl, aralkyl, and alkaryl groups contain from about 6 to about 18 carbon atoms. Examples of substituted azobenzene derivatives include, but are not limited to, 3,4'-dichloroazobenzene, p-phenylazobenzene sulfonic acid, p-(2,4-dihydroxyphenylazo)benzene sulfonic acid, and mixtures thereof.

Suitable solvent systems include, but are not limited to, solvents such as dimethylsulfoxide, nucleophilic compounds such as substituted aniline derivatives, aniline and amides having a melting point below the reaction temperature, e.g., molten benzamide, dimethylformamide, N-methyl-2-pyrrolidone, pyridine, ethyleneglycoldimethyl ether, amines such as diisopropylethylamine, sec-butyl amine and 2-heptylamine, and the like, and mixtures thereof. As described in more detail below, solvent mixtures can be utilized wherein in one or more of the suitable solvents and another solvent, such as a controlled amount of a protic solvent, e.g., methanol or water, are combined.

Suitable bases are as defined herein for embodiments a, $a_1$ and $a_2$. Preferred materials for use as bases are alkali metal hydroxides, such as potassium hydroxide, alkali metal alkoxides such as potassium t-butoxide, alkali metal hydroxides or alkoxides in conjunction with a phase transfer catalyst such as potassium hydroxide in conjunction with crown ethers, and tetraalkylammonium hydroxides such as tetramethylammonium hydroxide or tetrabutylammonium hydroxide.

Preferably, the base is added to the amide, substituted aromatic amine having at least two $-NH_2$ groups or nucleophilic compound to produce a mixture which is then combined with the azo containing compound or substituted aromatic azo compound. Alternatively, the base can be added after the amide or nucleophilic compound and azo containing compound or substituted aromatic azo compound have been combined. Addition of materials can be above or below surface addition.

For the preparation of substituted aromatic azo compounds, the amount of base employed according to the invention can be conveniently expressed in terms of a molar ratio of suitable base to azo containing compound. Broadly, the molar ratio of base to azo containing compound will be about 1:1 to about 10:1, preferably about 1:1 to about 4:1, and most preferably about 1:1 to about 2:1.

For the preparation of substituted aromatic amines having at least two $-NH_2$ groups, the amount of base employed according to the invention can be conveniently expressed in terms of a molar ratio of suitable base to substituted aromatic azo compound. Broadly, the molar ratio of base to substituted aromatic azo compound will be about 1:1 to about 10:1, preferably about 1:1 to about 4:1, and most preferably, about 1:1 to about 2:1.

The reaction of the amide or substituted aromatic amine having at least two $-NH_2$ groups with the azo containing compound is conducted at a temperature within the range of from about 10° C. to about 150° C., such as from about 20° C. to about 120° C., preferably from about 30° C. to about 100° C. A most preferred temperature for conducting the reaction of the amide or substituted aromatic amine having at least two —NH$_2$ groups with the azo containing compound is from about 50° C. to about 90° C.

The reaction of the nucleophilic compound with the substituted aromatic azo compound is conducted at a temperature within the range of from about 70° C. to about 200° C., such as from about 70° C. to about 190° C., preferably from about 70° C. to about 180° C. A most preferred temperature for conducting the reaction of the nucleophilic compound with the substituted aromatic azo compound is from about 130° C. to about 170° C.

Control of the amount of protic material present in the reaction of the amide or substituted aromatic amine having at least two —NH$_2$ groups with the azo containing compound is important. The amount of protic material employed according to the invention can be conveniently expressed in terms of a molar ratio based on the amount of base present at the beginning of the reaction of amide or substituted aromatic amine having at least two —NH$_2$ groups and azo containing compound. Broadly, the molar ratio of protic material to base will be from 0:1 to about 5:1, preferably from 0:1 to about 3:1, and most preferably 0:1 to about 1:1. Thus, the present reaction could be conducted under anhydrous conditions. As used herein for the reaction of amide or substituted aromatic amine having at least two —NH$_2$ groups and azo containing compound in embodiments a$_3$ and a$_4$, the term "controlled amount" of protic material is an amount up to that which inhibits the reaction of amide with azo containing compound. The upper limit for the amount of protic material present in the reaction varies with the solvent. In addition, the amount of protic material tolerated will vary with the type of base, amount of base, and base cation, used in the various solvent systems. However, it is within the skill of one in the art, utilizing the teachings of the present invention, to determine the specific upper limit of the amount of protic material for a specific solvent, type and amount of base, base cation and the like. The minimum amount of protic material necessary to maintain selectivity of the desired products will also depend upon the solvent, type and amount of base, base cation and the like, that is utilized and can also be determined by one skilled in the art.

Control of the amount of protic material present in the reaction of the nucleophilic compound with the substituted aromatic azo compound is important. The amount of protic material employed according to the invention can be conveniently expressed in terms of a molar ratio based on the amount of base present at the beginning of the reaction of nucleophilic compound and substituted aromatic azo compound. Broadly, the molar ratio of protic material to base will be from 0:1 to about 5:1, preferably from 0:1 to about 1:1. Thus, the present reaction could be conducted under anhydrous conditions. As used herein for the reaction of nucleophilic compound and substituted aromatic azo compound in embodiments a$_5$ and a$_6$, the term "controlled amount" of protic material is an amount up to that which inhibits the reaction of nucleophilic compound with substituted aromatic azo compound. The upper limit for the amount of protic material present in the reaction varies with the solvent. In addition, the amount of protic material tolerated will vary with the type of base, amount of base, and base cation, used in the various solvent systems. However, it is within the skill of one in the art, utilizing the teachings of the present invention, to determine the specific upper limit of the amount of protic material for a specific solvent, type and amount of base, base cation and the like. The minimum amount of protic material necessary to maintain selectivity of the desired products will also depend upon the solvents, type and amount of base, base cation and the like, that is utilized and can also be determined by one skilled in the art.

Since the amount of protic material present in the reaction is important, it is possible to reduce the amount of protic material present as much as possible and then add back to the reaction the desired amount. Protic materials that can be utilized to add back to the reaction are known to those skilled in the art and include, but are not limited to, water, methanol and the like, and mixtures thereof. Methods for measuring the amount of protic material and for reducing the amount of protic material as much as possible are well known in the art. For example, the amount of water present in certain reagents can be determined by utilizing a Karl-Fischer apparatus, and the amount of water can be reduced through distillation and/or drying under reduced pressure, drying in the presence of P$_2$O$_5$ and other agents, azeotropic distillation utilizing, for example, xylene, and the like, including combinations thereof.

In one embodiment for controlling the amount of protic material during the reaction of amide, substituted aromatic amine having at least two —NH$_2$ groups or nucleophilic compound with azo containing compound or substituted aromatic azo compound, a desiccant is added so as to be present during the reaction of amide, substituted aromatic amine having at least two —NH$_2$ groups or nucleophilic compound with azo containing compound or substituted aromatic azo compound. For example, when the protic material is water, the desiccant removes water present during the reaction of amide, substituted aromatic amine having at least two —NH$_2$ groups or nucleophilic compound and azo containing compound or substituted aromatic azo compound and results in higher conversion of azo containing compound or substituted aromatic azo compound and yields of substituted aromatic azo compound or substituted aromatic amine having at least two —NH$_2$ groups. As used herein, desiccant is a compound present during the reaction of amide, substituted aromatic amine having at least two —NH$_2$ groups or nucleophilic compound and azo containing compound or substituted aromatic azo compound in addition to the suitable base used. Examples of suitable desiccants include, but are not limited to, anhydrous sodium sulfate, molecular sieves, such as types 4A, 5A, and 13X available from the Union Carbide Corporation, calcium chloride, tetramethylammonium hydroxide dihydrate, anhydrous bases such as KOH and NaOH, and activated alumina.

In another embodiment for controlling the amount of protic material during the reaction of amide, substituted aromatic amine having at least two —NH$_2$ groups or nucleophilic compound and azo containing compound or substituted aromatic azo compound, protic material is continuously removed from the reaction mixture by distillation. If the protic material present forms an azeotrope with one of the compounds in the reaction mixture, the protic material can be removed by continuous azeotropic distillation of protic material utilizing the azeotrope. The continuous removal of protic material allows the use of lower amounts of base in the reaction of amide or nucleophilic compound and azo containing compound or substituted aromatic azo compound while achieving very high conversion of azo containing compound or substituted aromatic azo compound and excellent yields of substituted aromatic azo compound or substituted aromatic amine having at least two —NH$_2$ groups.

Generally, the reactions can be conducted under aerobic or anaerobic conditions. When the nucleophilic compound is a secondary aliphatic amine, the reactions can be conducted only under aerobic conditions, i.e., under anaerobic conditions the only applicable aliphatic amines or substituted aliphatic amine derivatives are those having the formula Y'—R$_{10}$—NH$_2$. Under aerobic conditions the reaction is conducted essentially as described above in the reaction zone which is exposed to oxygen, usually by exposure to air. Under aerobic conditions, the pressure at which the reaction is conducted can vary and the optimal pressure, as well as the optimal combination of pressure and temperature, are easily determined by one skilled in the art. For example, the reaction can be conducted at a pressure ranging from about 10 psig to about 250 psig, such as from about 14 psig to about 150 psig. Under anaerobic conditions, the reactions can be conducted at atmospheric pressure or reduced or elevated pressures, in the presence of an inert gas such as, for example, nitrogen or argon. Optimal conditions for a particular set of reaction parameters, such as temperature, base, solvent and the like, are easily determined by one skilled in the art utilizing the teaching of the present invention.

Aminolysis of substituted aromatic amines containing an aromatic amide bond, which are prepared by reacting an amide and an azo containing compound to produce a substituted aromatic azo compound followed by reacting the substituted aromatic azo compound with a nucleophilic compound, can be conducted by reacting the substituted aromatic amine with ammonia to produce the corresponding substituted aromatic amine having at least two —NH$_2$ groups and an amide which can be recycled. See for example, Jencks, W. P., *J. Am. Chem. Soc.*, Vol. 92, pp. 3201-3202 (1970). Preferably, the substituted aromatic amine containing an aromatic amide bond is reacted with ammonia in the presence of a solvent, e.g., methanol.

Embodiment a$_7$

The products of the reaction of substituted aniline derivative and nitrobenzene, i.e., the 4-nitro and/or 4-nitroso products, can be in the form of the neutral compound, i.e., not in the form of a salt, and/or in the form of the salt. The salt is produced in the reaction mixture from reaction of the 4-nitro and/or 4-nitroso products with the base. Thus, the reaction mixture produced in the process for reacting substituted aniline derivative with nitrobenzene can include the neutral compound, or salts or mixtures thereof depending on the specific reaction conditions selected.

The molar ratio of substituted aniline derivatives to nitrobenzene can vary from a large excess of nitrobenzene to a large excess of substituted aniline derivative. Preferably, the reaction is conducted utilizing an excess of substituted aniline derivative.

As used herein, the term "substituted aniline derivatives" means aniline containing one or more electron withdrawing or electron releasing substituents on the aromatic ring provided at least one substituent is selected from the group consisting of —NO$_2$, —NH$_2$ and aryl, aralkyl or alkaryl groups containing at least one —NH$_2$ group. Applicable substituents include, but are not limited to, halides, —NO$_2$, —NH$_2$, alkyl groups, alkoxy groups, —SO$_3$, —COOR$_{30}$ and aryl, aralkyl or alkaryl groups containing at least one —NH$_2$ group wherein R$_{30}$ is as defined herein. Halides are selected from the group consisting of chloride, bromide and fluoride. The preferred alkyl and alkoxy groups contain from 1 to about 6 carbon atoms. The preferred aryl, aralkyl and alkaryl groups contain from about 6 to about 18 carbon atoms. Examples of substituted aniline derivatives include, but are not limited to, 4-nitroaniline, 2,4-diaminotoluene, 1,4-phenylene diamine, 4,4'-methylene dianiline, 1,3,5-triaminobenzene and mixtures thereof.

Substituted aniline derivatives can be added directly or can be formed in situ by addition of a compound that will form the corresponding aniline derivative under the conditions present in the reaction system.

Suitable solvent systems include, but are not limited to, solvents such as, for example, dimethylsulfoxide, N-methyl-2-pyrrolidone, dimethylformamide, pyridine, nitrobenzene, nonpolar hydrocarbon solvents such as toluene and hexane, ethyleneglycol dimethyl ether, diisopropyl ethylamine, and the like, as well as mixtures thereof. As described in more detail below, solvent mixtures can be utilized wherein one or more of the suitable solvents and another solvent, such as a controlled amount of a protic solvent, e.g., methanol, are combined.

Suitable bases are as defined herein for embodiments a, a$_1$ and a$_2$. Preferred materials (bases) for use as bases are tetraalkylammonium hydroxides such as tetramethylammonium hydroxide. Preferably, the base is added to the substituted aniline derivative to produce a mixture which is then combined with the nitrobenzene. Alternatively, the base can be added after the substituted aniline derivative and nitrobenzene have been combined. Addition of materials can be above or below surface addition. The amount of base utilized in the present process can vary over a wide range. For example, the reaction can be conducted in a manner which is limiting in base or the reaction can be conducted in a manner which is limiting in nitrobenzene or substituted aniline derivative depending, among other factors, on the desired degree of minimization of azobenzene.

The reaction is conducted at a suitable temperature which can vary over a wide range. For example, the temperature can fall within a range of from about $-10°$ C. to about 150° C., such as from about 0° C. to about 100° C., preferably from about 10° C. to about 90° C. A most preferred temperature for conducting the reaction of the present invention is from about 60° C. to about 80° C., such as at 75° C. Where production of azobenzene is not a problem, higher temperatures will be suitable. However, where it is desired to minimize the amount of azobenzene, lower temperatures or anaerobic reaction conditions are more suitable.

Control of the amount of protic material present in the reaction of substituted aniline derivative and nitrobenzene is important. The amount of protic material employed according to the invention can be conveniently expressed in terms of a molar ratio based on the amount of base present at the beginning of the reaction of substituted aniline derivative and nitrobenzene. Broadly, the molar ratio will be less than about 6:1, preferably less than about 4:1, and more preferably less than about 2:1. Thus, the present reaction could be conducted under anhydrous conditions. As used herein for embodiment a7, a "controlled amount" of protic material is an amount up to that which inhibits the reaction of substituted aniline derivative with nitrobenzene. The upper limit for the amount of protic material present in the reaction varies with the solvent. In addition, the amount of protic material tolerated will vary with type of base, amount of base, and base cation, used in the various solvent systems. However, it is within the skill of one in the art, utilizing the teachings of the present invention, to determine the specific upper limit of the amount of protic material for a specific solvent, type and amount of base, base cation and the like. The minimum amount of protic material necessary to maintain selectivity of the desired products will also depend on the solvent, type and amount of base, base cation and the like, that is utilized and can also be determined by one skilled in the art.

Since the amount of protic material present in the reaction is important, it is possible to reduce the amount of protic material present as much as possible and then add back to the reaction the desired amount. Protic materials that can be utilized to add back to the reaction are known to those skilled in the art and include, but are not limited to, water, methanol and the like. Methods for measuring the amount of protic material and for reducing the amount of protic material as much as possible are well known in the art. For example, the amount of water present in certain reagents can be determined by utilizing a Karl-Fischer apparatus, and the amount of water can be reduced through distillation and/or drying under reduced pressure, drying in the presence of $P_2O_5$ and other agents, azeotropic distillation, and the like, including combinations thereof.

In one embodiment for controlling the amount of protic material during the reaction of substituted aniline derivatives and nitrobenzene, a desiccant is added so as to be present during the reaction of substituted aniline derivative and nitrobenzene. For example, when the protic material is water, the desiccant removes water present during the reaction of substituted aniline derivatives and nitrobenzene and results in higher conversion of nitrobenzene. As used herein, desiccant is a compound present during the reaction of substituted aniline derivatives and nitrobenzene in addition to the suitable base used. Examples of suitable desiccants include, but are not limited to, anhydrous sodium sulfate, molecular sieves such as types 4A, 5A and 13X available from the Union Carbide Corporation, calcium chloride, tetramethyl ammonium hydroxide dihydrate, anhydrous bases such as KOH and NaOH, and activated alumina.

In another embodiment for controlling the amount of protic material during the reaction of substituted aniline derivatives and nitrobenzene, protic material is continuously removed from the reaction mixture by distillation. If the protic material forms an azeotrope with one of the compounds in the reaction mixture, the protic material can be removed by continuous azeotropic distillation utilizing the azeotrope. The continuous distillation of protic material is the currently preferred method for controlling the amount of protic material present during the reaction of substituted aniline derivatives and nitrobenzene. The continuous removal of protic material allows the use of lower amounts of base in the reaction of substituted aniline derivatives and nitrobenzene while achieving very high conversion of nitrobenzene.

The reaction can be conducted under aerobic or anaerobic conditions. Under aerobic conditions, the reaction is conducted essentially as described above in a reaction zone which is exposed to oxygen, usually by exposure to air. Under aerobic conditions, the pressure at which the reaction is conducted can vary and the optimal pressure, as well as the optimal combination of pressure and temperature/pressure conditions, are easily determined by one skilled in the art. For example, the reaction can be conducted at room temperature and at a pressure ranging from about 10 psig to about 250 psig, such as from about 14 psig to about 150 psig. Under anaerobic conditions, the reaction can be conducted at atmospheric pressure or reduced or increased pressures, in the presence of a neutral gas such as, for example, nitrogen or argon. Optimal conditions for a particular set of reaction parameters, such as temperature, base, solvent and the like, are easily determined by one skilled in the art utilizing the teachings of the present invention. It has been observed that less azobenzene is produced when the reaction is conducted aerobically with DMSO, and other similar solvents, as the solvent.

The products of the reaction of substituted aniline derivatives and nitrobenzene and/or their salts can be reduced to substituted aromatic amine having at least two $-NH_2$ groups. The neutral compounds can be generated from the salts utilizing water and/or an acid. Alternatively, the salts can be reduced. This reduction can be carried out by any of many known reductive processes, such as using a hydride source, e.g., sodium borohydride in conjunction with palladium- or platinum-on-carbon catalyst. Preferably, this reduction is conducted by a catalytic reduction wherein hydrogenation is effected under hydrogen pressure in the presence of platinum- or palladium-on-carbon, nickel, and the like. This hydrogenation process is described in detail in "Catalytic Hydrogenation in Organic Synthesis", P. N. Rylander, Academic Press, N.Y., p. 299 (1979), which is hereby incorporated herein by reference. The hydrogenation can be conducted in a variety of solvents including, but not limited to, toluene, xylene, aniline, water and mixtures thereof. Preferably, the hydrogenation is conducted utilizing a platinum-on-carbon or palladium-on-carbon catalyst in a suitable solvent such as, for example, either toluene, xylene or aniline, mixtures thereof, or mixtures which include water as the solvent and a hydrogen pressure of from 100 psig $H_2$ to about 340 psig $H_2$ at a temperature of about 80° C.

PREPARATION OF ISOCYANATES AND CARBAMATE ESTERS

Examples of isocyanates having at least two $-N\!\!=\!\!C\!\!=\!\!O$ groups include, but are not limited to, 1,4-phenylene diisocyanate, 4,4'-diisocyanatodiphenylamine, 4,4'-diisocyanatobenzanilide, 4-isocyanato-4'-(p-phenylisocyanato)diphenylamine, and mixtures thereof.

Examples of carbamate esters having at least two

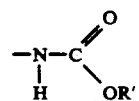

groups include, but are not limited to, 1,4-phenylene-bis(phenylmethyl) carbamate, 1,4-phenylene-bis (ethyl) carbamate, 4,4'-dibenzylcarbamatobenzanilide, 4,4'- dibenzylcarbamato diphenylamine, and mixtures thereof.

In either the production of isocyanates or the production of carbamate esters according to the invention, the ammonium carbamate salt produced by the reaction of $CO_2$ with the substituted aromatic amine having at least two $-NH_2$ groups can be utilized directly as produced or it can be recovered prior to further reaction with either the electrophilic or oxophilic dehydrating agent or the primary or secondary hydrocarbyl halide.

Embodiment c

The ammonium salt of the carbamate anion is prepared in solution in the presence of an organic, nitrogenous base. The reaction between the primary amine and carbon dioxide to form the ammonium carbamate salt may be represented by the equation (1) wherein $H_2N-R-NH_2$ represents a substituted aromatic amine having at least two $-NH_2$ groups. The resulting ammonium carbamate salt solutions are normally homogeneous.

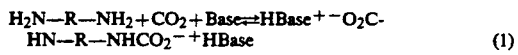
(1)

The result of the reaction of the ammonium carbamate salt with the electrophilic or oxophilic dehydrating agent may be represented by the equation (2) wherein $O=C=N-R-N=C=O$ represents an isocyanate having at least two $-N=C=O$ groups.

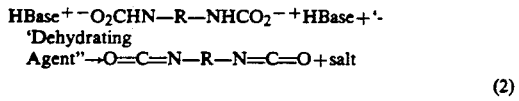
(2)

Applicable solvents for use in the process of the invention are aprotic organic solvents. While both polar and non-polar aprotic organic solvents, as well as mixtures thereof, may be used, it is currently preferred to use non-polar aprotic organic solvents due to reduced occurrence of side reactions. As utilized herein, the phrase polar aprotic organic solvent means an aprotic organic solvent having a dielectric constant measured at 25° C. of greater than about 10 ε as reported in Reichardt, C., Solvents and solvent effects in organic chemistry, 2nd ed., VCH Verlagsgesellschaft, Weinheim, (1988), Table A-1, utilizing toluene (2.38 ε) and tetrahydrofuran (7.58 ε) as standards measured at 25° C. Other methods for determining dielectric constants are known and suitable polar aprotic organic solvents are those having a dielectric constant greater than that of tetrahydrofuran utilizing any of such methods.

Examples of non-polar aprotic organic solvents which can be employed in the process of the invention include dichloromethane, toluene, tetrahydrofuran, o-dichlorobenzene, triethylamine and the like, and mixtures thereof. Currently preferred non-polar aprotic organic solvents include dichloromethane and toluene.

Examples of polar aprotic organic solvents which can be employed in the process of the invention include dimethyl formamide, N-methyl-2-pyrrolidone, N,N-dimethyl acetamide, dimethyl sulfoxide, acetonitrile, sulfolane, pyridine and the like, and mixtures thereof. Currently preferred polar aprotic organic solvents include acetonitrile and N,N-dimethyl acetamide.

Although not specifically required, it is preferred to utilize the same solvent to carry out both reaction steps of the present invention in order to avoid additional process equipment for recovering additional solvents.

Preferably, the amount of solvent utilized in the process of the invention is at least the amount necessary to solubilize the ammonium carbamate salt present.

To obtain high selectivities and yields for the desired isocyanates, an organic, nitrogenous base is employed as the base in the process of the invention. The phrase "organic, nitrogenous base" as used herein for embodiment c refers to a base utilized in addition to the reactant substituted aromatic amine having at least two $-NH_2$ groups. Applicable organic, nitrogenous bases for use in the process of the invention include guanidine compounds, amidine compounds, phosphazene compounds, tertiary amines, pyridine and mixtures of any two or more thereof.

The phosphazene compounds of the invention are compounds represented by the formula:

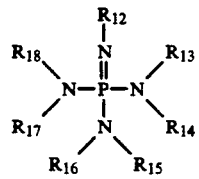

wherein $R_{12}$, $R_{13}$, $R_{14}$, $R_{15}$, $R_{16}$, $R_{17}$ and $R_{18}$ are independently selected from the group consisting of alkyl, aryl, alkaryl, aralkyl and cycloalkyl radicals having 1 to about 22 carbon atoms; or one of $R_{13}$ or $R_{14}$ together with one of $R_{15}$ or $R_{16}$, one of $R_{17}$ or $R_{18}$ together with one of $R_{15}$ or $R_{16}$, and $R_{12}$ together with one of $R_{13}$ or $R_{14}$ or one of $R_{17}$ or $R_{18}$ independently form a nitrogen-containing heterocycle; or $R_{13}$ together with $R_{14}$, $R_{15}$ together with $R_{16}$, and $R_{17}$ together with $R_{18}$ independently represent a radical represented by the formula:

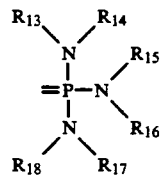

wherein $R_{13}$, $R_{14}$, $R_{15}$, $R_{16}$, $R_{17}$ and $R_{18}$ are as defined above.

The guanidine compounds of the invention are compounds represented by the formula:

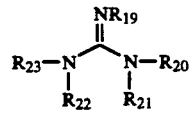

wherein $R_{19}$, $R_{20}$, $R_{21}$, $R_{22}$ and $R_{23}$ are independently selected from the group Consisting of alkyl, aryl, alkaryl, aralkyl and cycloalkyl radicals having 1 to about 22 carbon atoms; or $R_{19}$ together with one of $R_{20}$, $R_{21}$, $R_2$ or $R_{23}$, $R_{20}$ and $R_{21}$, and $R_{22}$ and $R_{23}$ independently form a nitrogen-containing heterocycle.

The amidine compounds of the invention are compounds represented by the formula:

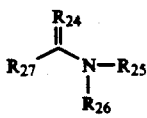

wherein $R_{24}$, $R_{25}$, $R_{26}$ and $R_{27}$ are independently selected from the group consisting of alkyl, aryl, alkaryl, aralkyl and cycloalkyl radicals having 1 to about 22 carbon atoms; or $R_{24}$ together with $R_{25}$ or $R_{26}$ and $R_{27}$ together with $R_{25}$ or $R_{26}$ independently form a nitrogen-containing heterocycle.

Examples of organic, nitrogenous bases which can be employed in the process of the invention include triethylamine, diethyl isopropylamine, trimethylamine, pyridine, tetramethyl guanidine (TMG), cyclohexyltetramethyl guanidine (CyTMG), butyltetraethyl guanidine (n-BTEG), cyclohexyl-tetraethyl guanidine (CyTEG), tetraethyl guanidine (TEG), t-butyl-tetraethyl guanidine (t-BTEG), 7-methyl-1,5,7-triazabicyclo[4.4.0]dec-5-ene (MTBD), t-butyl-dimethyl formamidine (t-BDMF), t-butyldimethyl acetamidine (t-BDMA), 1,5-diazabicyclo[4.3.0]non-5-ene (DBN), 1,8-diazabicyclo[5.4.0]undec-7-ene (DBU), t-butyliminotris(dimethylamino) phosphorane ($P_1$-tBu), 1-t-butyl-4,4,4-tris(dimethylamino)-2,2-bis-tris(dimethylamino)-phosphoranylideneamino-$2\lambda,4\lambda$-catenadi(phosphazene) ($P_4$-tBu), 2-t-butylimino-2-diethylamino-1,3-dimethyl-perhydro-1,3,2-diazaphosphorane (BEMP), t-butyliminotris(diethylamino)phosphorane, 2-t-octylimino-2-diethylamino-1,3-dimethyl perhydro-1,3,2-diazaphosphorane, and the like, and mixtures of any two or more thereof.

The preferred organic, nitrogenous base will depend on the electrophilic or oxophilic dehydrating agent used. Generally, when the electrophilic or oxophilic dehydrating agent is not a halogencontaining compound, the preferred base is a guanidine, phosphazene or amidine compound or if a mixture of bases is used, at least one base of the mixture of bases is preferably a guanidine, phosphazene or amidine compound. When the electrophilic or oxophilic dehydrating agent is phosphorus pentoxide, the preferred base includes an aliphatic tertiary amine.

The amount of organic, nitrogenous base utilized in the process of the invention will depend upon the particular embodiment of the process.

In the embodiment where the ammonium carbamate salt is not recovered prior to reaction with the electrophilic or oxophilic dehydrating agent, the amount of organic, nitrogenous base can be conveniently expressed in terms of a ratio based on the number of equivalents of amine in the substituted aromatic amine having at least two —$NH_2$ groups charged. Broadly, the ratio of the number of moles of organic, nitrogenous base to the number of equivalents of amine in the substituted aromatic amine will be about 1:1 to about 20:1, preferably about 2:1 to about 10:1, and most preferably about 2:1 to about 4:1. The organic, nitrogenous base can be completely charged at the beginning of the process, or a portion may be charged at the beginning of the process and the remainder charged at any time prior to the reaction of the ammonium carbamate salt with the electrophilic or oxophilic dehydrating agent.

In the embodiment where the ammonium carbamate salt is recovered prior to reaction with the electrophilic or oxophilic dehydrating agent, the amount of organic, nitrogenous base can be conveniently expressed in terms of a ratio based on the number of equivalents of amine in the substituted aromatic amine having at least two —$NH_2$ groups charged for the reaction of the substituted aromatic amine with carbon dioxide, and the amount of organic, nitrogenous base can be conveniently expressed in terms of a ratio based on the number of equivalents of carbamate in the ammonium carbamate salt charged for the reaction of the ammonium carbamate salt with the electrophilic or oxophilic dehydrating agent. For the reaction of the substituted aromatic amine having at least two —$NH_2$ groups with carbon dioxide, the ratio of the number of moles of organic, nitrogenous base to the number of equivalents of amine in the substituted aromatic amine will broadly be about 0.5:1 to about 10:1, preferably about 1:1 to about 5:1, and most preferably about 1:1 to about 2:1. For the reaction of the ammonium carbamate salt with the electrophilic or oxophilic dehydrating agent, the ratio of the number of moles of organic, nitrogenous base to the number of equivalents of carbamate in the ammonium carbamate salt will broadly be about 0.5:1 to about 10:1, preferably about 1:1 to about 5:1, and most preferably about 1:1 to about 2:1.

Applicable electrophilic or oxophilic dehydrating agents for use in the process of the invention include $POX'_3$, $PX'_3$, $SOX'_2$, $SO_2X'_2$, $SO_3$, $PX'_5$, $P_2O_5$, $NO_y$, $NOX'$, ketene, acid anhydrides having the formula

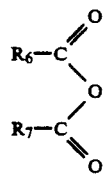

acid halides having the formula

and halides or oxyhalides of metals selected from the group consisting of transition metals, Group III B metals, Group IV B metals, and Group V B metals, and mixtures thereof wherein $R_6$ and $R_7$ are independently selected from the group consisting of fluoroalkyl, alkyl, aryl, alkaryl and aralkyl radicals having 1 to about 22 carbon atoms, X' is chlorine or bromine, halides are chlorides or bromides, and y is 1 or 2. The periodic table nomenclature used herein is that of the International Union of Pure and Applied Chemistry (IUPAC).

Examples of suitable electrophilic or oxophilic dehydrating agents include $POCl_3$, $PCl_3$, $PBr_3$, $SOCl_2$, $PCl_5$, $P_2O_5$, NO, $NO_2$, NOCl, $AlCl_3$, $VOCl_3$, $AlBr_3$, $TiBr_4$, $BBr_3$ and $TiCl_4$.

Examples of acid anhydrides which can be employed in the process of the invention include acetic anhydride, benzoic anhydride, propionoic anhydride, trifluoroacetic anhydride, and the like, and mixtures thereof. The currently preferred acid anhydride is trifluoroacetic anhydride.

Examples of acid halides which can be employed in the process of the invention include acetyl chloride, acetyl bromide, benzoyl chloride, propionyl chloride, and the like, and mixtures thereof. The currently preferred acid halide is acetyl chloride.

The currently preferred electrophilic or oxophilic dehydrating agents are $POCl_3$, $PCl_3$ and $SOCl_2$ because of the extremely high yields achievable with these compounds under mild reaction conditions. However, when halide containing electrophilic or oxophilic dehydrating agents are used, halide salts are generated and must be handled as a waste byproduct. The formation of halide salt byproduct can be avoided if a non-halide containing electrophilic or oxophilic dehydrating agent, such as acetic anhydride, $P_2O_5$ or $SO_3$, is used. When phosphorus pentoxide is used as the dehydrating agent, extremely high yields are achievable under mild reaction conditions when the base is an aliphatic tertiary amine or a mixture containing an aliphatic tertiary amine.

In the embodiment where the ammonium carbamate salt is not recovered prior to reaction with the electrophilic or oxophilic dehydrating agent, the amount of electrophilic or oxophilic dehydrating agent can be conveniently expressed in terms of a ratio based on the number of equivalents of amine in the substituted aromatic amine having at least two $-NH_2$ groups charged. Broadly, the ratio of the number of moles of electrophilic or oxophilic dehydrating agent to the number of equivalents of amine in the substituted aromatic amine will be about 0.4:1 to about 10:1, preferably about 0.9:1 to about 5:1 and most preferably about 1:1 to about 2:1.

In the embodiment where the ammonium carbamate salt is recovered prior to reaction with the electrophilic or oxophilic dehydrating agent, the amount of electrophilic or oxophilic dehydrating agent can be conveniently expressed in terms of a ratio based on the number of equivalents of carbamate in the ammonium carbamate salt charged for the reaction of the ammonium carbamate salt with the electrophilic or oxophilic dehydrating agent. Broadly, the ratio of the number of moles of electrophilic or oxophilic dehydrating agent to the number of equivalents of carbamate in the ammonium carbamate salt will be about 0.4:1 to about 10:1, preferably about 0.9:1 to about 5:1, and most preferably about 1:1 to about 2:1.

The reaction between the substituted aromatic amine having at least two $-NH_2$ groups and carbon dioxide is conducted under a $CO_2$ atmosphere. The pressure of $CO_2$ during this reaction is 0 psig (atmospheric pressure) to about 150 psig, preferably 0 psig to about 100 psig, and most preferably 0 psig to about 80 psig. It is preferred to charge the $CO_2$ to the reaction vessel containing the primary amine below the liquid level in the reaction vessel. Although not specifically required, it is preferred to conduct the reaction of ammonium carbamate salt with electrophilic or oxophilic dehydrating agent under a $CO_2$ atmosphere. However, the reaction of ammonium carbamate salt with electrophilic or oxophilic dehydrating agent can be conducted under any inert atmosphere, e.g. nitrogen, argon or air, provided the atmosphere is substantially dry. A substantially dry atmosphere is critical because water will react with the electrophilic or oxophilic dehydrating agent. The pressure during this reaction is 0 psig to about 150 psig, preferably 0 psig to about 100 psig, and most preferably 0 psig to about 80 psig.

The temperature and time used in the process of the invention will depend on the particular reaction involved. For the reaction of substituted aromatic amine having at least two $-NH_2$ groups with $CO_2$, the temperature is about $-78°$ C. to about $100°$ C., preferably about $10°$ C. to about $40°$ C., and most preferably about $20°$ C. to about $30°$ C. The time will broadly be the time required to achieve complete mixing of reactants to about 4 hours, preferably about 5 minutes to about 1 hour, and most preferably about 10 minutes to about 30 minutes. For the reaction of ammonium carbamate salt with electrophilic or oxophilic dehydrating agent, the temperature is about $-78°$ C. to about $100°$ C., preferably about $-20°$ C. to $30°$ C., and most preferably about $-10°$ C. to about $10°$ C. The time will broadly be the time required to achieve complete mixing of the reactants to about 4 hours, preferably about 1 minute to about 30 minutes, and most preferably about 5 minutes to about 10 minutes.

For the embodiment where the ammonium carbamate salt is recovered prior to reaction with the electrophilic or oxophilic dehydrating agent, the ammonium carbamate salt can be recovered by any conventional means known in the art.

The desired isocyanates produced by the process of the invention can be recovered by any conventional means known in the art, such as that disclosed in the examples herein.

Embodiment $c_1$

The ammonium salt of the carbamate anion is prepared in solution in the presence of the organic, nitrogenous base selected from the group consisting of guanidine compounds, phosphazene compounds, amidine compounds and mixtures thereof. The use of a base shifts the equilibrium toward the production of the carbamate anions. Where the reaction between the substituted aromatic amine having at least two $-NH_2$ groups is carried out in the presence of a base, the reaction may be represented by the equation (1) wherein $H_2N-R-NH_2$ represents a substituted aromatic amine having at least two $-NH_2$ groups. The resulting ammonium carbamate salt solutions are normally homogeneous.

Equation (2) shows the results of the addition of the carbamate anion to a hydrocarbyl halide wherein $R'-O_2CHN-R-NHCO_2-R'$ represents a carbamate ester having at least two

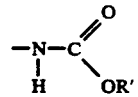

groups

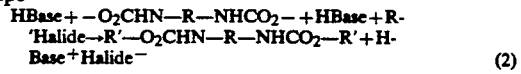

(2)

In order to conduct the reaction with reasonable rates and commercially practicable yields, addition of the carbamate anion to the hydrocarbyl halide is performed in a polar aprotic solvent. Normally, the reaction, when conducted in a polar aprotic solvent, proceeds smoothly under mild conditions, e.g. at $25°$ C. and 110 psi carbon dioxide pressure, to give the corresponding product in high yields.

An advantage of the present process is that the reaction between the substituted aromatic amine having at least two $-NH_2$ groups and $CO_2$ proceeds under mild temperature and pressure. Room temperature and a pressure of 110 psi $CO_2$ are suitable and are preferred. However, if desired, the reaction can be carried out between about 25° C. and about 150° C. under a $CO_2$ pressure in a range of from about 2 psi to about 400 psi, such as from about 10 psi to about 200 psi. A preferred temperature range is from about 30° C. to about 125° C., such as from about 35° C. to about 80° C.

Primary or secondary hydrocarbyl halides suitable for use in the present invention can be represented by the formula R'X" or X"R'X" wherein R' represents alkyl, alkenyl, cycloalkyl, cycloalkenyl, aralkyl and aralkenyl radicals having from 1 to about 22 carbon atoms, provided that R' is not a tertiary radical of the formula $(R)_3C-$ or $(R)_2C=C(R)-$ and X" represents Cl, Br, I and F. Examples of such hydrocarbyl halide include alkyl, cycloalkyl, alkenyl, aralkyl halides. Specific examples of such halides include methyl chloride, methyl iodide, ethyl bromide, n-butyl bromide, n-butyl chloride, iso-butyl chloride, amyl chloride, n-octyl chloride, benzyl bromide, benzyl chloride, (2-naphthyl)methyl chloride, 3-chlorocyclohexene, chlorocyclohexane, 2-methyl allyl chloride, 4-chloro-2-butene and the like. Hydrocarbyl dihalides and polyhalides may also be used. For example, 1,4-dichloro-2-butene, 1,4-dichlorobutane, dichloro-p-xylene, and the like, may be utilized. The present invention is also applicable to formation of cyclic carbamates and carbonates wherein a suitable alcohol or amine, as described above, containing a suitable leaving group such as a halide is reacted with $CO_2$ as set forth herein, in the presence of an organic nitrogenous base selected from the group consisting of guanidine compounds, phosphazene compounds, amidine compounds and mixtures thereof.

The reaction between the salt and the hydrocarbyl halide is carried out in a suitable polar aprotic organic solvent. As utilized herein, the phrase "polar aprotic organic solvent" means an aprotic organic solvent having a dielectric constant of greater than about 10 $\epsilon$ as reported in Reichardt, C., "Solvents and Solvent Effects in Organic Chemistry," 2nd ed., VCH Verlagsgesellschaft, Weinheim, (1988), Table A-1, utilizing toluene (2.38 $\epsilon$) and tetrahydrofuran (7.58 $\epsilon$), both at 20° C., as standards. Other methods for determining dielectric constants are known and suitable solvents are those having a dielectric constant greater than that of tetrahydrofuran utilizing any of such methods. Examples of suitable solvents include acetonitrile, N-methyl pyrrolidone, dimethylformamide, dimethylsulfoxide, and the like, as well as mixtures thereof. Preferred solvents are acetonitrile and DMSO. Although not specifically required, it is preferred to utilize these same solvents to carry out the reaction between the amine or alcohol and carbon dioxide in order to avoid the step of isolating the salt. However, this reaction can also be conducted in other organic solvents which are not polar aprotic solvents, such as, for example, THF, methylene chloride and the like.

To obtain high selectivity for carbamate esters over amine products (oxygen vs. nitrogen attack), the anion is stabilized by the use of an essentially stoichiometric amount of an organic nitrogenous base. The phrase "organic, nitrogenous base" as used herein for embodiment $c_1$ refers to a base utilized in addition to the reactant substituted aromatic amine having at least two $-NH_2$ groups. Applicable organic, nitrogenous bases for use in the process of the invention for embodiment $c_1$ include guanidine compounds, amidine compounds, phosphazene compounds and mixtures of any two or more thereof. The phosphazene, guanidine and amidine compounds are as defined above in embodiment c. Addition of a recovered carbamate anion under carbon dioxide pressure to a solution of a hydrocarbyl halide in a suitable polar aprotic solvent gives high yields and selectivities of urethanes and carbonates and with high rates. The selection of the base in the formation of the carbamate or carbonate is important in order to obtain higher selectivities and thus higher yields.

The amount of organic, nitrogenous base can be conveniently expressed in terms of a ratio based on the number of equivalents of amine in the substituted aromatic amine having at least two $-NH_2$ groups charged. Broadly, the ratio of the number of moles of organic, nitrogenous base to the number of equivalents of substituted aromatic amine having at least two $-NH_2$ groups will be about 1:1 to about 10:1, preferably about 1:1 to about 1.5:1, and most preferably about 1:1. The rate of reaction between the carbamate salts and the hydrocarbyl halide can be increased by utilizing excess, up to about 2 moles per mole of carbamate, hydrocarbyl halide. It is believed that use of such excess hydrocarbyl halide facilitates reaction conditions which are pseudo-first order as opposed to second order. Thus, in order to render the present process more commercially practicable, it is preferred to use an excess of such hydrocarbyl halide.

In the embodiment wherein an isocyanate having at least two $-N=C=O$ groups is the desired product, the carbamate ester having at least two

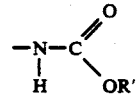

groups may be subjected to conditions sufficient to crack the carbamate ester to the isocyanate. This cracking can be carried out by any of many known processes such as thermal cracking or pyrolysis.

It is known that an isocyanate can be obtained via the thermal cracking of a carbamate ester. Several such processes are set forth in U.S. Pat. No. 4,388,246, U.S. Pat. No. 4,330,479, U.S. Pat. No. 4,081,472, U.S. Pat. No. 3,962,302, U.S. Pat. No. 3,919,280, U.S. Pat. No. 3,919,279, U.S. Pat. No. 3,919,278 and JP 60-231,640, which are incorporated by reference herein.

PREPARATION OF POLYAMIDES

The polyamides of the invention are prepared by reacting an isocyanate having at least two $-N=C=O$ groups with a dicarboxylic acid or a salt of a dicarboxylic acid in the presence of a suitable solvent and, optionally, a base.

The polymerization reaction of the invention is a $CO_2$-removing reaction and $CO_2$ is given off in a gaseous form. Compared with the HCl-removing or $H_2O$ removing reaction between amino groups and an acid halide or acid, $CO_2$ removal is extremely easy and moreover, there is no danger of side reactions or polymer deterioration due to byproducts.

The polyamides prepared in accordance with the process of the invention are useful as high performance industrial material such as radiation shields, composite materials, reinforcing materials and electrical insulating materials by making effective use of their excellent heat resistance, heat-insulating properties, radiation resistance, thermal dimensional stability, mechanical properties, electrical properties, chemical resistance, flame retardancy, etc. They can be widely used as molded articles, films, papers, fibers, varnishes, adhesives and the like in the fields of electrical and electronic appliances, automobiles, apparel and interior-finishing materials.

The dicarboxylic acids of the invention can be represented by the formula $R_{28}(COOH)_2$ wherein $R_{28}$ is an aliphatic, aromatic, alicyclic and/or heterocyclic group, each of which may optionally be substituted by one or more groups substantially inert to carboxyl groups and isocyanate groups, e.g., alkyl groups, cycloalkyl groups, aryl groups, alkoxy groups, halogens and the like. In addition, two or more of these groups may be coupled together, for example, by way of C—C bond(s). Alternatively, they may be coupled together via alkylene groups,

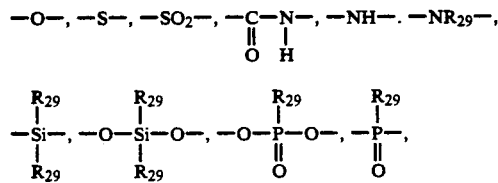

and the like, wherein $R_{29}$ represents an alkyl, cycloalkyl or aryl group and when a group contains two $R_{29}$ substituents, they may be the same or different.

Examples of dicarboxylic acids include, but are not limited to, malonic acid, fumaric acid, succinic acid, glutaric acid, adipic acid, pimelic acid, suberic acid, azelaic acid, sebacic acid, terephthalic acid, isophthalic acid, hexahydroterephthalic acid, diphenylether-4,4'-dicarboxylic acid, diphenylsulfone-4,4'-dicarboxylic acid, biphenyl-4,4'-dicarboxylic acid, thiophene-2,5-dicarboxylic acid, pyridine-2,6-dicarboxylic acid, naphthalene-2,6-dicarboxylic acid, and salts thereof, and mixtures thereof.

Suitable solvents for use in the polymerization reaction include, but are not limited to, linear or cyclic amides, phosphoryl amides, sulfoxides, sulfones, N,N'-dimethylalkyleneureas, and mixtures thereof.

Examples of suitable solvents include, but are not limited to, dimethylformamide, dimethylacetamide, N-methyl-2-pyrrolidone, γ-butyrolactone, hexamethylphosphoric triamide, tetramethylenesulfone, diphenylsulfone, dimethylsulfoxide, tetramethylurea, toluene, triethylamine, N,N'-dimethylethyleneurea, N,N'-dimethylpropyleneurea, and mixtures thereof.

Suitable bases for use in the polymerization reaction include alkali metal hydroxides, alkali metal carbonates or bicarbonates, alkali metal alkoxides or phenoxides, alkali metal salts of polycarboxylic acids, alkali metal lactamates, cyclic phosphorus oxides, tertiary amines and mixtures thereof.

Examples of suitable bases include, but are not limited to, lithium hydroxide, sodium hydroxide, potassium hydroxide, sodium carbonate, potassium carbonate, sodium bicarbonate, lithium bicarbonate, potassium bicarbonate, sodium ethoxide, sodium phenoxide, disodium salt of terephthalic acid, disodium salt of isophthalic acid, monosodium salt of terephthalic acid, triethylamine, trimethylamine, and mixtures thereof.

The molar ratio of the isocyanate having at least two —N=C=O groups to the dicarboxylic acid is broadly in the range of about 0.7:1 to about 1.3:1, preferably in the range of about 0.95:1 to about 1.1:1, and most preferably about 1:1.

The amount of base in the polymerization reaction can conveniently be expressed in terms of a mole percent based on the dicarboxylic acid charged. Broadly, the range is about 0.10 to about 20 mole percent, preferably about 0.5 to about 10 mole percent.

The amount of solvent in the polymerization reaction can conveniently be expressed in terms of the total concentration of the starting monomers, i.e., the isocyanate having at least two —N=C=O groups and the dicarboxylic acid. Broadly, the total concentration is in the range of about 50 to about 400 g/L at the beginning of the polymerization reaction. The selection of this concentration should, however, be made in accordance with the reactivity of the starting monomers, the solubility of the resulting polymer in the solvent, etc. When the polymerization is started at a high concentration, it may, in some instances, be preferable to charge an additional portion of the solvent either continuously or noncontinuously in order to avoid any substantial hindrance to the stirring due to increased viscosity in the cours of the polymerization.

The starting monomers and the base may be added in any order by any suitable method. For example, it is simple and convenient to dissolve them at room temperature in the solvent either simultaneously or successively. In some instances, it is possible to add either one of the starting monomers, preferably the isocyanate having at least two —N=C=O groups continuously at the reaction temperature.

The temperature of the polymerization reaction is preferably above 100° C. but below the boiling point of the solvent. The reaction time will generally be about 1 to about 20 hours. The reaction can be considered to have reached completion at the time where byproduct $CO_2$ is no longer substantially evolved.

Contemplated equivalence of the general formulas set forth above for the reactants and reagents are compounds otherwise corresponding thereto and having the same general properties wherein one or more of the various R groups are simple variations of the substituents as defined therein.

In addition, where a substituent is designated as, or can be, a hydrogen, the exact chemical nature of a substituent which is other than hydrogen at that position is not critical so long as it does not adversely effect the overall synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The invention will now be further disclosed in the following illustrative examples wherein parts and percentages are given on a molar basis unless otherwise specified.

EXAMPLES

For the preparation of substituted aromatic amines having at least two —$NH_2$ groups or intermediates thereof, all yields were determined by HPLC according to the following method.

HPLC Analysis Method: A Waters 600 series HPLC equipped with a Vydac 201HS54 (4.6×250 mm) column and UV detection at 254 nm was used to monitor all reactions. The external standard method was utilized in all the analyses. Authentic samples of products to be used as standards were prepared by known literature methods.

| | Elution Gradient | |
|---|---|---|
| Time (min.) | % Solvent A (Water) | % Solvent B (40% Methanol in ACN) |
| 0 | 75 | 25 |
| 35 | 20 | 80 |
| 40 | 0 | 100 |
| 45 | 0 | 100 |
| 46 | 75 | 25 |
| 55 | 75 | 25 |

For the preparation of isocyanates having at least two —N=C=O groups and carbamate esters having at least two

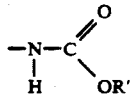

groups, analyses were done according to the following methods.

Gas chromatographic analysis was performed on a Varian Model 3400 gas chromatograph with a Model 8000 auto ampler using a 30 meter Megabore DB-1 (3 μm) J & W Scientific column. Isocyanate and carbamate ester product were purified and were identified by $^1$H NMR and IR spectroscopy. Nuclear Magnetic Resonance spectra were obtained on Varian VXR-300 or VXR-400 spectrometers. Infrared spectra were obtained on a Nicolet FT-IR.

For the preparation of polyamides, analyses were done according to the following methods. Mass spectrometry analysis was performed on a Finnigan 4500 quadrupole mass spectrometer with data collected in the chemical ionization mode using methane as the ionization gas. Infrared spectra were obtained on an IBM 30 FT-IR.

EXAMPLE 1

This example illustrates the direct coupling of benzamide and nitrobenzene to give 4'-nitrobenzanilide.

A solution of tetramethylammonium hydroxide dihydrate (TMA(H)·2$H_2$O) (1.8 g, 14.0 mmole), benzamide (1.2 g., 9.9 mmole) and 10 ml of xylene was stirred under nitrogen at 70° C. The water and xylene was removed by vacuum distillation at 740 mmHg/70° C. Nitrobenzene (1.2 g., 9.7 mmole) was added dropwise and the solution was stirred for 4 hours under nitrogen after which time an aliquot was removed for HPLC analysis. 4'-Nitrobenzanilide was produced in 25% yield based on benzamide. Azoxybenzene was generated in 8% yield in this reaction.

EXAMPLE 2

This example illustrates the hydrogenation of 4'-nitrobenzanilide to 4'-aminobenzanilide using various solvents.

All reactions were carried out in a 300 mL stainless steel autoclave. Thus, 4-nitrobenzanilide (1.0 g., 4.13 mmole) and 3% Pt/carbon catalyst (0.033 g. dry weight) was charged into the autoclave with 80 mL of solvent. The vessel was purged with nitrogen and then was pressurized with 200 psig hydrogen. The solution was heated to 80° C. and agitated at 1500 rpm. Hydrogen uptake was immediately observed. The reaction was considered complete when hydrogen uptake ceased. The mixture was cooled, filtered and a sample was analyzed by HPLC.

TABLE 1

| Solvent | Catalyst (g) | Conversion | Yield |
|---|---|---|---|
| Ethanol | 0.033 | 100% | 100% |
| DMSO | 0.033 | 94% | 52% |
| Aniline | 0.033 | 100% | 100% |

EXAMPLE 3

This example illustrates the hydrogenation of the tetramethylammonium salt of 4'-nitrobenzanilide to 4'-aminobenzanilide using various solvents.

All reactions were carried out in a 300 mL stainless steel autoclave. Thus, 4'-nitrobenzanilide (1.21 g, 5.0 mmole) and TMA(H)·2$H_2$O (7.0 mmole) was mixed in 80 mL of solvent. This mixture was charged into the autoclave with 3% Pt/Carbon catalyst (0.033 g dry weight). The reaction vessel was purged with nitrogen and was then charged with hydrogen at 200 psig. The reaction was heated to 80° C. and agitated at 1500 rpm. Hydrogen uptake was immediately observed. The reaction was considered complete when hydrogen uptake ceased. The mixture was cooled, filtered, and a sample was removed for HPLC analysis.

TABLE 2

| Solvent | Catalyst (g) | Conversion | Yield |
|---|---|---|---|
| Ethanol | 0.033 | 100% | 100% |
| DMSO | 0.033 | 50% | 17% |
| Aniline | 0.033 | 100% | 100% |

EXAMPLE 4

This example illustrates the direct coupling of benzamide and nitrobenzene using DMSO as a co-solvent in the reaction.

A 100 mL round bottom flask equipped with an addition funnel and Dean-Stark trap was charged with benzamide (1.27 g., 10.4 mmole), tetramethylammonium hydroxide pentahydrate (TMA(H)·5$H_2$O)(2.17 g, 11.9 mmole) and xylene (8.5 g). The xylene and water were removed by vacuum distillation (20 torr). The reaction mixture was maintained between 70°-80° C. A mixture of nitrobenzene (1.23 g, 10.0 mmole) and DMSO (1.28 g) was added dropwise to the reaction under nitrogen over 30 minutes. The reaction was maintained at 80° C. and the mixture was allowed to stir. After 4 hours an aliquot was removed and analyzed by HPLC. Yield based benzamide: 4'-nitrobenzanilide 77%, azoxybenzene 9%.

EXAMPLE 5

This example illustrates the effect of protic material on the production of 4'-nitrobenzanilide.

A 100 mL round bottom flask equipped with an addition funnel and Dean-Stark trap was charged with benzamide (1.27 g., 10.4 mmole), TMA(H)·5H$_2$O (2.17 g, 11.9 mmole) and xylene (8.5 g). The xylene and water were removed as the azeotrope by vacuum distillation (20 torr). The reaction mixture was maintained between 70°–80° C. Various amounts of water was then added back to the reaction. Following the re-addition of water, a 40 mixture of nitrobenzene (1.23 g, 10.0 mmole) and DMSO (1.28 g) was added dropwise to the reaction under nitrogen over 30 minutes. The reaction was maintained at 80° C. and the mixture was allowed to stir. After 4 hours an aliquot was removed and analyzed by HPLC.

TABLE 3

| Mole Ratio Water:TMA(H) | % Yield 4-Nitrobenzanilide |
|---|---|
| 10 | 0 |
| 7 | 0 |
| 3 | 5 |
| <1 | 77 |

EXAMPLE 6

This example illustrates the coupling of benzamide and nitrobenzene in various solvent systems.

In a typical experiment, 1.2 g of nitrobenzene, 1.8 g TMA(H)·2H$_2$O, 1.2 g of benzamide and 10 ml solvent was stirred under nitrogen at 70° C. for 12 hours. An aliquot was removed for HPLC analysis. Yields were based on benzamide.

TABLE 4

| Solvent | % Yield | | |
|---|---|---|---|
| | 4'-Nitro-benzanilide | Azoxybenzene | Azobenzene |
| Pyradine | 19 | 6.5 | 0 |
| Xylene | 0 | 0 | 0 |
| N-Methylaniline | 6.3 | 9.5 | 0 |
| Chlorobenzene | 69 | 2 | 13 |
| NMP | 39 | 1.5 | 4.8 |
| Nitrobenzene | 100 | 48 | — |

EXAMPLE 7

This example illustrates the aminolysis of 4'-aminobenzanilide in methanol to give 1,4-phenylenediamine.

Approximately 10 ml of liquid ammonia was added rapidly to a solution of 100 mg of 4'-nitrobenzanilide and 50 ml of methanol in a Parr bomb at −50° C. the Parr reactor was stirred at 200° C./300 psi for 3 days. After the reactor was cooled to −50° C., the pressure was release and the reactor was opened. An aliquot was taken out for HPLC analysis and compared with authentic samples. HPLC analysis showed 40% yield of 1,4-phenylenediamine and benzamide. The remainder of the material was unreacted.

EXAMPLE 8

This example illustrates the production 4,4'-diaminodiphenylamine produced from the reaction of a substituted aromatic amine having at least two —NH$_2$ groups, 1,4-phenylenediamine, with azobenzene.

A solution of 1.8 g of azobenzene, 5 g of 1,4-phenylenediamine, 2.24 g of potassium t-butoxide and 2.6 g of 18-crown-6 was heated under nitrogen for 30 minutes. An aliquot was removed for HPLC analysis. The yield of 4,4'-diaminodiphenylamine based on azobenzene was 30%.

EXAMPLE 9

This example illustrates how a substituted aniline derivative, e.g. 4-nitroaniline, can be employed in this reaction according to embodiment (a$_7$).

A solution of (1.38 g, 0.01 mole) of 4-nitroaniline and 1.81 g (0.012 mole) of tetramethylammonium hydroxide dihydrate in 3 ml of dimethylsulfoxide was stirred at 70° C. under nitrogen. Nitrobenzene 1 ml (0.01 mole) was added dropwise via a syringe and the solution was stirred at 70° C. under nitrogen for 12 hours. The reaction was analyzed by HPLC. The conversion of nitrobenzene was 99% and the yield of 4,4'-dinitrodiphenylamine was 73%.

EXAMPLE 10

This example illustrates how a variety of diamino nucleophiles will couple to the para position of nitrobenzene according to embodiment (a$_7$).

Nitrobenzene (2 ml, 0.02 mole) was added via a syringe to a stirring solution containing 1.08 g (0.01 mole) of 1,4-phenylenediamine, 3.6 g (0.02 mole) of tetramethylammonium hydroxide pentahydrate in 2 ml of dimethylsulfoxide under nitrogen at 70° C. The solution was stirred at such condition for 4 hours. An aliquot was taken out for LC, MS, LC-MS analyses. N,N'-(4-nitrosophenyl)-1,4-phenylenediamine, N-(4-nitrophenyl)-N'-(4-nitrosophenyl)-1,4-phenylenediamine and N,N'-(4-nitrophenyl)-1,4-phenylenediamine were obtained.

Other diamino nucleophiles such as 4,4'-methylenedianiline and 2,4-diaminotoluene also give similar results under identical reaction conditions.

EXAMPLE 11

This example illustrates the conversion of the p-phenylenediamine to 1,4-phenylenediisocyanate.

A 9 oz. Fisher Porter bottle was charged with p-phenylenediamine (2.16 g, 20 mmol), N-cyclohexyl-N',N',N'',N''-tetraethyl guanidine (10.12 g, 40 mmol), triethylamine (8.4 mL, 60 mmol) and 100 mL CH$_2$Cl$_2$ and then pressurized to 80 psi with CO$_2$. An exothermic reaction occurred upon addition of the CO$_2$ and after stirring for 30 min. at room temperature the solution was cooled to 0° C. in an ice bath. Phosphorous oxychloride (3.7 mL, 40 mmol) was added rapidly to the cold solution causing an exothermic reaction and formation of a pale yellow precipitate. Removal of the ice bath and stirring at room temperature for an additional 30 min. followed by the addition of 150 mL of diethyl ether and filtration through celite gave a pale yellow filtrate from which 2.03 g (62%) of pure p-phenylenediisocyanate was isolated by crystallization.

EXAMPLE 12

This example illustrates the direct conversion of p-phenylenediamine to the corresponding di-benzyl carbamate ester.

A Fischer-Porter bottle was charged with 1.08 g (0.01 mol) p-phenylenediamine, 6.33 g (0.025 mol) N- cyclohexyl-N',N',N",N"-tetraethylguanidine, and 20 mL CH₃CN. The Fischer-Porter bottle was attached to a pressure head and at room temperature with stirring was added 40 psig carbon dioxide. Addition of $CO_2$ resulted in an exothermic reaction with a rise in temperature to ca. 40° C. Into a second Fischer-Porter bottle was added 5.06 g (0.04 mol) benzylchloride in 10 mL CH₃CN. This mixture was attached to a pressure head and 40 psig carbon dioxide was added above the solution. After 1 h the benzyl chloride solution was added all at once under 40 psig $CO_2$ to the pre-formed carbamate anion solution generated in the first Fischer-Porter bottle. After addition the reaction mixture was warmed to 55° C. for 4 h (during which time a white solid precipitated from solution). After this time the reaction mixture was allowed to cool to room temperature and then the pressure was released. The white solid was collected by filtration and then washed with 100 mL CH₃CN and 100 mL diethyl ether. After air drying a 70% (2.64 g) of 1,4-phenylene-, bis(phenylmethyl) carbamate was isolated. m.p.=235°-237° C.; ¹H NMR (DMSO-d₆) δ9.61 (s, 2H, N—H), 7.4–7.3 (overlapping m, 14H), 5.11 (s, 4H).

EXAMPLE 13

This example illustrates the direct conversion of p-phenylenediamine to the corresponding di-ethyl carbamate ester.

A 160 cc Parr autoclave was charged with 4.32 g (0.04 mol) p-phenylenediamine, 25.3 g (0.1 mol) N-cyclohexyl-N',N',N",N"-tetraethylguanidine, and 50 mL CH₃CN. The autoclave was attached to a pressure head and at room temperature with stirring was added 40 psig carbon dioxide. Addition of $CO_2$ resulted in an exothermic reaction with a rise in temperature to ca. 40° C. Into a second Fischer-Porter bottle was added ca. 15 mL (13 g, 0.2 mol) ethyl chloride. This was attached to a pressure head and 40 psig carbon dioxide was added above the solution. After 1 h the ethyl chloride solution was added all at once under 40 psig $CO_2$ to the pre-formed carbamate anion solution generated in the autoclave. After addition the reaction mixture was warmed to 85° C. for 20 h. After this time the reaction mixture was allowed to cool to room temperature and then the pressure was released. The crude reaction mixture was poured into 250 mL 0.5 M aqueous HCl. A tan precipitate formed and was collected by filtration. This was washed several times with water. After air drying a 73% (7.33 g) isolated yield of 1,4-phenylene-, bis(ethyl) carbamate was obtained. m.p.=199°-202° C. ¹H NMR (DMSO-d₆) δ9.45 (s, 2H, N—H), 7.36 (s, 4H), 4.11 (q, J=7.1 H₂, 4H), 1.24 (t, J=7.1 Hz, 6H). ¹³C{¹H} NMR (DMSO-d₆) δ153.5, 133.9, 118.7, 59.9, 14.4; IR (CHCl₃) 3434, 1728.

EXAMPLE 14

This example illustrates the direct conversion of 4,4'-diaminobenzanilide to the corresponding 4,4'-dibenzyl carbamate ester.

A 300 cc Parr autoclave was charge with 4.54 g (0.02 mol) of 4,4'-diaminobenzanilide, 16.6 g (6.6×10⁻² mol) of N-cyclohexyl-N',N',N",N"-tetraethylguanidine (CyTEG) and 100 mL of acetonitrile. The autoclave was sealed and pressurized to 80 psi with $CO_2$ causing an exothermic reaction to occur. The reaction mixture was stirred for one hour after which time 15.2 mL (0.13 mol) of benzyl chloride was added and the temperature increased to 55° C. for 15 hrs. Following the reaction period, the autoclave was cooled to room temperature and the contents filtered through a medium frit. The product was collected as a fine white powder that was washed with 2×25 mL portions of cold methanol and then dried in vacuo to give 8.8 g (89% yield) of pure 4,4'-dibenzylcarbamatobenzanilide (m.p. 275°-278° C., decomp.).

EXAMPLE 15

This example illustrates the reaction of terephthalic acid and 1,4-phenylene diisocyanate generating a polyamide.

A solution of 100 mg of terephthalic acid, 100 mg of 1,4-phenylenediisocyanate and 0.1 ml of triethylamine in 10 ml of xylene was stirred under nitrogen at reflux for 12 hours. After the solution was cooled to room temperature, the precipitate was filtered under suction and dried to obtain 100 mg of light brown solid. Mass spectrometry (CI) of the product showed no 1,4-phenylenediisocyanate remained. Infrared spectroscopy (KBr pellet) revealed a broad absorption band at 1674 cm⁻¹ which can be assigned to the aromatic amide bond stretch. An authentic sample of polyamide also contained this absorption band.

Similar results were also obtained when DMSO was used as solvent in place of xylene under identical reaction conditions.

That which is claimed is:

1. A process for preparing an isocyanate having at least two —N═C═O groups comprising:

(a)
   (i) contacting an amide selected from the group consisting of diamides, substituted aliphatic amides represented by the formula

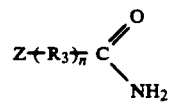

and substituted aromatic amides containing at least one substituent on the aromatic ring selected from the group consisting of —NO₂, —NH₂ and alkyl, aryl, aralkyl, and alkaryl groups containing at least one —NH₂ group, and nitrobenzene in the presence of a suitable solvent system wherein n is 0 or 1, R₃ is selected from the group consisting of alkyl, aralkyl, alkenyl, aralkenyl, cycloalkyl and cyloalkenyl groups, and Z is selected from the group consisting of —NO₂, —NH₂ and alkyl, aryl, aralkyl and alkaryl groups containing at least one —NH₂ group, (ii) reacting said amide of (a)(i) and nitrobenzene in the presence of a suitable base and a controlled amount of protic material at a suitable temperature in a confined reaction zone, and (iii) reducing the reaction product of (a)(ii) under conditions which produce a substituted aromatic amine having at least two —NH₂ groups; or (a₁)
   (i) contacting an amide and nitrobenzene in the presence of a suitable solvent system, (ii) reacting said amide of (a₁)(i) and nitrobenzene in the presence of a suitable base and a controlled amount of protic material at a suitable temperature in a confined reaction zone to produce a p-nitroaromatic amide, (iii) reducing said p-nitroaromatic amide of (a₁)(ii) under conditions which produce a p-aminoaromatic amide, and (iv) reacting said p-aminoaromatic amide with ammonia under conditions which produce the corresponding substituted aromatic amine having at least two —NH₂ groups and amide; or (a₂)
(i) contacting an amide and nitrobenzene in the presence of a suitable solvent system, (ii) reacting said amide of (a₂)(i) and nitrobenzene in the presence of a suitable base and a controlled amount of protic material at a suitable temperature in a confined reaction zone to produce a p-nitroaromatic amide, (iii) reacting said p-nitroaromatic amide of (a₂)(ii) with ammonia under conditions which produce the corresponding p-nitroaromatic amine and amide, and (iv) reducing said p-nitroaromatic amine under conditions which produce the corresponding substituted aromatic amine having at least two —NH₂ groups; or (a₃)
(i) contacting an amide or a substituted aromatic amine having at least two —NH₂ groups, wherein said amide is selected from the group consisting of diamides, substituted aliphatic amides represented by the formula

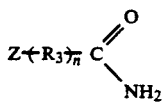

and substituted aromatic amides containing at least one substituent on the aromatic ring selected from the group consisting of —NH₂ and alkyl, aryl, aralkyl and alkaryl groups containing at least one —NH₂ group, and an azo containing compound represented by the formula X—R₁—N=N—R₂—Y or azoxy or hydrazo derivatives thereof in the presence of a suitable solvent system wherein n is 0 or 1, R₃ is selected from the group consisting of alkyl, aralkyl, alkenyl, aralkenyl, cycloalkyl and cycloalkenyl groups, Z is selected from the group consisting of —NH₂ and alkyl, aryl, aralkyl and alkaryl groups containing at least one —NH₂ group, R₁ is an aromatic group, R₂ is selected from the group consisting of aliphatic and aromatic groups, and X and Y are independently selected from the group consisting of hydrogen, halides, —NO₂, —NH₂, aryl groups, alkyl groups, alkoxy groups, —SO₃, —SO₃R₃₀, —OR₃₀, —COOR₃₀, and alkyl, aryl, aralkyl or alkaryl groups containing at least one —NH₂ group, wherein R₃₀ is selected from the group consisting of aliphatic and aromatic groups, if R₂ is aliphatic, X is in the meta or ortho position on R₁ and if R₂ is aromatic, at least one of X and Y is in the meta or ortho position on R₁ and R₂, respectively, and wherein halides are selected from the group consisting of chloride, bromide and fluoride, (ii) reacting said amide or said substituted aromatic amine having at least two —NH₂ groups of (a₃)(i) and said azo containing compound in the presence of a suitable base and a controlled amount of protic material at a reaction temperature of about 10° C. to about 150° C. in a confined reaction zone to produce a substituted aromatic azo compound wherein the molar ratio of protic material to base is 0:1 to about 5:1, and (iii) reacting said substituted aromatic azo compound of (a₃)(ii) with a nucleophilic compound selected from the group consisting of aniline, substituted aniline derivatives, aliphatic amines, substituted aliphatic amine derivatives, amides and substituted aromatic amines having at least two —NH₂ groups in the presence of a suitable solvent system, a suitable base and a controlled amount of protic material at a reaction temperature of about 70° C. to about 200° C. in a confined reaction zone to produce a substituted aromatic amine having at least two —NH₂ groups, wherein the molar ratio of protic material to base is 0:1 to about 5:1; or (a₄)
(i) contacting an amide and an azo containing compound represented by the formula X—R₁—N=N—R₂—Y or azoxy or hydrazo derivatives thereof in the presence of a suitable solvent system, wherein R₁ is an aromatic group, R₂ is selected from the group consisting of aliphatic and aromatic groups, and X and Y are independently selected from the group consisting of hydrogen, halides, —NO₂, —NH₂, aryl groups, alkyl groups, alkoxy groups, —SO₃, —SO₃R₃₀, —OR₃₀, —COOR₃₀, and alkyl, aryl, aralkyl or alkaryl groups containing at least one —NH₂ group, wherein R₃₀ is selected from the group consisting of aliphatic and aromatic groups, if R₂ is aliphatic, X is in the meta or ortho position on R₁ and if R₂ is aromatic, at least one of X and Y is in the meta or ortho position on R₁ and R₂, respectively, and wherein halides are selected from the group consisting of chloride, bromide and fluoride, (ii) reacting said amide of (a₄)(i) and said azo containing compound in the presence of a suitable base and a controlled amount of protic material at a reaction temperature of about 10° C. to about 150° C. in a confined reaction zone to produce a substituted aromatic azo compound, wherein the molar ratio of protic material to base is 0:1 to about 5:1, (iii) reacting said substituted aromatic azo compound of (a₄)(ii) with a nucleophilic compound selected from the group consisting of aniline, substituted aniline derivatives, aliphatic amines, substituted aliphatic amine derivatives, amides and substituted aromatic amines having at least two —NH₂ groups in the presence of a suitable solvent system, a suitable base and a controlled amount of protic material at a reaction temperature of about 70° C. to about 200° C. in a confined reaction zone to produce a substituted aromatic amine containing an aromatic amide bond wherein the molar ratio of protic material to base is 0:1 to about 5:1, and (iv) reacting said substituted aromatic amine of (a₄)(iii) with ammonia under conditions which produce the corresponding substituted aromatic amine having at least two —NH₂ groups and amide; or (a₅)
(i) contacting a nucleophilic compound selected from the group consisting of aniline, substituted aniline derivatives, aliphatic amines, substituted aliphatic amine derivatives, amides and substituted aromatic amines having at least two —NH₂ groups with a substituted aromatic azo compound or azoxy or hydrazo derivatives thereof in the presence of a suitable solvent system, and (ii) reacting said nucleophilic compound and said substituted aromatic azo compound or azoxy or hydrazo derivatives thereof in the presence of a suitable base and a controlled amount of protic material at a reaction temperature of about 70° C. to about 200° C. to produce a substituted aromatic amine having at least two —NH₂ groups, wherein the molar ratio of protic material to base is 0:1 to about 5:1, wherein the substituted aromatic azo compound is selected from the group consisting of compounds represented by the formula:

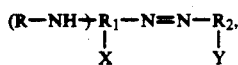
(I)

compounds represented by the formula:

(II)

compounds represented by the formula:

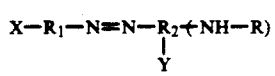
(III)

and mixtures thereof, wherein R—NH— represents a substituent derived from an amide or a substituted aromatic amine having at least two —NH₂ groups, wherein said amide is selected from the group consisting of diamides, substituted aliphatic amides represented by the formula

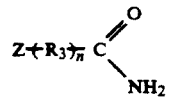

and substituted aromatic amides containing at least one substituent on the aromatic ring selected from the group consisting of —NH₂ and alkyl, aryl, aralkyl and alkaryl groups containing at least one —NH₂ group, wherein n is 0 or 1, R₃ is selected from the group consisting of alkyl, aralkyl, alkenyl, aralkenyl, cycloalkyl and cycloalkenyl groups, Z is selected from the group consisting of —NH₂ and alkyl, aryl, aralkyl and alkaryl groups containing at least one —NH₂ group, R₁ is an aromatic group, R₂ is selected from the group consisting of aliphatic and aromatic groups, and X and Y are independently selected from the group consisting of hydrogen, halides, —NO₂, —NH₂, aryl groups, alkyl groups, alkoxy groups, —SO₃, —SO₃R₃₀, —OR₃₀, —COOR₃₀, and alkyl, aryl, aralkyl or alkaryl groups containing at least one —NH₂ group, wherein R₃₀ is selected from the group consisting of aliphatic and aromatic groups, halides are selected from the group consisting of chlorine, bromine and fluorine and R₂ is an aromatic group in substituted aromatic azo compounds (II) and (III); or (a₆)
(i) contacting a nucleophilic compound selected from the group consisting of aniline, substituted aniline derivatives, aliphatic amines, substituted aliphatic amine derivatives, amides and substituted aromatic amines having at least two —NH₂ groups with a substituted aromatic azo compound or azoxy or hydrazo derivatives thereof in the presence of a suitable solvent system, (ii) reacting said nucleophilic compound and said substituted aromatic azo compound or azoxy or hydrazo derivatives thereof in the presence of a suitable base and a controlled amount of protic material at a reaction temperature of about 70° C. to about 200° C. to produce a substituted aromatic amine containing an aromatic amide bond, wherein the molar ratio of protic material to base is 0:1 to about 5:1, wherein the substituted aromatic azo compound is selected from the group consisting of compounds represented by the formula:

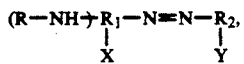
(I)

compounds represented by the formula:

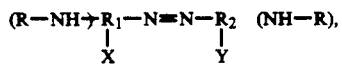
(II)

compounds represented by the formula:

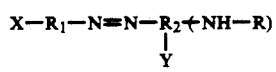
(III)

and mixtures thereof, wherein R—NH—represents a substituent derived from an amide, R₁ is an aromatic group, R₂ is selected from the group consisting of aliphatic and aromatic groups, and X and Y are independently selected from the group consisting of hydrogen, halides, —NO₂, —NH₂, aryl groups, alkyl groups, alkoxy groups, —SO₃, —SO₃R₃₀, —OR₃₀, —COOR₃₀, and alkyl, aryl, aralkyl or alkaryl groups containing at least one —NH₂ group, wherein R₃₀ is selected from the group consisting of aliphatic and aromatic groups, halides are selected from the group consisting of chlorine, bromine and fluorine and R₂ is an aromatic group in substituted aromatic azo compounds (II) and (III), and (iii) reacting said substituted aromatic amine of (a₆)(ii) with ammonia under conditions which produce the corresponding substituted aromatic amine having at least two —NH₂ groups and amide; or (a₇)

(i) contacting a substituted aniline derivative, wherein the substituents are selected from the group consisting of halide, $-NO_2$, $-NH_2$, alkyl groups, alkoxy groups, $-SO_3$, $-COOR_{30}$ and aryl, aralkyl or alkaryl groups containing at least one $-NH_2$ group provided said substituted aniline derivative contains at least one substituent selected from the group consisting of $-NO_2$, $-NH_2$ and aryl, aralkyl or alkaryl groups containing at least one $-NH_2$ group, and nitrobenzene in a suitable solvent system, (ii) reacting said substituted aniline derivative and nitrobenzene in a confined reaction zone at a suitable temperature, and in the presence of a suitable base and a controlled amount of protic material, and (iii) reducing the reaction product of (a7)(ii) under conditions to produce a substituted aromatic amine having at least two $-NH_2$ groups, (b) recovering said substituted aromatic amine having at least two $-NH_2$ groups, and (c)
 (i) contacting $CO_2$ and said substituted aromatic amine having at least two $-NH_2$ groups in the presence of an aprotic organic solvent and an organic, nitrogenous base, under reaction conditions of time and temperature sufficient to produce the corresponding ammonium carbamate salt, and (ii) reacting said ammonium carbamate salt with an electrophilic or oxophilic dehydrating agent selected from the group consisting of $POX'_3$, $PX'_3$, $SOX'_2$, $SO_2X'_2$, $SO_3$, $PX'_5$, $P_2O_5$, $NO_y$, $NOX'$, ketene, acid anhydrides having the formula:

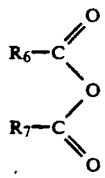

acid halides having the formula

and halides or oxyhalides of metals selected from the group consisting of transition metals, Group III B metals, Group IV B metals, and Group V B metals, and mixtures thereof wherein $R_6$ and $R_7$ are independently selected from the group consisting of fluoroalkyl, alkyl, aryl, alkaryl and aralkyl radicals having 1 to about 22 carbon atoms, X' is chlorine or bromine, halides are chlorides or bromides, and y is 1 or 2 under reaction conditions of time and temperature sufficient to produce the corresponding isocyanate having at least two $-N=C=O$ groups; or (c₁)
 (i) contacting $CO_2$ and said substituted aromatic amine having at least two $-NH_2$ groups in the presence of an organic, nitrogenous base selected form the group consisting of guanidine compounds, amidine compounds, phosphazene compounds and mixtures thereof, under reaction conditions of time and temperature sufficient to produce the corresponding ammonium carbamate salt, (ii) reacting, in a polar aprotic solvent, said salt with a primary or secondary hydrocarbyl halide under reaction conditions of time and temperature sufficient to produce the corresponding carbamate ester, and (iii) cracking said carbamate ester under conditions to produce the corresponding isocyanate having at least two $-N=C=O$ groups.

2. The process according to claim 1 comprising:

(a)
 (i) contacting an amide selected from the group consisting of diamides, substituted aliphatic amides represented by the formula

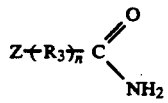

and substituted aromatic amides containing at least one substituent on the aromatic ring selected from the group consisting of $-NO_2$, $-NH_2$ and alkyl, aryl, aralkyl, and alkaryl groups containing at least one $-NH_2$ group, and nitrobenzene in the presence of a suitable solvent system wherein n is 0 or 1, $R_3$ is selected from the group consisting of alkyl, aralkyl, alkenyl, aralkenyl, cycloalkyl and cyloalkenyl groups, and Z is selected from the group consisting of $-NO_2$, $-NH_2$ and alkyl, aryl, aralkyl and alkaryl groups containing at least one $-NH_2$ group, (ii) reacting said amide of (a)(i) and nitrobenzene in the presence of a suitable base and a controlled amount of protic material at a suitable temperature in a confined reaction zone, and (iii) reducing the reaction product of (a)(ii) under conditions which produce a substituted aromatic amine having at least two $-NH_2$ groups;

(b) recovering said substituted aromatic amine having at least two $-NH_2$ groups, and (c)
 (i) contacting $CO_2$ and said substituted aromatic amine having at least two $-NH_2$ groups in the presence of an aprotic organic solvent and an organic, nitrogenous base, under reaction conditions of time and temperature sufficient to produce the corresponding ammonium carbamate salt, and (ii) reacting said ammonium carbamate salt with an electrophilic or oxophilic dehydrating agent selected from the group consisting of $POX'_3$, $PX'_3$, $SOX'_2$, $SO_2X'_2$, $SO_3$, $PX'_5$, $P_2O_5$, $NO_6$, $NOX'$, ketene, acid anhydrides having the formula:

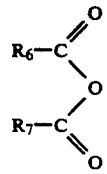

acid halides having the formula

and halides or oxyhalides of metals selected from the group consisting of transition metals, Group III B metals, Group IV B metals, and Group V B metals, and mixtures thereof wherein $R_6$ and $R_7$ are independently selected from the group consisting of fluoroalkyl, alkyl, aryl, alkaryl and aralkyl radicals having 1 to about 22 carbon atoms, $X'$ is chlorine or bromine, halides are chlorides or bromides, and y is 1 or 2 under reaction conditions of time and temperature sufficient to produce the corresponding isocyanate having at least two $-N=C=O$ groups.

3. The process according to claim 1 comprising:
($a_1$)
 (i) contacting an amide and nitrobenzene in the presence of a suitable solvent system,
 (ii) reacting said amide of ($a_1$)(i) and nitrobenzene in the presence of a suitable base and a controlled amount of protic material at a suitable temperature in a confined reaction zone to produce a p-nitroaromatic amide,
 (iii) reducing said p-nitroaromatic amide of ($a_1$)(ii) under conditions which produce a p-aminoaromatic amide, and
 (iv) reacting said p-aminoaromatic amide with ammonia under conditions which produce the corresponding substituted aromatic amine having at least two $-NH_2$ groups and amide; or
(b) recovering said substituted aromatic amine having at least two $-NH_2$ groups, and
(c)
 (i) contacting $CO_2$ and said substituted aromatic amine having at least two $-NH_2$ groups in the presence of an aprotic organic solvent and an organic, nitrogenous base, under reaction conditions of time and temperature sufficient to produce the corresponding ammonium carbamate salt, and
 (ii) reacting said ammonium carbamate salt with an electrophilic or oxophilic dehydrating agent selected from the group consisting of $POX'_3$, $PX'_3$, $SOX'_2$, $SO_2X'_2$, $SO_3$, $PX'_5$, $P_2O_5$, $NO_y$, $NOX'$, ketene, acid anhydrides having the formula:

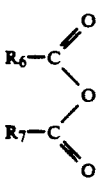

acid halides having the formula

and halides or oxyhalides of metals selected from the group consisting of transition metals, Group III B metals, Group IV B metals, and Group V B metals, and mixtures thereof wherein $R_6$ and $R_7$ are independently selected from the group consisting of fluoroalkyl, alkyl, aryl, alkaryl and aralkyl radicals having 1 to about 22 carbon atoms, $X'$ is chlorine or bromine, halides are chlorides or bromides, and y is 1 or 2 under reaction conditions of time and temperature sufficient to produce the corresponding isocyanate having at least two $-N=C=O$ groups.

4. The process according to claim 1 comprising:
($a_2$)
 (i) contacting an amide and nitrobenzene in the presence of a suitable solvent system,
 (ii) reacting said amide of ($a_2$)(i) and nitrobenzene in the presence of a suitable base and a controlled amount of protic material at a suitable temperature in a confined reaction zone to produce a p-nitroaromatic amide,
 (iii) reacting said p-nitroaromatic amide of ($a_2$)(ii) with ammonia under conditions which produce the corresponding p-nitroaromatic amine and amide, and
 (iv) reducing said p-nitroaromatic amine under conditions which produce the corresponding substituted aromatic amine having at least two $-NH_2$ groups;
(b) recovering said substituted aromatic amine having at least two $-NH_2$ groups, and
(c)
 (i) contacting $CO_2$ and said substituted aromatic amine having at least two $-NH_2$ groups in the presence of an aprotic organic solvent and an organic, nitrogenous base, under reaction conditions of time and temperature sufficient to produce the corresponding ammonium carbamate salt, and
 (ii) reacting said ammonium carbamate salt with an electrophilic or oxophilic dehydrating agent selected from the group consisting of $POX'_3$, $PX'_3$, $SOX'_2$, $SO_2X'_2$, $SO_3$, $PX'_5$, $P_2O_5$, $NO_y$, $NOX'$, ketene, acid anhydrides having the formula:

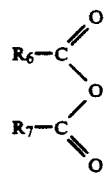

acid halides having the formula

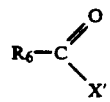

and halides or oxyhalides of metals selected from the group consisting of transition metals, Group III B metals, Group IV B metals, and Group V B metals, and mixtures thereof wherein $R_6$ and $R_7$ are independently selected from the group consisting of fluoroalkyl, alkyl, aryl, alkaryl and aralkyl radicals having 1 to about 22 carbon atoms, $X'$ is chlorine or bromine, halides are chlorides or bromides, and y is 1 or 2 under reaction conditions of time and temperature sufficient to produce the corresponding isocyanate having at least two —N=C=O groups.

5. The process according to claim 1 comprising:

(a₃)
(i) contacting an amide or a substituted aromatic amine having at least two —NH₂ groups, wherein said amide is selected from the group consisting of diamides, substituted aliphatic amides represented by the formula

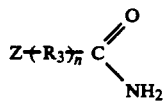

and substituted aromatic amides containing at least one substituent on the aromatic ring selected from the group consisting of —NH₂ and alkyl, aryl, aralkyl and alkaryl groups containing at least one —NH₂ group, and an azo containing compound represented by the formula X—R₁—N=N—R₂—Y or azoxy or hydrazo derivatives thereof in the presence of a suitable solvent system wherein n is 0 or 1, R₃ is selected from the group consisting of alkyl, aralkyl, alkenyl, aralkenyl, cycloalkyl and cycloalkenyl groups, Z is selected from the group consisting of —NH₂ and alkyl, aryl, aralkyl and alkaryl groups containing at least one —NH₂ group, R₁ is an aromatic group, R₂ is selected from the group consisting of aliphatic and aromatic groups, and X and Y are independently selected from the group consisting of hydrogen, halides, —NO₂, —NH₂, aryl group, alkyl groups, alkoxy groups, —SO₃, —SO₃R₃₀, —OR₃₀, —COOR₃₀, and alkyl, aryl, aralkyl or alkaryl groups containing at least one —NH₂ group, wherein R₃₀ is selected from the group consisting of aliphatic and aromatic groups, if R₂ is aliphatic, X is in the meta or ortho position on R₁ and if R₂ is aromatic, at least one of X and Y is in the meta or ortho position on R₁ and R₂, respectively, and wherein halides are selected from the group consisting of chloride, bromide and fluoride, (ii) reacting said amide or said substituted aromatic amine having at least two —NH₂ groups of (a₃)(i) and said azo containing compound in the presence of a suitable base and a controlled amount of protic material at a reaction temperature of about 10° C. to about 150° C. in a confined reaction zone to produce a substituted aromatic azo compound wherein the molar ratio of protic material to base is 0:1 to about 5:1, and (iii) reacting said substituted aromatic azo compound of (a₃)(ii) with a nucleophilic compound selected from the group consisting of aniline, substituted aniline derivatives, aliphatic amines, substituted aliphatic amine derivatives, amides and substituted aromatic amines having at least two —NH₂ groups in the presence of a suitable solvent system, a suitable base and a controlled amount of protic material at a reaction temperature of about 70° C. to about 200° C. in a confined reaction zone to produce a substituted aromatic amine having at least two —NH₂ groups, wherein the molar ratio of protic material to base is 0:1 to about 5:1;

(b) recovering said substituted aromatic amine having at least two —NH₂ groups, and (c)
(i) contacting CO₂ and said substituted aromatic amine having at least two —NH₂ groups in the presence of an aprotic organic solvent and an organic, nitrogenous base, under reaction conditions of time and temperature sufficient to produce the corresponding ammonium carbamate salt, and (ii) reacting said ammonium carbamate salt with an electrophilic or oxophilic dehydrating agent selected from the group consisting of POX′₃, PX′₃, SOX′₂, SO₂X′₂, SO₃, PX′₅, P₂O₅, NO_y, NOX′, ketene, acid anhydrides having the formula:

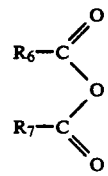

acid halides having the formula

and halides or oxyhalides of metals selected from the group consisting of transition metals, Group III B metals, Group IV B metals, and Group V B metals, and mixtures thereof wherein R₆ and R₇ are independently selected from the group consisting of fluoroalkyl, alkyl, aryl, alkaryl and aralkyl radicals having 1 to about 22 carbon atoms, X′ is chlorine or bromine, halides are chlorides or bromides, and y is 1 or 2 under reaction conditions of time and temperature sufficient to produce the corresponding isocyanate having at least two —N=C=O groups.

6. The process according to claim 1 comprising:

(a₄)
(i) contacting an amide and an azo containing compound represented by the formula X—R₁—N=N—R₂—Y or azoxy or hydrazo derivatives thereof in the presence of a suitable solvent system, wherein R₁ is an aromatic group, R₂ is selected from the group consisting of aliphatic and aromatic groups, and X and Y are independently selected from the group consisting of hydrogen, halides, —NO₂, —NH₂, aryl groups, alkyl groups, alkoxy groups, —SO₃, —SO₃R₃₀, —OR₃₀, —COOR₃₀, and alkyl, aryl, aralkyl or alkaryl groups containing at least one —NH₂ group, wherein R₃₀ is selected from the group consisting of aliphatic and aromatic groups, if R₂ is aliphatic, X is in the meta or ortho position on R₁ and if R₂ is aromatic, at least one of X and Y is in the meta or ortho position on R₁ and R₂, respectively, and wherein halides are selected from the group consisting of chloride, bromide and fluoride, (ii) reacting said amide of (a₄)(i) and said azo containing compound in the presence of a suitable base and a controlled amount of protic material at a reaction temperature of about 10° C. to about 150° C. in a confined reaction zone to produce a substituted aromatic azo compound, wherein the molar ratio of protic material to base is 0:1 to about 5:1, (iii) reacting said substituted aromatic azo compound of (a₄)(ii) with a nucleophilic compound selected from the group consisting of aniline, substituted aniline derivatives, aliphatic amines, substituted aliphatic amine derivatives, amides and substituted aromatic amines having at least two —NH₂ groups in the presence of a suitable solvent system, a suitable base and a controlled amount of protic material at a reaction temperature of about 70° C. to about 200° C. in a confined reaction zone to produce a substituted aromatic amine containing an aromatic amide bond wherein the molar ratio of protic material to base is 0:1 to about 5:1, and (iv) reacting said substituted aromatic amine of (a₄)(iii) with ammonia under conditions which produce the corresponding substituted aromatic amine having at least two —NH₂ groups and amide;

(b) recovering said substituted aromatic amine having at least two —NH₂ groups, and (c)
(i) contacting CO₂ and said substituted aromatic amine having at least two —NH₂ groups in the presence of an aprotic organic solvent and an organic, nitrogenous base, under reaction conditions of time and temperature sufficient to produce the corresponding ammonium carbamate salt, and (ii) reacting said ammonium carbamate salt with an electrophilic or oxophilic dehydrating agent selected from the group consisting of POX'₃, PX'₃, SOX'₂, SO₂X'₂, SO₃, PX'₅, P₂O₅, NO_y, NOX', ketene, acid anhydrides having the formula:

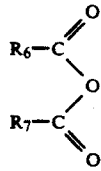

acid halides having the formula

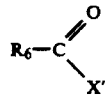

and halides or oxyhalides of metals selected from the group consisting of transition metals, Group III B metals, Group IV B metals, and Group V B metals, and mixtures thereof wherein R₆ and R₇ are independently selected from the group consisting of fluoroalkyl, alkyl, aryl, alkaryl and aralkyl radicals having 1 to about 22 carbon atoms, X' is chlorine or bromine, halides are chlorides or bromides, and y is 1 or 2 under reaction conditions of time and temperature sufficient to produce the corresponding isocyanate having at least two —N=C=O groups.

7. The process according to claim 1 comprising:
(a₅)
(i) contacting a nucleophilic compound selected from the group consisting of aniline, substituted aniline derivatives, aliphatic amines, substituted aliphatic amine derivatives, amides and substituted aromatic amines having at least two —NH₂ groups with a substituted aromatic azo compound or azoxy or hydrazo derivatives thereof in the presence of a suitable solvent system, and (ii) reacting said nucleophilic compound and said substituted aromatic azo compound or azoxy or hydrazo derivatives thereof in the presence of a suitable base and a controlled amount of protic material at a reaction temperature of about 70° C. to about 200° C. to produce a substituted aromatic amine having at least two —NH₂ groups, wherein the molar ratio of protic material to base is 0:1 to about 5:1, wherein the substituted aromatic azo compound is selected from the group consisting of compounds represented by the formula:

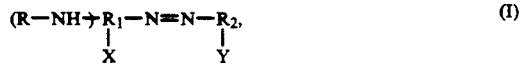

compounds represented by the formula:

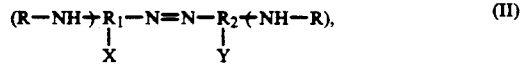

compounds represented by the formula:

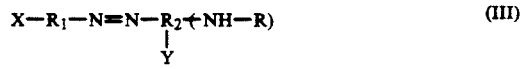

and mixtures thereof, wherein R—NH— represents a substituent derived from an amide or a substituted aromatic amine having at least two —NH₂ groups, wherein said amide is selected from the group consisting of diamides, substituted aliphatic amides represented by the formula

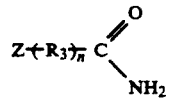

and substituted aromatic amides containing at least one substituent on the aromatic ring selected from the group consisting of —NH₂ and alkyl, aryl, aralkyl and alkaryl groups containing at least one —NH₂ group, wherein n is 0 or 1, R₃ is selected from the group consisting of alkyl, aralkyl, alkenyl, aralkenyl, cycloalkyl and cycloalkenyl groups, Z is selected from the group consisting of —NH₂ and alkyl, aryl, aralkyl and alkaryl groups containing at least one —NH₂ group, R₁ is an aromatic group, R₂ is selected from the group consisting of aliphatic and aromatic groups, and X and Y are independently selected from the group consisting of hydrogen, halides, —NO$_2$, —NH$_2$, aryl groups, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected from the group consisting of aliphatic and aromatic groups, halides are selected from the group consisting of chlorine, bromine and fluorine and R$_2$ is an aromatic group in substituted aromatic azo compounds (II) and (III);

(b) recovering said substituted aromatic amine having at least two —NH$_2$ groups, and (c)
  (i) contacting CO$_2$ and said substituted aromatic amine having at least two —NH$_2$ groups in the presence of an aprotic organic solvent and an organic, nitrogenous base, under reaction conditions of time and temperature sufficient to produce the corresponding ammonium carbamate salt, and
  (ii) reacting said ammonium carbamate salt with an electrophilic or oxophilic dehydrating agent selected from the group consisting of POX′$_3$, PX′$_3$, SOX′$_2$, SO$_2$X′$_2$, SO$_3$, PX′$_5$, P$_2$O$_5$, NO$_y$, NOX′, ketene, acid anhydrides having the formula:

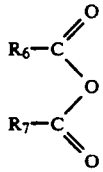

acid halides having the formula

and halides or oxyhalides of metals selected from the group consisting of transition metals, Group 111 B metals, Group IV B metals, and Group V B metals, and mixtures thereof wherein R$_6$ and R$_7$ are independently selected from the group consisting of fluoroalkyl, alkyl, aryl, alkaryl and aralkyl radicals having 1 to about 22 carbon atoms, X′ is chlorine or bromine, halides are chlorides or bromides, and y is 1 or 2 under reaction conditions of time and temperature sufficient to produce the corresponding isocyanate having at least two —N=C=O groups.

8. The process according to claim 1 comprising:

(a$_6$)
  (i) contacting a nucleophilic compound selected from the group consisting of aniline, substituted aniline derivatives, aliphatic amines, substituted aliphatic amine derivatives, amides and substituted aromatic amines having at least two —NH$_2$ groups with a substituted aromatic azo compound or azoxy or hydrazo derivatives thereof in the presence of a suitable solvent system,
  (ii) reacting said nucleophilic compound and said substituted aromatic azo compound or azoxy or hydrazo derivatives thereof in the presence of a suitable base and a controlled amount of protic material at a reaction temperature of about 70° C. to about 200° C. to produce a substituted aromatic amine containing an aromatic amide bond, wherein the molar ratio of protic material to base is 0:1 to about 5:1, wherein the substituted aromatic azo compound is selected from the group consisting of compounds represented by the formula:

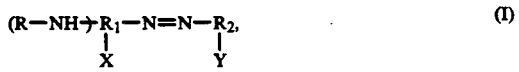

compounds represented by the formula:

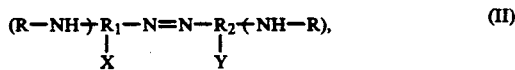

compounds represented by the formula:

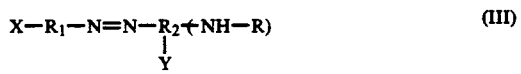

and mixtures thereof, wherein R—NH— represents a substituent derived from an amide, R$_1$ is an aromatic group, R$_2$ is selected from the group consisting of aliphatic and aromatic groups, and X and Y are independently selected from the group consisting of hydrogen, halides, —NO$_2$, —NH$_2$, aryl groups, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected from the group consisting of aliphatic and aromatic groups, halides are selected from the group consisting of chlorine, bromine and fluorine and R$_2$ is an aromatic group in substituted aromatic azo compounds (II) and (III), and (iii) reacting said substituted aromatic amine of (a$_6$)(ii) with ammonia under conditions which produce the corresponding substituted aromatic amine having at least two —NH$_2$ groups and amide;

(b) recovering said substituted aromatic amine having at least two —NH$_2$ groups, and (c)
  (i) contacting CO$_2$ and said substituted aromatic amine having at least two —NH$_2$ groups in the presence of an aprotic organic solvent and an organic, nitrogenous base, under reaction conditions of time and temperature sufficient to produce the corresponding ammonium carbamate salt, and
  (ii) reacting said ammonium carbamate salt with an electrophilic or oxophilic dehydrating agent selected from the group consisting of POX′$_3$, PX′$_3$, SOX′$_2$, SO$_2$X′$_2$, SO$_3$, PX′$_5$, P$_2$O$_5$, NO$_y$, NOX′, ketene, acid anhydrides having the formula:

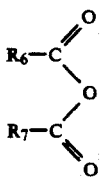

acid halides having the formula

and halides or oxyhalides of metals selected from the group consisting of transition metals, Group III B metals, Group IV B metals, and Group V B metals, and mixtures thereof wherein $R_6$ and $R_7$ are independently selected from the group consisting of fluoroalkyl, alkyl, aryl, alkaryl and aralkyl radicals having 1 to about 22 carbon atoms, X' is chlorine or bromine, halides are chlorides or bromides, and y is 1 or 2 under reaction conditions of time and temperature sufficient to produce the corresponding isocyanate having at least two —N=C=O groups.

9. The process according to claim 1 comprising:
(a₇)
  (i) contacting a substituted aniline derivative, wherein the substituents are selected from the group consisting of halide, —NO₂, —NH₂, alkyl groups, alkoxy groups, —SO₃, —COOR₃₀ and aryl, aralkyl or alkaryl groups containing at least one —NH₂ group provided said substituted aniline derivative contains at least one substituent selected from the group consisting of —NO₂, —NH₂ and aryl, aralkyl or alkaryl groups containing at least one —NH₂ group, and nitrobenzene in a suitable solvent system, $R_{30}$ is selected from the group consisting of aliphatic and aromatic groups,
  (ii) reacting said substituted aniline derivative and nitrobenzene in a confined reaction zone at a suitable temperature, and in the presence of a suitable base and a controlled amount of protic material, and
  (iii) reducing the reaction product of (a₇)(ii) under conditions to produce a substituted aromatic amine having at least two —NH₂ groups,
(b) recovering said substituted aromatic amine having at least two —NH₂ groups, and
(c)
  (i) contacting CO₂ and said substituted aromatic amine having at least two —NH₂ groups in the presence of an aprotic organic solvent and an organic, nitrogenous base, under reaction conditions of time and temperature sufficient to produce the corresponding ammonium carbamate salt, and
  (ii) reacting said ammonium carbamate salt with an electrophilic or oxophilic dehydrating agent selected from the group consisting of POX'₃, PX'₃, SOX'₃, SO₂X'₂, SO₃, PX'₅, P₂O₅, NO$_y$, NOX', ketene, acid anhydrides having the formula:

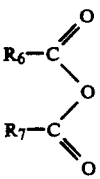

acid halides having the formula

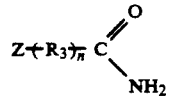

and halides or oxyhalides of metals selected from the group consisting of transition metals, Group III B metals, Group IV B metals, and Group V B metals, and mixtures thereof wherein $R_6$ and $R_7$ are independently selected from the group consisting of fluoroalkyl, alkyl, aryl, alkaryl and aralkyl radicals having 1 to about 22 carbon atoms, X' is chlorine or bromine, halides are chlorides or bromides, and y is 1 or 2 under reaction conditions of time and temperature sufficient to produce the corresponding isocyanate having at least two —N=C=O groups.

10. The process according to claim 1 comprising:
(a)
  (i) contacting an amide selected from the group consisting of diamides, substituted aliphatic amides represented by the formula $$Z \pm R_3 \pm_n C \underset{NH_2}{\overset{O}{\diagup \diagdown}}$$

and substituted aromatic amides containing at least one substituent on the aromatic ring selected from the group consisting of —NO₂, —NH₂ and alkyl, aryl, aralkyl, and alkaryl groups containing at least one —NH₂ group, and nitrobenzene in the presence of a suitable solvent system wherein n is 0 or 1, $R_3$ is selected from the group consisting of alkyl, aralkyl, alkenyl, aralkenyl, cycloalkyl and cyloalkenyl groups, and Z is selected from the group consisting of —NO₂, —NH₂ and alkyl, aryl, aralkyl and alkaryl groups containing at least one —NH₂ group,
  (ii) reacting said amide of (a)(i) and nitrobenzene in the presence of a suitable base and a controlled amount of protic material at a suitable temperature in a confined reaction zone, and
  (iii) reducing the reaction product of (a)(ii) under conditions which produce a substituted aromatic amine having at least two —NH₂ groups;
(b) recovering said substituted aromatic amine having at least two —NH₂ groups, and
(c₁)
  (i) contacting CO₂ and said substituted aromatic amine having at least two —NH₂ groups in the presence of an organic, nitrogenous base selected form the group consisting of guanidine compounds, amidine compounds, phosphazene compounds and mixtures thereof, under reaction conditions of time and temperature sufficient to produce the corresponding ammonium carbamate salt, (ii) reacting, in a polar aprotic solvent, said salt with a primary or secondary hydrocarbyl halide under reaction conditions of time and temperature sufficient to produce the corresponding carbamate ester, and (iii) cracking said carbamate ester under conditions to produce the corresponding isocyanate having at least two —N═C═O groups.

11. The process according to claim 1 comprising:
(a₁)
  (i) contacting an amide and nitrobenzene in the presence of a suitable solvent system,
  (ii) reacting said amide of (a₁)(i) and nitrobenzene in the presence of a suitable base and a controlled amount of protic material at a suitable temperature in a confined reaction zone to produce a p-nitroaromatic amide,
  (iii) reducing said p-nitroaromatic amide of (a₁)(ii) under conditions which produce a p-aminoaromatic amide, and
  (iv) reacting said p-aminoaromatic amide with ammonia under conditions which produce the corresponding substituted aromatic amine having at least two —NH₂ groups and amide;
(b) recovering said substituted aromatic amine having at least two —NH₂ groups, and
(c₁)
  (i) contacting CO₂ and said substituted aromatic amine having at least two —NH₂ groups in the presence of an organic, nitrogenous base selected form the group consisting of guanidine compounds, amidine compounds, phosphazene compounds and mixtures thereof, under reaction conditions of time and temperature sufficient to produce the corresponding ammonium carbamate salt,
  (ii) reacting, in a polar aprotic solvent, said salt with a primary or secondary hydrocarbyl halide under reaction conditions of time and temperature sufficient to produce the corresponding carbamate ester, and
  (iii) cracking said carbamate ester under conditions to produce the corresponding isocyanate having at least two —N═C═O groups.

12. The process according to claim 1 comprising:
(a₂)
  (i) contacting an amide and nitrobenzene in the presence of a suitable solvent system,
  (ii) reacting said amide of (a₂)(i) and nitrobenzene in the presence of a suitable base and a controlled amount of protic material at a suitable temperature in a confined reaction zone to produce a p-nitroaromatic amide,
  (iii) reacting said p-nitroaromatic amide of (a₂)(ii) with ammonia under conditions which produce the corresponding p-nitroaromatic amine and amide, and
  (iv) reducing said p-nitroaromatic amine under conditions which produce the corresponding substituted aromatic amine having at least two —NH₂ groups;
(b) recovering said substituted aromatic amine having at least two —NH₂ groups, and
(c₁)
  (i) contacting CO₂ and said substituted aromatic amine having at least two —NH₂ groups in the presence of an organic, nitrogenous base selected form the group consisting of guanidine compounds, amidine compounds, phosphazene compounds and mixtures thereof, under reaction conditions of time and temperature sufficient to produce the corresponding ammonium carbamate salt,
  (ii) reacting, in a polar aprotic solvent, said salt with a primary or secondary hydrocarbyl halide under reaction conditions of time and temperature sufficient to produce the corresponding carbamate ester, and
  (iii) cracking said carbamate ester under conditions to produce the corresponding isocyanate having at least two —N═C═O groups.

13. The process according to claim 1 comprising:
(a₃)
  (i) contacting an amide or a substituted aromatic amine having at least two —NH₂ groups, wherein said amide is selected from the group consisting of diamides, substituted aliphatic amides represented by the formula

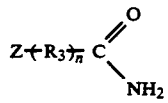

and substituted aromatic amides containing at least one substituent on the aromatic ring selected from the group consisting of —NH₂ and alkyl, aryl, aralkyl and alkaryl groups containing at least one —NH₂ group, and an azo containing compound represented by the formula X—R₁—N═N—R₂—Y or azoxy or hydrazo derivatives thereof in the presence of a suitable solvent system wherein is 0 or 1, R₃ is selected from the group consisting of alkyl, aralkyl, alkenyl, aralkenyl, cycloalkyl and cycloalkenyl groups, Z is selected from the group consisting of —NH₂ and alkyl, aryl, aralkyl and alkaryl groups containing at least one —NH₂ group, R₁ is an aromatic group, R₂ is selected from the group consisting of aliphatic and aromatic groups, and X and Y are independently selected from the group consisting of hydrogen, halides, —NO₂, —NH₂, aryl groups, alkyl groups, alkoxy groups, —SO₃, —SO₃R₃₀, —OR₃₀, —COOR₃₀, and alkyl, aryl, aralkyl or alkaryl groups containing at least one —NH₂ group, wherein R₃₀ is selected from the group consisting of aliphatic and aromatic groups, if R₂ is aliphatic, X is in the meta or ortho position on R₁ and if R₂ is aromatic, at least one of X and Y is in the meta or ortho position on R₁ and R₂, respectively, and wherein halides are selected from the group consisting of chloride, bromide and fluoride,
  (ii) reacting said amide or said substituted aromatic amine having at least two —NH₂ groups of (a₃)(i) and said azo containing compound in the presence of a suitable base and a controlled amount of protic material at a reaction temperature of about 10° C. to about 150° C. in a confined reaction zone to produce a substituted aromatic azo compound wherein the molar ratio of protic material to base is 0:1 to about 5:1, and (iii) reacting said substituted aromatic azo compound of (a₃)(ii) with a nucleophilic compound selected from the group consisting of aniline, substituted aniline derivatives, aliphatic amines, substituted aliphatic amine derivatives, amides and substituted aromatic amines having at least two —NH₂ groups in the presence of a suitable solvent system, a suitable base and a controlled amount of protic material at a reaction temperature of about 70° C. to about 200° C. in a confined reaction zone to produce a substituted aromatic amine having at least two —NH₂ groups, wherein the molar ratio of protic material to base is 0:1 to about 5:1;

(b) recovering said substituted aromatic amine having at least two —NH₂ groups, and (c₁)
(i) contacting CO₂ and said substituted aromatic amine having at least two —NH₂ groups in the presence of an organic, nitrogenous base selected form the group consisting of guanidine compounds, amidine compounds, phosphazene compounds and mixtures thereof, under reaction conditions of time and temperature sufficient to produce the corresponding ammonium carbamate salt, (ii) reacting, in a polar aprotic solvent, said salt with a primary or secondary hydrocarbyl halide under reaction conditions of time and temperature sufficient to produce the corresponding carbamate ester, and (iii) cracking said carbamate ester under conditions to produce the corresponding isocyanate having at least two —N=C=O groups.

14. The process according to claim 1 comprising:

(a₄)
(i) contacting an amide and an azo containing compound represented by the formula X—R₁—N=N—R₂—Y or azoxy or hydrazo derivatives thereof in the presence of a suitable solvent system, wherein R₁ is an aromatic group, R₂ is selected from the group consisting of aliphatic and aromatic groups, and X and Y are independently selected from the group consisting of hydrogen, halides, —NO₂, —NH₂, aryl groups, alkyl groups, alkoxy groups, —SO₃, —SO₃R₃₀, —OR₃₀, —COOR₃₀, and alkyl, aryl, aralkyl or alkaryl groups containing at least one —NH₂ group, wherein R₃₀ is selected from the group consisting of aliphatic and aromatic groups, if R₂ is aliphatic, X is in the meta or ortho position on R₁ and if R₂ is aromatic, at least one of X and Y is in the meta or ortho position on R₁ and R₂, respectively, and wherein halides are selected from the group consisting of chloride, bromide and fluoride, (ii) reacting said amide of (a₄)(i) and said azo containing compound in the presence of a suitable base and a controlled amount of protic material at a reaction temperature of about 10° C. to about 150° C. in a confined reaction zone to produce a substituted aromatic azo compound, wherein the molar ratio of protic material to base is 0:1 to about 5:1, (iii) reacting said substituted aromatic azo compound of (a₄)(ii) with a nucleophilic compound selected from the group consisting of aniline, substituted aniline derivatives, aliphatic amines, substituted aliphatic amine derivatives, amides and substituted aromatic amines having at least two —NH₂ groups in the presence of a suitable solvent system, a suitable base and a controlled amount of protic material at a reaction temperature of about 70° C. to about 200° C. in a confined reaction zone to produce a substituted aromatic amine containing an aromatic amide bond wherein the molar ratio of protic material to base is 0:1 to about 5:1, and (iv) reacting said substituted aromatic amine of (a₄)(iii) with ammonia under conditions which produce the corresponding substituted aromatic amine having at least two —NH₂ groups and amide;

(b) recovering said substituted aromatic amine having at least two —NH₂ groups, and (c₁)
(i) contacting CO₂ and said substituted aromatic amine having at least two —NH₂ groups in the presence of an organic, nitrogenous base selected form the group consisting of guanidine compounds, amidine compounds, phosphazene compounds and mixtures thereof, under reaction conditions of time and temperature sufficient to produce the corresponding ammonium carbamate salt, (ii) reacting, in a polar aprotic solvent, said salt with a primary or secondary hydrocarbyl halide under reaction conditions of time and temperature sufficient to produce the corresponding carbamate ester, and (iii) cracking said carbamate ester under conditions to produce the corresponding isocyanate having at least two —N=C=O groups.

15. The process according to claim 1 comprising:

(a₅)
(i) contacting a nucleophilic compound selected from the group consisting of aniline, substituted aniline derivatives, aliphatic amines, substituted aliphatic amine derivatives, amides and substituted aromatic amines having at least two —NH₂ groups with a substituted aromatic azo compound or azoxy or hydrazo derivatives thereof in the presence of a suitable solvent system, and (ii) reacting said nucleophilic compound and said substituted aromatic azo compound or azoxy or hydrazo derivatives thereof in the presence of a suitable base and a controlled amount of protic material at a reaction temperature of about 70° C. to about 200° C. to produce a substituted aromatic amine having at least two —NH₂ groups, wherein the molar ratio of protic material to base is 0:1 to about 5:1, wherein the substituted aromatic azo compound is selected from the group consisting of compounds represented by the formula:

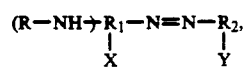 (I)

compounds represented by the formula:

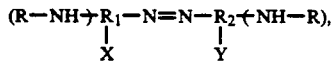   (II)

compounds represented by the formula:

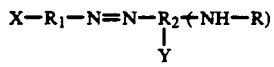   (III)

and mixtures thereof, wherein R—NH— represents a substituent derived from an amide or a substituted aromatic amine having at least two —NH$_2$ groups, wherein said amide is selected from the group consisting of diamides, substituted aliphatic amides represented by the formula

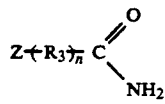

and substituted aromatic amides containing at least one substituent on the aromatic ring selected from the group consisting of —NH$_2$ and alkyl, aryl, aralkyl and alkaryl groups containing at least one —NH$_2$ group, wherein n is 0 or 1, R$_3$ is selected from the group consisting of alkyl, aralkyl, alkenyl, aralkenyl, cycloalkyl and cycloalkenyl groups, Z is selected from the group consisting of —NH$_2$ and alkyl, aryl, aralkyl and alkaryl groups containing at least one —NH$_2$ group, R$_1$ is an aromatic group, R$_2$ is selected from the group consisting of aliphatic and aromatic groups, and X and Y are independently selected from the group consisting of hydrogen, halides, —NO$_2$, —NH$_2$, aryl groups, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected from the group consisting of aliphatic and aromatic groups, halides are selected from the group consisting of chlorine, bromine and fluorine and R$_2$ is an aromatic group in substituted aromatic azo compounds (II) and (III);

(b) recovering said substituted aromatic amine having at least two —NH$_2$ groups, and (c$_1$)
  (i) contacting CO$_2$ and said substituted aromatic amine having at least two —NH$_2$ groups in the presence of an organic, nitrogenous base selected form the group consisting of guanidine compounds, amidine compounds, phosphazene compounds and mixtures thereof, under reaction conditions of time and temperature sufficient to produce the corresponding ammonium carbamate salt,
  (ii) reacting, in a polar aprotic solvent, said salt with a primary or secondary hydrocarbyl halide under reaction conditions of time and temperature sufficient to produce the corresponding carbamate ester, and (iii) cracking said carbamate ester under conditions to produce the corresponding isocyanate having at least two —N=C=O groups.

16. The process according to claim 1 comprising:
(a$_6$)
  (i) contacting a nucleophilic compound selected from the group consisting of aniline, substituted aniline derivatives, aliphatic amines, substituted aliphatic amine derivatives, amides and substituted aromatic amines having at least two —NH$_2$ groups with a substituted aromatic azo compound or azoxy or hydrazo derivatives thereof in the presence of a suitable solvent system,
  (ii) reacting said nucleophilic compound and said substituted aromatic azo compound or azoxy or hydrazo derivatives thereof in the presence of a suitable base and a controlled amount of protic material at a reaction temperature of about 70° C. to about 200° C. to produce a substituted aromatic amine containing an aromatic amide bond, wherein the molar ratio of protic material to base is 0:1 to about 5:1, wherein the substituted aromatic azo compound is selected from the group consisting of compounds represented by the formula:

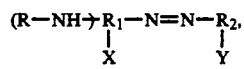   (I)

compounds represented by the formula:

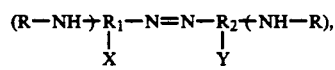   (II)

compounds represented by the formula:

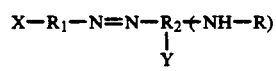   (III)

and mixtures thereof, wherein R—NH— represents a substituent derived from an amide, R$_1$ is an aromatic group, R$_2$ is selected from the group consisting of aliphatic and aromatic groups, and X and Y are independently selected from the group consisting of hydrogen, halides, —NO$_2$, —NH$_2$, aryl groups, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected from the group consisting of aliphatic and aromatic groups, halides are selected from the group consisting of chlorine, bromine and fluorine and R$_2$ is an aromatic group in substituted aromatic azo compounds (II) and (III), and (iii) reacting said substituted aromatic amine of (a$_6$)(ii) with ammonia under conditions which produce the corresponding substituted aromatic amine having at least two —NH$_2$ groups and amide;

(b) recovering said substituted aromatic amine having at least two —NH$_2$ groups, and (c$_1$)
  (i) contacting CO$_2$ and said substituted aromatic amine having at least two —NH$_2$ groups in the presence of an organic, nitrogenous base selected form the group consisting of guanidine compounds, amidine compounds, phosphazene compounds and mixtures thereof, under reaction conditions of time and temperature sufficient to produce the corresponding ammonium carbamate salt, (ii) reacting, in a polar aprotic solvent, said salt with a primary or secondary hydrocarbyl halide under reaction conditions of time and temperature sufficient to produce the corresponding carbamate ester, and (iii) cracking said carbamate ester under conditions to produce the corresponding isocyanate having at least two —N=C=O groups.

17. The process according to claim 1 comprising:
(a$_7$)
(i) contacting a substituted aniline derivative, wherein the substituents are selected from the group consisting of halide, —NO$_2$, —NH$_2$, alkyl groups, alkoxy groups, —SO$_3$, —COOR$_{30}$ and aryl, aralkyl or alkaryl groups containing at least one —NH$_2$ group provided said substituted aniline derivative contains at least one substituent selected from the group consisting of —NO$_2$, —NH$_2$ and aryl, aralkyl or alkaryl groups containing at least one —NH$_2$ group, and nitrobenzene in a suitable solvent system, wherein R$_{30}$ is selected from the group consisting of aliphatic and aromatic groups, (ii) reacting said substituted aniline derivative and nitrobenzene in a confined reaction zone at a suitable temperature, and in the presence of a suitable base and a controlled amount of protic material, and (iii) reducing the reaction product of (a$_7$)(ii) under conditions to produce a substituted aromatic amine having at least two —NH$_2$ groups, (b) recovering said substituted aromatic amine having at least two —NH$_2$ groups, and (c$_1$)
(i) contacting CO$_2$ and said substituted aromatic amine having at least two —NH$_2$ groups in the presence of an organic, nitrogenous base selected form the group consisting of guanidine compounds, amidine compounds, phosphazene compounds and mixtures thereof, under reaction conditions of time and temperature sufficient to produce the corresponding ammonium carbamate salt, (ii) reacting, in a polar aprotic solvent, said salt with a primary or secondary hydrocarbyl halide under reaction conditions of time and temperature sufficient to produce the corresponding carbamate ester, and (iii) cracking said carbamate ester under conditions to produce the corresponding isocyanate having at least two —N=C=O groups.

18. The process according to claim 1 wherein said diamide of Step (a) is represented by the formula:

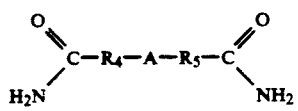

and R$_4$ and R$_5$ are independently selected from the group consisting of aromatic groups, aliphatic groups and a direct bond, and A is selected from the group consisting of

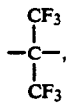

—SO$_2$—, —O—, —S— and a direct bond.

19. The process according to claim 1 wherein said suitable solvent system of Step (a) includes a solvent selected from the group consisting of nitrobenzene, dimethylsulfoxide, dimethylformamide, N-methyl-2-pyrrolidone, pyridine, N-methylaniline, chlorobenzene, tetraalkyl ammonium hydroxide or amides having a melting point below the reaction temperature and mixtures thereof.

20. The process according to claim 1 wherein the molar ratio of said protic material to said suitable base in Step (a) is less than about 5:1 and the ratio of equivalents of said suitable base to equivalents of said amide in Step (a) is about 1:1 to about 10:1.

21. The process according to claim 1 wherein said suitable base of Step (a) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

22. The process according to claim 1 wherein said amide of Step (a$_1$) is selected from the group consisting of aromatic amides, aliphatic amides, substituted aromatic amide derivatives, substituted aliphatic amide derivatives and diamides having the formula:

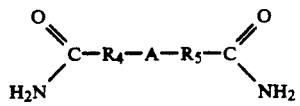

wherein R$_4$ and R$_5$ are independently selected from the group consisting of aromatic groups, aliphatic groups and a direct bond, and A is selected from the group consisting of

—SO$_2$—, —O—, —S— and a direct bond, said aliphatic amides and said substituted aliphatic amide derivatives are represented by the formula:

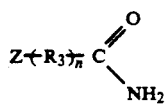

wherein n is 0 or 1, R$_3$ is selected from the group consisting of alkyl, aralkyl, alkenyl, aralkenyl, cycloalkyl and cycloalkenyl groups and Z is selected from the group consisting of hydrogen, —NO$_2$, —NH$_2$, aryl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, and the substituent of said substituted aromatic amide derivatives is selected from the group consisting of halide, —NO$_2$, —NH$_2$, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected from the group consisting of aliphatic and aromatic groups, halides are selected from the group consisting of chloride, bromide and fluoride.

23. The process according to claim 1 wherein said suitable solvent system of Step (a$_1$) includes a solvent selected from the group consisting of nitrobenzene, dimethylsulfoxide, dimethylformamide, N-methyl-2-pyrrolidone, pyridine, N-methylaniline, chlorobenzene, tetraalkyl ammonium hydroxide or amides having a melting point below the reaction temperature and mixtures thereof.

24. The process according to claim 1 wherein the molar ratio of said protic material to said suitable base in Step (a$_1$) is less than about 5:1 and the ratio of equivalents of said suitable base to equivalents of said amide in Step (a) is about 1:1 to about 10:1.

25. The process according to claim 1 wherein said suitable base of Step (a$_1$) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

26. The process according to claim 1 wherein said amide of Step (a$_2$) is selected from the group consisting of aromatic amides, aliphatic amides, substituted aromatic amide derivatives, substituted aliphatic amide derivatives and diamides having the formula:

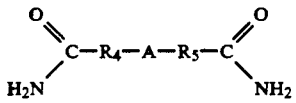

wherein R$_4$ and R$_5$ are independently selected from the group consisting of aromatic groups, aliphatic groups and a direct bond, and A is selected from the group consisting of

—SO$_2$—, —O—, —S— and a direct bond, said aliphatic amides and said substituted aliphatic amide derivatives are represented by the formula:

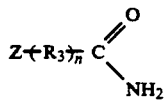

wherein n is 0 or 1, R$_3$ is selected from the group consisting of alkyl, aralkyl, alkenyl, aralkenyl, cycloalkyl and cycloalkenyl groups and Z is selected from the group consisting of hydrogen, —NO$_2$, —NH$_2$, aryl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, and the substituent of said substituted aromatic amide derivatives is selected from the group consisting of halide, —NO$_2$, —NH$_2$, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected from the group consisting of aliphatic and aromatic groups, halides are selected from the group consisting of chloride, bromide and fluoride.

27. The process according to claim 1 wherein said suitable solvent system of Step (a$_2$) includes a solvent selected from the group consisting of nitrobenzene, dimethylsulfoxide, dimethylformamide, N-methyl-2-pyrrolidone, pyridine, N-methylaniline, chlorobenzene, tetraalkyl ammonium hydroxide or amides having a melting point below the reaction temperature and mixtures thereof.

28. The process according to claim 1 wherein the molar ratio of said protic material to said suitable base in Step (a$_2$) is less than about 5:1 and the ratio of equivalents of said suitable base to equivalents of said amide in Step (a) is about 1:1 to about 10:1.

29. The process according to claim 1 wherein said suitable base of Step (a$_2$) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

30. The process according to claim 1 wherein said diamide of Step (a$_3$) is represented by the formula:

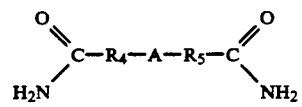

wherein R$_4$ and R$_5$ are independently selected from the group consisting of aromatic groups, aliphatic groups and a direct bond, and A is selected from the group consisting of

—SO$_2$—, —O—, —S— and a direct bond.

31. The process according to claim 1 wherein said suitable solvent system of Step (a$_3$) includes a solvent selected from the group consisting of aniline, dimethylsulfoxide, dimethylformamide, N-methyl-2-pyrrolidone, pyridine, ethylene glycol dimethyl ether, diisopropylamine, molten benzamide and mixtures thereof.

32. The process according to claim 1 wherein said suitable base of Step (a$_3$) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

33. The process according to claim 1 wherein said amide of Step (a4) is selected from the group consisting of aromatic amides, aliphatic amides, substituted aromatic amide derivatives, substituted aliphatic amide derivatives and diamides having the formula:

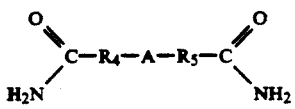

wherein $R_4$ and $R_5$ are independently selected from the group consisting of aromatic groups, aliphatic groups and a direct bond, and A is selected from the group consisting of

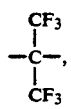

$-SO_2-$, $-O-$, $-S-$ and a direct bond, said aliphatic amides and said substituted aliphatic amide derivatives are represented by the formula:

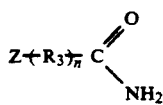

wherein n is 0 or 1, $R_3$ is selected from the group consisting of alkyl, aralkyl, alkenyl, aralkenyl, cycloalkyl and cycloalkenyl groups and Z is selected from the group consisting of hydrogen, $-NO_2$, $-NH_2$, aryl groups, alkoxy groups, $-SO_3$, $-SO_3R_{30}$, $-OR_{30}$, $-COOR_{30}$, and alkyl, aryl, aralkyl or alkaryl groups containing at least one $-NH_2$ group, and the substituent of said substituted aromatic amide derivatives is selected from the group consisting of halide, $-NO_2$, $-NH_2$, alkyl groups, alkoxy groups, $-SO_3$, $-SO_3R_{30}$, $-OR_{30}$, $-COOR_{30}$, and alkyl, aryl, aralkyl or alkaryl groups containing at least one $-NH_2$ group, wherein $R_{30}$ is selected from the group consisting of aliphatic and aromatic groups, and halides are selected from the group consisting of chloride, bromide and fluoride.

34. The process according to claim 1 wherein said suitable solvent system of Step (a4) includes a solvent selected from the group consisting of aniline, dimethylsulfoxide, dimethylformamide, N-methyl-2-pyrrolidone, pyridine, ethylene glycol dimethyl ether, diisopropylamine, molten benzamide and mixtures thereof.

35. The process according to claim 1 wherein said suitable base of Step (a4) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

36. The process according to claim 1 wherein said suitable solvent system of Step (a5) includes a solvent selected from the group consisting of aniline, dimethylsulfoxide, dimethylformamide, N-methyl-2-pyrrolidone, pyridine, ethylene glycol dimethyl ether, diisopropylamine, molten benzamide and mixtures thereof.

37. The process according to claim 1 wherein said suitable base of Step (a5) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

38. The process according to claim 1 wherein said diamide of Step (a5)(ii) is represented by the formula:

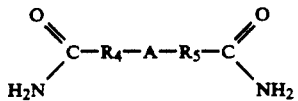

wherein $R_4$ and $R_5$ are independently selected from the group consisting of aromatic groups, aliphatic groups and a direct bond, and A is selected from the group consisting of

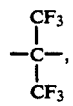

$-SO_2-$, $-O-$, $-S-$ and a direct bond.

39. The process according to claim 1 wherein said suitable solvent system of Step (a6) includes a solvent selected from the group consisting of aniline, dimethylsulfoxide, dimethylformamide, N-methyl-2-pyrrolidone, pyridine, ethylene glycol dimethyl ether, diisopropylamine, molten benzamide and mixtures thereof.

40. The process according to claim 1 wherein said suitable base of Step (a6) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

41. The process according to claim 1 wherein said amide of Step (a6) is selected from the group consisting of aromatic amides, aliphatic amides, substituted aromatic amide derivatives, substituted aliphatic amide derivatives and diamides having the formula:

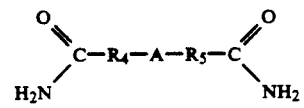

wherein $R_4$ and $R_5$ are independently selected from the group consisting of aromatic groups, aliphatic groups and a direct bond, and A is selected from the group consisting of

—SO$_2$—, —O—, —S— and a direct bond, said aliphatic amides and said substituted aliphatic amide derivatives are represented by the formula:

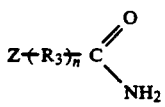

wherein n is 0 or 1, R$_3$ is selected from the group consisting of alkyl, aralkyl, alkenyl, aralkenyl, cycloalkyl and cycloalkenyl groups and Z is selected from the group consisting of hydrogen, —NO$_2$, —NH$_2$, aryl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, and the substituent of said substituted aromatic amide derivatives is selected from the group consisting of halide, —NO$_2$, —NH$_2$, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected from the group consisting of aliphatic and aromatic groups, and halides are selected from the group consisting of chloride, bromide and fluoride.

42. The process according to claim 1 wherein said suitable solvent system of Step (a$_7$) includes a solvent selected from the group consisting of nitrobenzene, dimethylsulfoxide, dimethylformamide, N-methyl-2-pyrrolidone, pyridine, toluene, hexane, ethylene glycol dimethyl ether, diisopropylethylamine and mixtures thereof.

43. The process according to claim 1 wherein the molar ratio of said protic material to said suitable base in Step (a$_7$) is less than about 6:1.

44. The process according to claim 1 wherein said suitable base of Step (a$_7$) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

45. The process according to claim 1 wherein said aprotic organic solvent of Step (c) is selected from the group consisting of dichloromethane, tetrahydrofuran, acetonitrile, o-dichlorobenzene, toluene, N,N-dimethylacetamide and pyridine.

46. The process according to claim 1 wherein said organic, nitrogenous base of Step (c) is selected from the group consisting of guanidine compounds, amidine compounds, phosphazene compounds, tertiary amines, pyridine and mixtures thereof.

47. The process according to claim 1 wherein said aprotic organic solvent of Step (c) is present in at least an amount sufficient to solubilize said ammonium carbamate salt of Step (c), and the ratio of the number of moles of said organic, nitrogenous base of Step (c) to the number of equivalents of amine in said substituted aromatic amine of Step (c) is 1:1 to about 20:1.

48. The process according to claim 1 wherein the ratio of the number of moles of said electrophilic or oxophilic dehydrating agent of Step (c) to the number of equivalents of amine in said substituted aromatic amine of Step (c) is about 0.4:1 to about 10:1.

49. The process according to claim 1 wherein said polar aprotic solvent of Step (c$_1$) is selected from the group consisting of dimethylsulfoxide, dimethylformamide, acetonitrile and N-methyl-2-pyrrolidone.

50. The process according to claim 1 wherein said primary or secondary hydrocarbyl halide of Step (c$_1$) is represented by the formula R'X'' or X''R'X'', wherein R' represents alkyl, alkenyl, cycloalkyl, cycloalkenyl, aralkyl and aralkenyl radicals having 1 to about 22 carbon atoms, provided that R's not a tertiary radical of the formula (R)$_3$C— or (R)$_2$C=C(R)—; and X'' represents a halide.

51. The process according to claim 1 further comprising:
(d) recovering said isocyanate having at least two —N=C=O groups, and
(e) contacting said isocyanate having at least two —N=C=O groups with a dicarboxylic acid in the presence of a suitable solvent system and a suitable base under polymerization conditions of time and temperature sufficient to produce the corresponding polyamide provided that said suitable base is optional when said suitable solvent functions as a suitable base.

52. The process according to claim 51 wherein said suitable solvent system includes a solvent selected from the group consisting of linear or cyclic amides, phosphoryl amides, sulfoxides, sulfones, N,N'-dimethylalkyleneureas and mixtures thereof.

53. The process according to claim 51 wherein said suitable base is selected from the group consisting of alkali metal hydroxides alkali metal carbonates, alkali metal bicarbonates, alkali metal alkoxides, alkali metal phenoxides, tertiary amines and mixtures thereof.

54. The process according to claim 1 further comprising:
(d) recovering said isocyanate having at least two —N=C=O groups, and
(e) contacting said isocyanate having at least two —N=C=O groups with a salt of a dicarboxylic acid in the presence of a suitable solvent system under polymerization conditions of time and temperature sufficient to produce the corresponding polyamide.

55. The process according to claim 54 wherein said suitable solvent system includes a solvent selected from the group consisting of linear or cyclic amides, phosphoryl amides, sulfoxides, sulfones, N,N'-dimethylalkyleneureas and mixtures thereof.

56. The process according to claim 54 wherein the polymerization reaction mixture of Step (e) further comprises a base.

57. The process according to claim 56 wherein said suitable base is selected from the group consisting of alkali metal hydroxides alkali metal carbonates, alkali metal bicarbonates, alkali metal alkoxides, alkali metal phenoxides, tertiary amines and mixtures thereof.

58. A process for preparing a carbamate ester having at least two

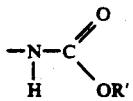

groups comprising:
(a)
(i) contacting an amide selected from the group consisting of diamides, substituted aliphatic amides represented by the formula

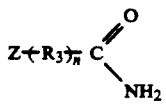

and substituted aromatic amides containing at least one substituent on the aromatic ring selected from the group consisting of $-NO_2$, $-NH_2$ and alkyl, aryl, aralkyl, and alkaryl groups containing at least one $-NH_2$ group, and nitrobenzene in the presence of a suitable solvent system wherein n is 0 or 1, $R_3$ is selected from the group consisting of alkyl, aralkyl, alkenyl, aralkenyl, cycloalkyl and cyloalkenyl groups, and Z is selected from the group consisting of $-NO_2$, $-NH_2$ and alkyl, aryl, aralkyl and alkaryl groups containing at least one $-NH_2$ group, (ii) reacting said amide of (a)(i) and nitrobenzene in the presence of a suitable base and a controlled amount of protic material at a suitable temperature in a confined reaction zone, and (iii) reducing the reaction product of (a)(ii) under conditions which produce a substituted aromatic amine having at least two $-NH_2$ groups; or ($a_1$)
(i) contacting an amide and nitrobenzene in the presence of a suitable solvent system, (ii) reacting said amide of ($a_1$)(i) and nitrobenzene in the presence of a suitable base and a controlled amount of protic material at a suitable temperature in a confined reaction zone to produce a p-nitroaromatic amide, (iii) reducing said p-nitroaromatic amide of ($a_1$)(ii) under conditions which produce a p-aminoaromatic amide, and (iv) reacting said p-aminoaromatic amide with ammonia under conditions which produce the corresponding substituted aromatic amine having at least two $-NH_2$ groups and amide; or ($a_2$)
(i) contacting an amide and nitrobenzene in the presence of a suitable solvent system, (ii) reacting said amide of ($a_2$)(i) and nitrobenzene in the presence of a suitable base and a controlled amount of protic material at a suitable temperature in a confined reaction zone to produce a p-nitroaromatic amide, (iii) reacting said p-nitroaromatic amide of ($a_2$)(ii) with ammonia under conditions which produce the corresponding p-nitroaromatic amine and amide, and (iv) reducing said p-nitroaromatic amine under conditions which produce the corresponding substituted aromatic amine having at least two $-NH_2$ groups; or ($a_3$)
(i) contacting an amide or a substituted aromatic amine having at least two $-NH_2$ groups, wherein said amide is selected from the group consisting of diamides, substituted aliphatic amides represented by the formula

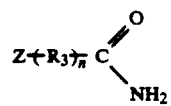

and substituted aromatic amides containing at least one substituent on the aromatic ring selected from the group consisting of $-NH_2$ and alkyl, aryl, aralkyl and alkaryl groups containing at least one $-NH_2$ group, and an azo containing compound represented by the formula $X-R_1-N=N-R_2-Y$ or azoxy or hydrazo derivatives thereof in the presence of a suitable solvent system wherein n is 0 or 1, $R_3$ is selected from the group consisting of alkyl, aralkyl, alkenyl, aralkenyl, cycloalkyl and cycloalkenyl groups, Z is selected from the group consisting of $-NH_2$ and alkyl, aryl, aralkyl and alkaryl groups containing at least one $-NH_2$ group, $R_1$ is an aromatic group, $R_2$ is selected from the group consisting of aliphatic and aromatic groups, and X and Y are independently selected from the group consisting of hydrogen, halides, $-NO_2$, $-NH_2$, aryl groups, alkyl groups, alkoxy groups, $-SO_3$, $-SO_3R_{30}$, $-OR_{30}$, $-COOR_{30}$, and alkyl, aryl, aralkyl or alkaryl groups containing at least one $-NH_2$ group, wherein $R_{30}$ is selected from the group consisting of aliphatic and aromatic groups, if $R_2$ is aliphatic, X is in the meta or ortho position on $R_1$ and if $R_2$ is aromatic, at least one of X and Y is in the meta or ortho position on $R_1$ and $R_2$, respectively, and wherein halides are selected from the group consisting of chloride, bromide and fluoride, (ii) reacting said amide or said substituted aromatic amine having at least two $-NH_2$ groups of ($a_3$)(i) and said azo containing compound in the presence of a suitable base and a controlled amount of protic material at a reaction temperature of about 10° C. to about 150° C. in a confined reaction zone to produce a substituted aromatic azo compound wherein the molar ratio of protic material to base is 0:1 to about 5:1, and (iii) reacting said substituted aromatic azo compound of ($a_3$)(ii) with a nucleophilic compound selected from the group consisting of aniline, substituted aniline derivatives, aliphatic amines, substituted aliphatic amine derivatives, amides and substituted aromatic amines having at least two $-NH_2$ groups in the presence of a suitable solvent system, a suitable base and a controlled amount of protic material at a reaction temperature of about 70° C. to about 200° C. in a confined reaction zone to produce a substituted aromatic amine having at least two $-NH_2$ groups, wherein the molar ratio of protic material to base is 0:1 to about 5:1; or ($a_4$)
(i) contacting an amide and an azo containing compound represented by the formula $X-R_1-N=$ N—R$_2$—Y or azoxy or hydrazo derivatives thereof in the presence of a suitable solvent system, wherein R$_1$ is an aromatic group, R$_2$ is selected from the group consisting of aliphatic and aromatic groups, and X and Y are independently selected from the group consisting of hydrogen, halides, —NO$_2$, —NH$_2$, aryl groups, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected from the group consisting of aliphatic and aromatic groups, if R$_2$ is aliphatic, X is in the meta or ortho position on R$_1$ and if R$_2$ is aromatic, at least one of X and Y is in the meta or ortho position on R$_1$ and R$_2$, respectively, and wherein halides are selected from the group consisting of chloride, bromide and fluoride, (ii) reacting said amide of (a$_4$)(i) and said azo containing compound in the presence of a suitable base and a controlled amount of protic material at a reaction temperature of about 10° C. to about 150° C. in a confined reaction zone to produce a substituted aromatic azo compound, wherein the molar ratio of protic material to base is 0:1 to about 5:1, (iii) reacting said substituted aromatic azo compound of (a$_4$)(ii) with a nucleophilic compound selected from the group consisting of aniline, substituted aniline derivatives, aliphatic amines, substituted aliphatic amine derivatives, amides and substituted aromatic amines having at least two —NH$_2$ groups in the presence of a suitable solvent system, a suitable base and a controlled amount of protic material at a reaction temperature of about 70° C. to about 200° C. in a confined reaction zone to produce a substituted aromatic amine containing an aromatic amide bond wherein the molar ratio of protic material to base is 0:1 to about 5:1, and (iv) reacting said substituted aromatic amine of (a$_4$)(iii) with ammonia under conditions which produce the corresponding substituted aromatic amine having at least two —NH$_2$ groups and amide; or (a$_5$)

(i) contacting a nucleophilic compound selected from the group consisting of aniline, substituted aniline derivatives, aliphatic amines, substituted aliphatic amine derivatives, amides and substituted aromatic amines having at least two —NH$_2$ groups with a substituted aromatic azo compound or azoxy or hydrazo derivatives thereof in the presence of a suitable solvent system, and (ii) reacting said nucleophilic compound and said substituted aromatic azo compound or azoxy or hydrazo derivatives thereof in the presence of a suitable base and a controlled amount of protic material at a reaction temperature of about 70° C. to about 200° C. to produce a substituted aromatic amine having at least two —NH$_2$ groups, wherein the molar ratio of protic material to base is 0:1 to about 5:1, wherein the substituted aromatic azo compound is selected from the group consisting of compounds represented by the formula:

compounds represented by the formula:

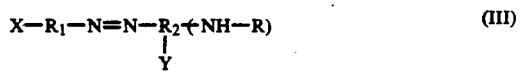

compounds represented by the formula:

$$X-R_1-N=N-R_2\!\!+\!\!NH-R) \qquad (III)$$
$$\phantom{X-R_1-N=N-R_2+NH-R)}|$$
$$\phantom{X-R_1-N=N-R_2+NH-R}Y$$

and mixtures thereof, wherein R—NH— represents a substituent derived from an amide or a substituted aromatic amine having at least two —NH$_2$ groups, wherein said amide is selected from the group consisting of diamides, substituted aliphatic amides represented by the formula

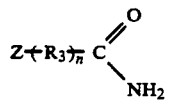

and substituted aromatic amides containing at least one substituent on the aromatic ring selected from the group consisting of —NH$_2$ and alkyl, aryl, aralkyl and alkaryl groups containing at least one —NH$_2$ group, wherein n is 0 or 1, R$_3$ is selected from the group consisting of alkyl, aralkyl, alkenyl, aralkenyl, cycloalkyl and cycloalkenyl groups, Z is selected from the group consisting of —NH$_2$ and alkyl, aryl, aralkyl and alkaryl groups containing at least one —NH$_2$ group, R$_1$ is an aromatic group, R$_2$ is selected from the group consisting of aliphatic and aromatic groups, and X and Y are independently selected from the group consisting of hydrogen, halides, —NO$_2$, —NH$_2$, aryl groups, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected from the group consisting of aliphatic and aromatic groups, halides are selected from the group consisting of chlorine, bromine and fluorine and R$_2$ is an aromatic group in substituted aromatic azo compounds (II) and (III); or (a$_6$)

(i) contacting a nucleophilic compound selected from the group consisting of aniline, substituted aniline derivatives, aliphatic amines, substituted aliphatic amine derivatives, amides and substituted aromatic amines having at least two —NH$_2$ groups with a substituted aromatic azo compound or azoxy or hydrazo derivatives thereof in the presence of a suitable solvent system, (ii) reacting said nucleophilic compound and said substituted aromatic azo compound or azoxy or hydrazo derivatives thereof in the presence of a suitable base and a controlled amount of protic material at a reaction temperature of about 70° C. to about 200° C. to produce a substituted aromatic amine containing an aromatic amide bond, wherein the molar ratio of protic material to base is 0:1 to about 5:1, wherein the substituted aromatic azo compound is selected from the group consisting of compounds represented by the formula:

$$(R-NH)_{\overline{1}}R_1-N=N-R_2, \quad (I)$$
$$\phantom{(R-NH)_{\overline{1}}R_1-N=N-}\overset{|}{X}\phantom{N=N-}\overset{|}{Y}$$

compounds represented by the formula:

$$(R-NH)_{\overline{1}}R_1-N=N-R_2(NH-R), \quad (II)$$
$$\phantom{(R-NH)_{\overline{1}}R_1-N=}\overset{|}{X}\phantom{N=N-}\overset{|}{Y}$$

compounds represented by the formula:

$$X-R_1-N=N-R_2(NH-R) \quad (III)$$
$$\phantom{X-R_1-N=N-R_2}\overset{|}{Y}$$

and mixtures thereof, wherein R—NH— represents a substituent derived from an amide, $R_1$ is an aromatic group, $R_2$ is selected from the group consisting of aliphatic and aromatic groups, and X and Y are independently selected from the group consisting of hydrogen, halides, —$NO_2$, —$NH_2$, aryl groups, alkyl groups, alkoxy groups, —$SO_3$, —$SO_3R_{30}$, —$OR_{30}$, —$COOR_{30}$, and alkyl, aryl, aralkyl or alkaryl groups containing at least one —$NH_2$ group, wherein $R_{30}$ is selected from the group consisting of aliphatic and aromatic groups, halides are selected from the group consisting of chlorine, bromine and fluorine and $R_2$ is an aromatic group in substituted aromatic azo compounds (II) and (III), and (iii) reacting said substituted aromatic amine of ($a_6$)(ii) with ammonia under conditions which produce the corresponding substituted aromatic amine having at least two —$NH_2$ groups and amide; or ($a_7$)

(i) contacting a substituted aniline derivative, wherein the substituents are selected from the group consisting of halide, —$NO_2$, —$NH_2$, alkyl groups, alkoxy groups, —$SO_3$, —$COOR_{30}$ and aryl, aralkyl or alkaryl groups containing at least one —$NH_2$ group provided said substituted aniline derivative contains at least one substituent selected from the group consisting of —$NO_2$, —$NH_2$ and aryl, aralkyl or alkaryl groups containing at least one —$NH_2$ group, and nitrobenzene in a suitable solvent system, (ii) reacting said substituted aniline derivative and nitrobenzene in a confined reaction zone at a suitable temperature, and in the presence of a controlled amount of protic material, and (iii) reducing the reaction product of ($a_7$)(ii) under conditions to produce a substituted aromatic amine having at least two —$NH_2$ groups, (b) recovering said substituted aromatic amine having at least two —$NH_2$ groups, and ($c_1$)

(i) contacting $CO_2$ and said substituted aromatic amine having at least two —$NH_2$ groups in the presence of an organic, nitrogenous base selected from the group consisting of guanidine compounds, amidine compounds, phosphazene compounds and mixtures thereof, under reaction conditions of time and temperature sufficient to produce the corresponding ammonium carbamate salt, and (ii) reacting in a polar aprotic solvent, said salt with a primary or secondary hydrocarbyl halide under reaction conditions of time and temperature sufficient to produce the corresponding carbamate ester wherein R' represents alkyl, alkenyl, cyloalkyl, cycloalkenyl, aralkyl and aralkenyl radicals having 1 to about 22 carbon atoms provided that R' is not a tertiary radical of the formula $(R)_3C$— or $(R)_2C=C(R)$—.

59. The process according to claim 58 comprising:

(a)

(i) contacting an amide selected from the group consisting of diamides, substituted aliphatic amides represented by the formula $$Z(R_3)_{\overline{n}} C \overset{\displaystyle O}{\underset{\displaystyle NH_2}{\diagdown}}$$

and substituted aromatic amides containing at least one substituent on the aromatic ring selected from the group consisting of —$NO_2$, —$NH_2$ and alkyl, aryl, aralkyl, and alkaryl groups containing at least one —$NH_2$ group, and nitrobenzene in the presence of a suitable solvent system wherein n is 0 or 1, $R_3$ is selected from the group consisting of alkyl, aralkyl, alkenyl, aralkenyl, cycloalkyl and cyloalkenyl groups, and Z is selected from the group consisting of —$NO_2$, —$NH_2$ and alkyl, aryl, aralkyl and alkaryl groups containing at least one —$NH_2$ group, (ii) reacting said amide of (a)(i) and nitrobenzene in the presence of a suitable base and a controlled amount of protic material at a suitable temperature in a confined reaction zone, and (iii) reducing the reaction product of (a)(ii) under conditions which produce a substituted aromatic amine having at least two —$NH_2$ groups;

(b) recovering said substituted aromatic amine having at least two —$NH_2$ groups, and ($c_1$)

(i) contacting $CO_2$ and said substituted aromatic amine having at least two —$NH_2$ groups in the presence of an organic, nitrogenous base selected from the group consisting of guanidine compounds, amidine compounds, phosphazene compounds and mixtures thereof, under reaction conditions of time and temperature sufficient to produce the corresponding ammonium carbamate salt, and (ii) reacting in a polar aprotic solvent, said salt with a primary or secondary hydrocarbyl halide under reaction conditions of time and temperature sufficient to produce the corresponding carbamate ester wherein R' represents alkyl, alkenyl, cyloalkyl, cycloalkenyl, aralkyl and aralkenyl radicals having 1 to about 22 carbon atoms provided that R' is not a tertiary radical of the formula $(R)_3C$— or $(R)_2C=C(R)$—.

60. The process according to claim 58 comprising:

($a_1$)

(i) contacting an amide and nitrobenzene in the presence of a suitable solvent system, (ii) reacting said amide of (a₁)(i) and nitrobenzene in the presence of a suitable base and a controlled amount of protic material at a suitable temperature in a confined reaction zone to produce a p-nitroaromatic amide;

(iii) reducing said p-nitroaromatic amide of (a₁)(ii) under conditions which produce a p-aminoaromatic amide, and (iv) reacting said p-aminoaromatic amide with ammonia under conditions which produce the corresponding substituted aromatic amine having at least two —NH₂ groups and amide, (b) recovering said substituted aromatic amine having at least two —NH₂ groups, and (c₁)
(i) contacting CO₂ and said substituted aromatic amine having at least two —NH₂ groups in the presence of an organic, nitrogenous base selected from the group consisting of guanidine compounds, amidine compounds, phosphazene compounds and mixtures thereof, under reaction conditions of time and temperature sufficient to produce the corresponding ammonium carbamate salt, and (ii) reacting in a polar aprotic solvent, said salt with a primary or secondary hydrocarbyl halide under reaction conditions of time and temperature sufficient to produce the corresponding carbamate ester wherein R' represents alkyl, alkenyl, cyloalkyl, cycloalkenyl, aralkyl and aralkenyl radicals having 1 to about 22 carbon atoms provided that R' is not a tertiary radical of the formula (R)₃C— or (R)₂C=C(R)—.

61. The process according to claim 58 comprising:
(a₂)
(i) contacting an amide and nitrobenzene in the presence of a suitable solvent system, (ii) reacting said amide of (a₂)(i) and nitrobenzene in the presence of a suitable base and a controlled amount of protic material at a suitable temperature in a confined reaction zone to produce a p-nitroaromatic amide, (iii) reacting said p-nitroaromatic amide of (a₂)(ii) with ammonia under conditions which produce the corresponding p-nitroaromatic amine and amide, and (iv) reducing said p-nitroaromatic amine under conditions which produce the corresponding substituted aromatic amine having at least two —NH₂ groups, (b) recovering said substituted aromatic amine having at least two —NH₂ groups, and (c₁)
(i) contacting CO₂ and said substituted aromatic amine having at least two —NH₂ groups in the presence of an organic, nitrogenous base selected from the group consisting of guanidine compounds, amidine compounds, phosphazene compounds and mixtures thereof, under reaction conditions of time and temperature sufficient to produce the corresponding ammonium carbamate salt, and (ii) reacting in a polar aprotic solvent, said salt with a primary or secondary hydrocarbyl halide under reaction conditions of time and temperature sufficient to produce the corresponding carbamate ester wherein R' represents alkyl, alkenyl, cyloalkyl, cycloalkenyl, aralkyl and aralkenyl radicals having 1 to about 22 carbon atoms provided that R' is not a tertiary radical of the formula (R)₃C— or (R)₂C=C(R)—.

62. The process according to claim 58 comprising:
(a₃)
(i) contacting an amide or a substituted aromatic amine having at least two —NH₂ groups, wherein said amide is selected from the group consisting of diamides, substituted aliphatic amides represented by the formula

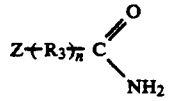

and substituted aromatic amides containing at least one substituent on the aromatic ring selected from the group consisting of —NH₂ and alkyl, aryl, aralkyl and alkaryl groups containing at least one —NH₂ group, and an azo containing compound represented by the formula X—R₁—N=N—R₂—Y or azoxy or hydrazo derivatives thereof in the presence of a suitable solvent system wherein n is 0 or 1, R₃ is selected from the group consisting of alkyl, aralkyl, alkenyl, aralkenyl, cycloalkyl and cycloalkenyl groups, Z is selected from the group consisting of —NH₂ and alkyl, aryl, aralkyl and alkaryl groups containing at least one —NH₂ group, R₁ is an aromatic group, R₂ is selected from the group consisting of aliphatic and aromatic groups, and X and Y are independently selected from the group consisting of hydrogen, halides, —NO₂, —NH₂, aryl groups, alkyl groups, alkoxy groups, —SO₃, —SO₃R₃₀, —OR₃₀, —COOR₃₀, and alkyl, aryl, aralkyl or alkaryl groups containing at least one —NH₂ group, wherein R₃₀ is selected from the group consisting of aliphatic and aromatic groups, if R₂ is aliphatic, X is in the meta or ortho position on R₁ and if R₂ is aromatic, at least one of X and Y is in the meta or ortho position on R₁ and R₂, respectively, and wherein halides are selected from the group consisting of chloride, bromide and fluoride, (ii) reacting said amide or said substituted aromatic amide having at least two —NH₂ groups of (a₃)(i) and said azo containing compound in the presence of a suitable base and a controlled amount of protic material at a reaction temperature of about 10° C. to about 150° C. in a confined reaction zone to produce a substituted aromatic azo compound wherein the molar ratio of protic material to base is 0:1 to about 5:1, and (iii) reacting said substituted aromatic azo compound of (a₃)(ii) with a nucleophilic compound selected from the group consisting of aniline, substituted aniline derivatives, aliphatic amines, substituted aliphatic amine derivatives, amides and substituted aromatic amines having at least two —NH₂ groups in the presence of a suitable solvent system, a suitable base and a controlled amount of protic material at a reaction temperature of about 70° C. to about 200° C. in a confined reaction zone to produce a substituted aromatic amine having at least two —NH$_2$ groups, wherein the molar ratio of protic material to base is 0:1 to about 5:1, (b) recovering said substituted aromatic amine having at least two —NH$_2$ groups, and (c$_1$)
- (i) contacting CO$_2$ and said substituted aromatic amine having at least two —NH$_2$ groups in the presence of an organic, nitrogenous base selected from the group consisting of guanidine compounds, amidine compounds, phosphazene compounds and mixtures thereof, under reaction conditions of time and temperature sufficient to produce the corresponding ammonium carbamate salt, and
- (ii) reacting in a polar aprotic solvent, said salt with a primary or secondary hydrocarbyl halide under reaction conditions of time and temperature sufficient to produce the corresponding carbamate ester wherein R' represents alkyl, alkenyl, cyloalkyl, cycloalkenyl, aralkyl and aralkenyl radicals having 1 to about 22 carbon atoms provided that R' is not a tertiary radical of the formula (R)$_3$C— or (R)$_2$C=C(R)—.

63. The process according to claim 58 comprising:

(a$_4$)
- (i) contacting an amide and an azo containing compound represented by the formula X—R$_1$—N=N—R$_2$—Y or azoxy or hydrazo derivatives thereof in the presence of a suitable solvent system, wherein R$_1$ is an aromatic group, R$_2$ is selected from the group consisting of aliphatic and aromatic groups, and X and Y are independently selected from the group consisting of hydrogen, halides, —NO$_2$, —NH$_2$, aryl groups, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected from the group consisting of aliphatic and aromatic groups, if R$_2$ is aliphatic, X is in the meta or ortho position on R$_1$ and if R$_2$ is aromatic, at least one of X and Y is in the meta or ortho position on R$_1$ and R$_2$, respectively, and wherein halides are selected from the group consisting of chloride, bromide and fluoride,
- (ii) reacting said amide of (a$_4$)(i) and said azo containing compound in the presence of a suitable base and a controlled amount of protic material at a reaction temperature of about 10° C. to about 150° C. in a confined reaction zone to produce a substituted aromatic azo compound, wherein the molar ratio of protic material to base is 0:1 to about 5:1,
- (iii) reacting said substituted aromatic azo compound of (a$_4$)(ii) with a nucleophilic compound selected from the group consisting of aniline, substituted aniline derivatives, aliphatic amines, substituted aliphatic amine derivatives, amides and substituted aromatic amines having at least two —NH$_2$ groups in the presence of a suitable solvent system, a suitable base and a controlled amount of protic material at a reaction temperature of about 70° C. to about 200° C. in a confined reaction zone to produce a substituted aromatic amine containing an aromatic amide bond wherein the molar ratio of protic material to base is 0:1 to about 5:1, and
- (iv) reacting said substituted aromatic amine of (a$_4$)(iii) with ammonia under conditions which produce the corresponding substituted aromatic amine having at least two —NH$_2$ groups and amide, (b) recovering said substituted aromatic amine having at least two —NH$_2$ groups, and (c$_1$)
- (i) contacting CO$_2$ and said substituted aromatic amine having at least two —NH$_2$ groups in the presence of an organic, nitrogenous base selected from the group consisting of guanidine compounds, amidine compounds, phosphazene compounds and mixtures thereof, under reaction conditions of time and temperature sufficient to produce the corresponding ammonium carbamate salt, and
- (ii) reacting in a polar aprotic solvent, said salt with a primary or secondary hydrocarbyl halide under reaction conditions of time and temperature sufficient to produce the corresponding carbamate ester wherein R' represents alkyl, alkenyl, cyloalkyl, cycloalkenyl, aralkyl and aralkenyl radicals having 1 to about 22 carbon atoms provided that R' is not a tertiary radical of the formula (R)$_3$C— or (R)$_2$C=C(R)—.

64. The process according to claim 58 comprising:

(a$_5$)
- (i) contacting a nucleophilic compound selected from the group consisting of aniline, substituted aniline derivatives, aliphatic amines, substituted aliphatic amine derivatives, amides and substituted aromatic amines having at least two —NH$_2$ groups with a substituted aromatic azo compound or azoxy or hydrazo derivatives thereof in the presence of a suitable solvent system, and
- (ii) reacting said nucleophilic compound and said substituted aromatic azo compound or azoxy or hydrazo derivatives thereof in the presence of a suitable base and a controlled amount of protic material at a reaction temperature of about 70° C. to about 200° C. to produce a substituted aromatic amine having at least two —NH$_2$ groups, wherein the molar ratio of protic material to base is 0:1 to about 5:1, wherein the substituted aromatic azo compound is selected from the group consisting of compounds represented by the formula:

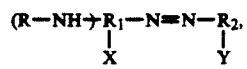

compounds represented by the formula:

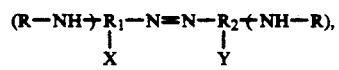

compounds represented by the formula:

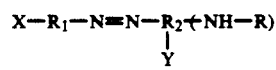

and mixtures thereof, wherein R—NH— represents a substituent derived from an amide or a substituted aromatic amine having at least two —NH$_2$ groups, wherein said amide is selected from the group consisting of diamides, substituted aliphatic amides represented by the formula

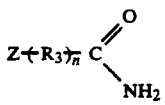

and substituted aromatic amides containing at least one substituent on the aromatic ring selected from the group consisting of —NH$_2$ and alkyl, aryl, aralkyl and alkaryl groups containing at least one —NH$_2$ group, wherein n is 0 or 1, R$_3$ is selected from the group consisting of alkyl, aralkyl, alkenyl, aralkenyl, cycloalkyl and cycloalkenyl groups, Z is selected from the group consisting of —NH$_2$ and alkyl, aryl, aralkyl and alkaryl groups containing at least one —NH$_2$ group, R$_1$ is an aromatic group, R$_2$ is selected from the group consisting of aliphatic and aromatic groups, and X and Y are independently selected from the group consisting of hydrogen, halides, —NO$_2$, —NH$_2$, aryl groups, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected form the group consisting of aliphatic and aromatic groups, halides are selected from the group consisting of chlorine, bromine and fluorine and R$_2$ is an aromatic group in substituted aromatic azo compounds (II) and (III);

(b) recovering said substituted aromatic amine having at least two —NH$_2$ groups, and (c$_1$)

(i) contacting CO$_2$ and said substituted aromatic amine having at least two —NH$_2$ groups in the presence of an organic, nitrogenous base selected from the group consisting of guanidine compounds, amidine compounds, phosphazene compounds and mixtures thereof, under reaction conditions of time and temperature sufficient to produce the corresponding ammonium carbamate salt, and (ii) reacting in a polar aprotic solvent, said salt with a primary or secondary hydrocarbyl halide under reaction conditions of time and temperature sufficient to produce the corresponding carbamate ester wherein R' represents alkyl, alkenyl, cyloalkyl, cycloalkenyl, aralkyl and aralkenyl radicals having 1 to about 22 carbon atoms provided that R' is not a tertiary radical of the formula (R)$_3$C— or (R)$_2$C=C(R)—.

65. The process according to claim 58 comprising:

(a$_6$)

(i) contacting a nucleophilic compound selected from the group consisting of aniline, substituted aniline derivatives, aliphatic amines, substituted aliphatic amine derivatives, amides and substituted aromatic amines having at least two —NH$_2$ groups with a substituted aromatic azo compound or azoxy or hydrazo derivatives thereof in the presence of a suitable solvent system, (ii) reacting said nucleophilic compound and said substituted aromatic azo compound or azoxy or hydrazo derivatives thereof in the presence of a suitable base and a controlled amount of protic material at a reaction temperature of about 70° C. to about 200° C. to produce a substituted aromatic amine containing an aromatic amide bond, wherein the molar ratio of protic material to base is 0:1 to about 5:1, wherein the substituted aromatic azo compound is selected from the group consisting of compounds represented by the formula:

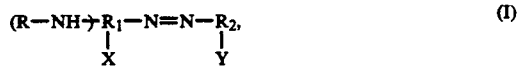

compounds represented by the formula:

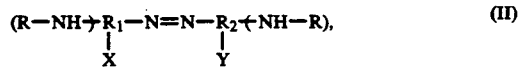

compounds represented by the formula:

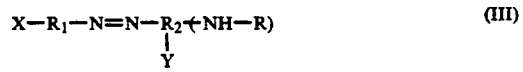

and mixtures thereof, wherein R—NH— represents a substituent derived from an amide, R$_1$ is an aromatic group, R$_2$ is selected from the group consisting of aliphatic and aromatic groups, and X and Y are independently selected from the group consisting of hydrogen, halides, —NO$_2$, —NH$_2$, aryl groups, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein B$_{30}$ is selected from the group consisting of aliphatic and aromatic groups, halides are selected from the group consisting of chlorine, bromine and fluorine and R$_2$ is an aromatic group in substituted aromatic azo compounds (II) and (III), and (iii) reacting said substituted aromatic amine of (a$_6$)(ii) with ammonia under conditions which produce the corresponding substituted aromatic amine having at least two —NH$_2$ groups and amide, (b) recovering said substituted aromatic amine having at least two —NH$_2$ groups, and (c$_1$)

(i) contacting CO$_2$ and said substituted aromatic amine having at least two —NH$_2$ groups in the presence of an organic, nitrogenous base selected from the group consisting of guanidine compounds, amidine compounds, phosphazene compounds and mixtures thereof, under reaction conditions of time and temperature sufficient to produce the corresponding ammonium carbamate salt, and (ii) reacting in a polar aprotic solvent, said salt with a primary or secondary hydrocarbyl halide under reaction conditions of time and temperature sufficient to produce the corresponding carbamate ester wherein R' represents alkyl, alkenyl, cyloalkyl, cycloalkenyl, aralkyl and aralkenyl radicals having 1 to about 22 carbon atoms provided that R' is not a tertiary radical of the formula $(R)_3C—$ or $(R)_2C=C(R)—$.

66. The process according to claim 58 comprising:

(a₇)
(i) contacting a substituted aniline derivative, wherein the substituents are selected from the group consisting of halide, $—NO_2$, $—NH_2$, alkyl groups, alkoxy groups, $—SO_3$, $—COOR_{30}$ and aryl, aralkyl or alkaryl groups containing at least one $—NH_2$ group provided said substituted aniline derivative contains at least one substituent selected from the group consisting of $—NO_2$, $—NH_2$ and aryl, aralkyl or alkaryl groups containing at least one $—NH_2$ group, and nitrobenzene in a suitable solvent system, $R_{30}$ is selected from the group consisting of aliphatic and aromatic groups, (ii) reacting said substituted aniline derivative and nitrobenzene in a confined reaction zone at a suitable temperature, and in the presence of a controlled amount of protic material, and (iii) reducing the reaction product of (a₇)(ii) under conditions to produce a substituted aromatic amine having at least two $—NH_2$ groups, (b) recovering said substituted aromatic amine having at least two $—NH_2$ groups, and (c₁)
(i) contacting $CO_2$ and said substituted aromatic amine having at least two $—NH_2$ groups in the presence of an organic, nitrogenous base selected from the group consisting of guanidine compounds, amidine compounds, phosphazene compounds and mixtures thereof, under reaction conditions of time and temperature sufficient to produce the corresponding ammonium carbamate salt, and (ii) reacting in a polar aprotic solvent, said salt with a primary or secondary hydrocarbyl halide under reaction conditions of time and temperature sufficient to produce the corresponding carbamate ester wherein R' represents alkyl, alkenyl, cyloalkyl, cycloalkenyl, aralkyl and aralkenyl radicals having 1 to about 22 carbon atoms provided that R' is not a tertiary radical of the formula $(R)_3C—$ or $(R)_2C=C(R)—$.

67. The process according to claim 58 wherein said diamide of Step (a) is represented by the formula:

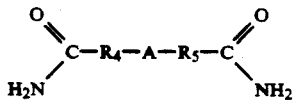

wherein $R_4$ and $R_5$ are independently selected from the group consisting of aromatic groups, aliphatic groups and a direct bond, and A is selected from the group consisting of

$—SO_2—$, $—O—$, $—S—$ and a direct bond.

68. The process according to claim 58 wherein said suitable solvent system of Step (a) includes a solvent selected from the group consisting of nitrobenzene, dimethylsulfoxide, dimethylformamide, N-methyl-2-pyrrolidone, pyridine, N-methylaniline, chlorobenzene, tetraalkyl ammonium hydroxide or amides having a melting point below the reaction temperature and mixtures thereof.

69. The process according to claim 58 wherein the molar ratio of said protic material to said suitable base in Step (a) is less than about 5:1 and the ratio of equivalents of said suitable base to equivalents of said amide in Step (a) is about 1:1 to about 10:1.

70. The process according to claim 58 wherein said suitable base of Step (a) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

71. The process according to claim 58 wherein said amide of Step (a₁) is selected from the group consisting of aromatic amides, aliphatic amides, substituted aromatic amide derivatives, substituted aliphatic amide derivatives and diamides having the formula:

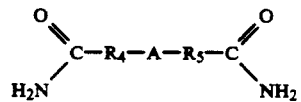

wherein $R_4$ and $R_5$ are independently selected from the group consisting of aromatic groups, aliphatic groups and a direct bond, and A is selected from the group consisting of

$—SO_2—$, $—O—$, $—S—$ and a direct bond, said aliphatic amides and said substituted aliphatic amide derivatives are represented by the formula:

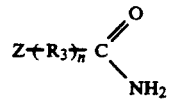

wherein n is 0 or 1, $R_3$ is selected from the group consisting of alkyl, aralkyl, alkenyl, aralkenyl, cycloalkyl and cycloalkenyl groups and Z is selected from the group consisting of hydrogen, $—NO_2$, $—NH_2$, aryl groups, alkoxy groups, $—SO_3$, $—SO_3R_{30}$, $—OR_{30}$, $—COOR_{30}$, and alkyl, aryl, aralkyl or alkaryl groups containing at least one $—NH_2$ group, and the substituent of said substituted aromatic amide derivatives is selected from the group consisting of halide, $—NO_2$, $—NH_2$, alkyl groups, alkoxy groups, $—SO_3$, $—SO_3R_{30}$, $—OR_{30}$, $—COOR_{30}$, and alkyl, aryl, aralkyl or alkaryl groups containing at least one $—NH_2$ group, wherein $R_{30}$ is selected from the group consisting of aliphatic and aromatic groups, and halides are selected from the group consisting of chloride, bromide and fluoride.

72. The process according to claim 58 wherein said suitable solvent system of Step (a₁) includes a solvent selected from the group consisting of nitrobenzene, dimethylsulfoxide, dimethylformamide, N-methyl-2-pyrrolidone, pyridine, N-methylaniline, chlorobenzene, tetraalkyl ammonium hydroxide or amides having a melting point below the reaction temperature and mixtures thereof.

73. The process according to claim 58 wherein the molar ratio of said protic material to said suitable base in Step ($a_1$) is less than about 5:1 and the ratio of equivalents of said suitable base to equivalents of said amide in Step (a) is about 1:1 to about 10:1.

74. The process according to claim 58 wherein said suitable base of Step ($a_1$) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

75. The process according to claim 58 wherein said amide of Step ($a_2$) is selected from the group consisting of aromatic amides, aliphatic amides, substituted aromatic amide derivatives, substituted aliphatic amide derivatives and diamides having the formula:

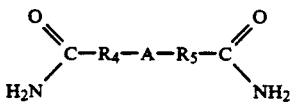

wherein $R_4$ and $R_5$ are independently selected from the group consisting of aromatic groups, aliphatic groups and a direct bond, and A is selected from the group consisting of

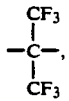

—$SO_2$—, —O—, —S— and a direct bond, said aliphatic amides and said substituted aliphatic amide derivatives are represented by the formula:

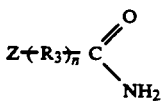

wherein n is 0 or 1, $R_3$ is selected from the group consisting of alkyl, aralkyl, alkenyl, aralkenyl, cycloalkyl and cycloalkenyl groups and Z is selected from the group consisting of hydrogen, —$NO_2$, —$NH_2$, aryl groups, alkoxy groups, —$SO_3$, —$SO_3R_{30}$, —$OR_{30}$, —$COOR_{30}$, and alkyl, aryl, aralkyl or alkaryl groups containing at least one —$NH_2$ group, and the substituent of said substituted aromatic amide derivatives is selected from the group consisting of halide, —$NO_2$, —$NH_2$, alkyl groups, alkoxy groups, —$SO_3$, —$SO_3R_{30}$, —$OR_{30}$, —$COOR_{30}$, and alkyl, aryl, aralkyl or alkaryl groups containing at least one —$NH_2$ group, wherein $R_{30}$ is selected from the group consisting of aliphatic and aromatic groups, and halides are selected from the group consisting of chloride, bromide and fluoride.

76. The process according to claim 58 wherein said suitable solvent system of Step ($a_2$) includes a solvent selected from the group consisting of nitrobenzene, dimethylsulfoxide, dimethylformamide, N-methyl-2-pyrrolidone, pyridine, N-methylaniline, chlorobenzene, tetraalkyl ammonium hydroxide or amides having a melting point below the reaction temperature and mixtures thereof.

77. The process according to claim 58 wherein the molar ratio of said protic material to said suitable base in Step ($a_2$) is less than about 5:1 and the ratio of equivalents of said suitable base to equivalents of said amide in Step (a) is about 1:1 to about 10:1.

78. The process according to claim 58 wherein said suitable base of Step ($a_2$) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

79. The process according to claim 58 wherein said diamide of Step ($a_3$) is represented by the formula:

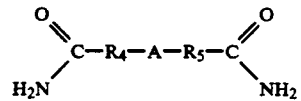

wherein $R_4$ and $R_5$ are independently selected from the group consisting of aromatic groups, aliphatic groups and a direct bond, and A is selected from the group consisting of

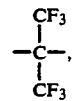

—$SO_2$—, —O—, —S— and a direct bond.

80. The process according to claim 58 wherein said suitable solvent system of Step ($a_3$) includes a solvent selected from the group consisting of aniline, dimethylsulfoxide, dimethylformamide, N-methyl-2-pyrrolidone, pyridine, ethylene glycol dimethyl ether, diisopropylamine, molten benzamide and mixtures thereof.

81. The process according to claim 58 wherein said suitable base of Step ($a_3$) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

82. The process according to claim 58 wherein said amide of Step ($a_4$) is selected from the group consisting of aromatic amides, aliphatic amides, substituted aromatic amide derivatives, substituted aliphatic amide derivatives and diamides having the formula:

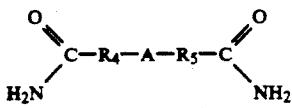

wherein R₄ and R₅ are independently selected from the group consisting of aromatic groups, aliphatic groups and a direct bond, and A is selected from the group consisting of

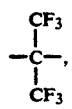

—SO₂—, —O—, —S— and a direct bond, said aliphatic amides and said substituted aliphatic amide derivatives are represented by the formula:

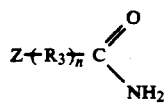

wherein n is 0 or 1, R₃ is selected from the group consisting of alkyl, aralkyl, alkenyl, aralkenyl, cycloalkyl and cycloalkenyl groups and Z is selected from the group consisting of hydrogen, —NO₂, —NH₂, aryl groups, alkoxy groups, —SO₃, —SO₃R₃₀, —OR₃₀, —COOR₃₀, and alkyl, aryl, aralkyl or alkaryl groups containing at least one —NH₂ group, and the substituent of said substituted aromatic amide derivatives is selected from the group consisting of halide, —NO₂, —NH₂, alkyl groups, alkoxy groups, —SO₃, —SO₃R₃₀, —OR₃₀, —COOR₃₀, and alkyl, aryl, aralkyl or alkaryl groups containing at least one —NH₂ group, wherein R₃₀ is selected from the group consisting of aliphatic and aromatic groups, and halides are selected from the group consisting of chloride, bromide and fluoride.

83. The process according to claim 58 wherein said suitable solvent system of Step (a₄) includes a solvent selected from the group consisting of aniline, dimethylsulfoxide, dimethylformamide, N-methyl-2-pyrrolidone, pyridine, ethylene glycol dimethyl ether, diisopropylamine, molten benzamide and mixtures thereof.

84. The process according to claim 58 wherein said suitable base of Step (a₄) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

85. The process according to claim 58 wherein said suitable solvent system of Step (a₅) includes a solvent selected from the group consisting of aniline, dimethylsulfoxide, dimethylformamide, N-methyl-2-pyrrolidone, pyridine, ethylene glycol dimethyl ether, diisopropylamine, molten benzamide and mixtures thereof.

86. The process according to claim 58 wherein said suitable base of Step (a₅) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

87. The process according to claim 58 wherein said diamide of Step (a₅)(ii) is represented by the formula:

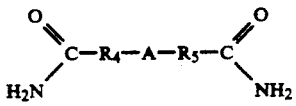

wherein R₄ and R₅ are independently selected from the group consisting of aromatic groups, aliphatic groups and a direct bond, and A is selected from the group consisting of

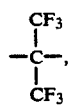

—SO₂—, —O—, —S— and a direct bond.

88. The process according to claim 58 wherein said suitable solvent system of Step (a₆) includes a solvent selected from the group consisting of aniline, dimethylsulfoxide, dimethylformamide, N-methyl-2-pyrrolidone, pyridine, ethylene glycol dimethyl ether, diisopropylamine, molten benzamide and mixtures thereof.

89. The process according to claim 58 wherein said suitable base of Step (a₆) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

90. The process according to claim 58 wherein said amide of Step (a₆) is selected from the group consisting of aromatic amides, aliphatic amides, substituted aromatic amide derivatives, substituted aliphatic amide derivatives and diamides having the formula:

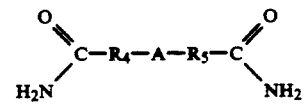

wherein R₄ and R₅ are independently selected from the group consisting of aromatic groups, aliphatic groups and a direct bond, and A is selected from the group consisting of

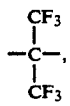

—SO$_2$—, —O—, —S— and a direct bond, said aliphatic amides and said substituted aliphatic amide derivatives are represented by the formula:

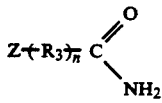

wherein n is 0 or 1, R$_3$ is selected from the group consisting of alkyl, aralkyl, alkenyl, aralkenyl, cycloalkyl and cycloalkenyl groups and Z is selected from the group consisting of hydrogen, —NO$_2$, —NH$_2$, aryl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, and the substituent of said substituted aromatic amide derivatives is selected from the group consisting of halide, —NO$_2$, —NH$_2$, alkyl groups, alkoxy groups, —SO$_3$, —SO$_3$R$_{30}$, —OR$_{30}$, —COOR$_{30}$, and alkyl, aryl, aralkyl or alkaryl groups containing at least one —NH$_2$ group, wherein R$_{30}$ is selected from the group consisting of aliphatic and aromatic groups, and halides are selected from the group consisting of chloride, bromide and fluoride.

91. The process according to claim 58 wherein said suitable solvent system of Step (a$_7$) includes a solvent selected from the group consisting of nitrobenzene, dimethylsulfoxide, dimethylformamide, N-methyl-2-pyrrolidone, pyridine, toluene, hexane, ethylene glycol dimethyl ether, diisopropylethylamine and mixtures thereof.

92. The process according to claim 58 wherein the molar ratio of said protic material to said suitable base in Step (a$_7$) is less than about 6:1.

93. The process according to claim 58 wherein said suitable base of Step (a$_7$) is selected from the group consisting of organic bases, inorganic bases and aryl ammonium, alkyl ammonium, aryl/alkyl ammonium or alkyl diammonium salt in conjunction with a base source wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides and mixtures thereof.

94. The process according to claim 58 wherein said polar aprotic solvent of Step (c$_1$) is selected from the group consisting of dimethylsulfoxide, dimethylformamide, acetonitrile and N-methyl-2-pyrrolidone.

95. The process according to claim 58 wherein said primary or secondary hydrocarbyl halide of Step (c$_1$) is represented by the formula R'X" or X"R'X", wherein R' represents alkyl, alkenyl, cycloalkyl, cycloalkenyl, aralkyl and aralkenyl radicals having 1 to about 22 carbon atoms, provided that R' is not a tertiary radical of the formula (R)$_3$C— or (R)$_2$C=C(R)—; and X" represents a halide.

96. The process according to claim 1 wherein said substituted aromatic amine having at least two —NH$_2$ groups is p-phenylenediamine and said isocyanate is 1,4-phenylene diisocyanate wherein said p-phenylenediamine is produced by Step (a$_1$), (a$_2$), (a$_4$) or (a$_6$).

97. The process according to claim 58 wherein said substituted aromatic amine having at least two —NH$_2$ groups is p-phenylenediamine and said carbamate ester is represented by the formula:

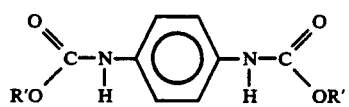

wherein said p-phenylenediamine is produced by Step (a$_1$), (a$_2$), (a$_4$) or (a$_6$).

* * * * *

UNITED STATES PATENT OFFICE
CERTIFICATE OF CORRECTION

PATENT NO. : 5,233,010

DATED : August 3, 1993

INVENTOR(S) : William D. McGhee et al.

It is certified that error appears in the above-identified patent and that said Letters Patent is hereby corrected as shown below:

Col. 44, line 56, delete "$NO_6$" and insert therefor —$NO_y$—.

Col. 56, line 41, after "wherein" insert —n—.

Col. 79, line 31, delete "form" and insert therefor —from—.

Col. 80, line 39, delete "$B_{30}$" and insert therefor —$R_{30}$—.

Signed and Sealed this

First Day of November, 1994

Attest:

BRUCE LEHMAN

*Attesting Officer*  *Commissioner of Patents and Trademarks*